(12) United States Patent
Ulbert et al.

(10) Patent No.: US 10,060,924 B2
(45) Date of Patent: Aug. 28, 2018

(54) DISTINGUISHING FLAVIVIRUS INFECTION USING A RECOMBINANT MUTANT ENVELOPE PROTEIN

(71) Applicants: Fraunhofer-Gesellschaft Zur Förderung Der Angewandten Forschung E.V., München (DE); Washington University, St. Louis, MO (US)

(72) Inventors: Sebastian Ulbert, Leipzig (DE); Stefan Chabierski, Kossa (DE); Michael Diamond, St. Louis, MO (US); Daved Fremont, St. Louis, MO (US)

(73) Assignees: Fraunhofer-Gesellschaft Zur Förderung Der Angewandten Forschung E.V., München (DE); Washington University, St. Louis, MO (US)

( * ) Notice: Subject to any disclaimer, the term of this patent is extended or adjusted under 35 U.S.C. 154(b) by 0 days.

(21) Appl. No.: 15/126,150

(22) PCT Filed: Aug. 22, 2014

(86) PCT No.: PCT/EP2014/067912
§ 371 (c)(1),
(2) Date: Sep. 14, 2016

(87) PCT Pub. No.: WO2015/139784
PCT Pub. Date: Sep. 24, 2015

(65) Prior Publication Data
US 2017/0089897 A1      Mar. 30, 2017

(30) Foreign Application Priority Data
Mar. 18, 2014   (EP) .................................. 14160442

(51) Int. Cl.
*G01N 33/569*   (2006.01)
*C07K 14/005*   (2006.01)
*A61K 39/12*    (2006.01)
*A61K 39/00*    (2006.01)
*C12N 7/00*     (2006.01)

(52) U.S. Cl.
CPC ..... *G01N 33/56983* (2013.01); *C07K 14/005* (2013.01); *C12N 2770/24122* (2013.01); *G01N 2333/185* (2013.01); *G01N 2469/20* (2013.01)

(58) Field of Classification Search
CPC ............ A61K 39/12; A61K 2039/5254; A61K 2039/5252; A61K 2039/5258; A61K 2039/70; A61K 2039/53; A61K 35/76; A61K 39/42; A61K 2039/6075; A61K 38/162; C12N 7/00; C12N 15/86; C12N 2770/24121; C12N 2770/24144; C12N 2770/24151; C12N 2770/24162; C07K 14/005; C07K 16/1081; C07K 14/1825; C07K 16/10; C07K 14/08
See application file for complete search history.

(56) References Cited

FOREIGN PATENT DOCUMENTS

WO    WO-2006025990 A2    3/2006

OTHER PUBLICATIONS

Aaskov et al., Long-term transmission of defective RNA viruses in humans and Aedes mosquitoes. Science. Jan. 13, 2006;311(5758):236-8.
Altschul et al., Gapped BLAST and PSI-BLAST: a new generation of protein database search programs. Nucleic Acids Res. Sep. 1, 1997;25(17):3389-402.
Barzon et al., New endemic West Nile virus lineage 1a in northern Italy, Jul. 2012. Euro Surveill. Aug. 2, 2012;17(31). pii: 20231. Erratum in: Euro Surveill. 2012;17(32). pii: 20244.
Barzon et al., The complex epidemiological scenario of West Nile virus in Italy. Int J Environ Res Public Health. Sep. 30, 2013;10(10):4669-89.
Beltramello et al., The human immune response to Dengue virus is dominated by highly cross-reactive antibodies endowed with neutralizing and enhancing activity. Cell Host Microbe. Sep. 16, 2010;8(3):271-83.
Chabierski et al., Antibody responses in humans infected with newly emerging strains of West Nile Virus in Europe. PLoS One. Jun. 12, 2013;8(6):e66507.
Chiou et al., Enzyme-linked immunosorbent assays using novel Japanese encephalitis virus antigen improve the accuracy of clinical diagnosis of flavivirus infections. Clin Vaccine Immunol. May 2008;15(5):825-35.
Crill et al., A detailed mutagenesis study of flavivirus cross-reactive epitopes using West Nile virus-like particles. J Gen Virol. Apr. 2007;88(Pt 4):1169-74.
Crill et al., Localization and characterization of flavivirus envelope glycoprotein cross-reactive epitopes. J Virol. Dec. 2004;78(24):13975-86.
Diamond et al., The host immunologic response to West Nile encephalitis virus. Front Biosci (Landmark Ed). Jan. 1, 2009;14:3024-34.
Diamond et al., The structural immunology of antibody protection against West Nile virus. Immunol Rev. Oct. 2008;225:212-25.
Donoso-Mantke et al., Tick-Borne Encephalitis Virus: A General Overview, In Flavivirus Encephalitis, Edited by Daniel Ruzek, ISBN: 978-953-307-669-0, InTech, 2011.
Faggioni et al., West Nile alternative open reading frame (N-NS4B/WARF4) is produced in infected West Nile Virus (WNV) cells and induces humoral response in WNV infected individuals. Virol J. Nov. 22, 2012;9:283.

(Continued)

*Primary Examiner* — Rachel B Gill
(74) *Attorney, Agent, or Firm* — Mintz Levin Cohn Ferris Glovsky and Popeo, P.C.

(57) ABSTRACT

The present invention relates to mutant peptides of the E protein of the West Nile virus and other flaviviruses useful for discriminating flaviviral infections, as well as kits, methods and uses related thereto.

Figure 3:
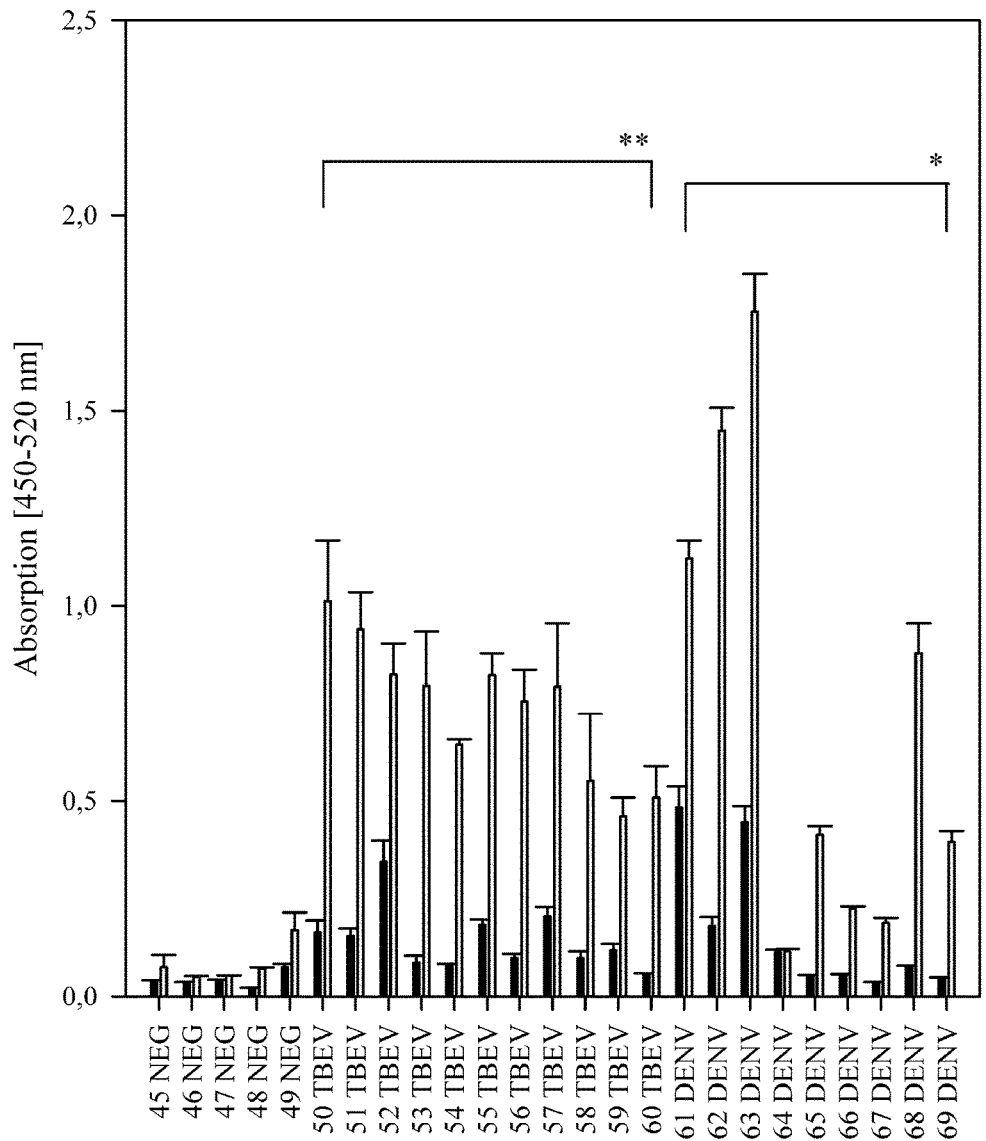

20 Claims, 11 Drawing Sheets
Specification includes a Sequence Listing.

(56) References Cited

OTHER PUBLICATIONS

Hayes et al., Virology, pathology, and clinical manifestations of West Nile virus disease. Emerg Infect Dis. Aug. 2005;11(8):1174-9.
Lanciotti et al., Complete genome sequences and phylogenetic analysis of West Nile virus strains isolated from the United States, Europe, and the Middle East. Virology. Jun. 20, 2002;298(1):96-105.
Maeda et al., Review of diagnostic plaque reduction neutralization tests for flavivirus infection. Vet J. Jan. 2013;195(1):33-40.
Magurano et al., Circulation of West Nile virus lineage 1 and 2 during an outbreak in Italy. Clin Microbiol Infect. Dec. 2012;18(12):E545-7.
Murray et al., West Nile virus and its emergence in the United States of America. Vet Res. Nov.-Dec. 2010;41(6):67.
Nybakken et al., Crystal structure of the West Nile virus envelope glycoprotein. J Virol. Dec. 2006;80(23):11467-74.
Nybakken et al., Structural basis of West Nile virus neutralization by a therapeutic antibody. Nature. Sep. 29, 2005;437(7059):764-9.
Oliphant et al., Induction of epitope-specific neutralizing antibodies against West Nile virus. J Virol. Nov. 2007;81(21):11828-39.
Papa et al., Acute West Nile virus neuroinvasive infections: cross-reactivity with dengue virus and tick-borne encephalitis virus. J Med Virol. Oct. 2011;83(10):1861-5.
Papa, A. West Nile virus infections in Greece: an update. Expert Rev Anti Infect Ther. Jul. 2012;10(7):743-50.
Roberson et al., Differentiation of West Nile and St. Louis encephalitis virus infections by use of noninfectious virus-like particles with reduced cross-reactivity. J Clin Microbiol. Oct. 2007;45(10):3167-74.
Sambri et al., Diagnosis of west nile virus human infections: overview and proposal of diagnostic protocols considering the results of external quality assessment studies. Viruses. Sep. 25, 2013;5(10):2329-48.
Sambri et al., West Nile virus in Europe: emergence, epidemiology, diagnosis, treatment, and prevention. Clin Microbiol Infect. Aug. 2013;19(8):699-704.
Sanchini et al., Second international diagnostic accuracy study for the serological detection of West Nile virus infection. PLoS Negl Trop Dis. Apr. 25, 2013;7(4):e2184.
Sirbu et al., Outbreak of West Nile virus infection in humans, Romania, Jul. to Oct. 2010. Euro Surveill. Jan. 13, 2011;16(2).
Smith et al., The potent and broadly neutralizing human dengue virus-specific monoclonal antibody 1C19 reveals a unique cross-reactive epitope on the bc loop of domain II of the envelope protein. MBio. Nov. 19, 2013;4(6):e00873-13.
Throsby et al., Isolation and characterization of human monoclonal antibodies from individuals infected with West Nile Virus. J Virol. Jul. 2006;80(14):6982-92.
Tsai et al., High-avidity and potently neutralizing cross-reactive human monoclonal antibodies derived from secondary dengue virus infection. J Virol. Dec. 2013;87(23):12562-75.
UniProt Accession No. A1BY44, Jan. 23, 2007.
UniProt Accession No. Q29ZZ0, Apr. 4, 2006.
UniProt Accession No. Q2XRR1, Dec. 20, 2005.
Vogt et al., Poorly neutralizing cross-reactive antibodies against the fusion loop of West Nile virus envelope protein protect in vivo via Fcgamma receptor and complement-dependent effector mechanisms. J Virol. Nov. 2011;85(22):11567-80.

Figure 1

```
                70         80         90        100        110        120
                +----+----+----+----+----+----+----+----+----+----+----+
WNV-E      ATVSDLSTKAACPTMGEAHNDKRADPAFVCRQGVVDRGWGNGCGLFGKGSIDTCAKFA
WNV-EQuad  ATVSDLSTKAACPACGEAHNDKRADPAFVCRQGVVDRGCGNGCRFGKGSIDTCAKFA
TBEV-E     AKLSDTKVAARCPTMGPATLAKEHQGGTVCKRDQSDRGWGNHCGLFGKGSIVACVKAA
DENV1-E    AKISNTTTDSRCPTQGEATLVEEQDANFVCRRTFVDRGWGNGCGLFGKGSLLTCAKFK
DENV2-E    AKLTNTTESRCPTQGEPSLVEEQDKRFVCRHSMVDRGWGNGCGLFGKGGIVTCAMFT
DENV3-E    GKITNITTDSRCPTQGEAVLPEEQDQNYVCKHTYVDRGWGNGCGLFGKGSLVTCAKFQ
DENV4-E    ASISNITTATRCPTQGEPYLKEEQDQQYICRRDVVDRGWGNGCGLFGKGGVVTCAKFA
```

Figure 2

Absorption [450-520 nm]

| | |
|---|---|
| 1 WNV US | |
| 2 WNV US | |
| 3 WNV I | |
| 4 WNV I | |
| 5 WNV I | |
| 6 WNV I | |
| 7 WNV I | |
| 8 WNV I | |
| 9 WNV I | |
| 10 WNV I | |
| 11 WNV I | |
| 12 WNV I | |
| 13 WNV I | |
| 14 WNV I | |
| 15 WNV I | |
| 16 WNV I | |
| 17 WNV G | |
| 18 WNV G | |
| 19 WNV G | |
| 20 WNV G | |
| 21 WNV G | |
| 22 WNV G | |
| 23 WNV G | |
| 24 WNV G | |
| 25 WNV G | |
| 26 WNV C | |
| 27 WNV C | |
| 28 WNV C | |
| 29 WNV C | |
| 30 WNV C | |
| 31 WNV C | |
| 32 WNV C | |
| 33 WNV C | |
| 34 WNV C | |
| 35 WNV C | |
| 36 WNV C | |
| 37 WNV C | |
| 38 WNV C | |
| 39 WNV C | |
| 40 WNV C | |
| 41 WNV C | |
| 42 WNV C | |
| 43 WNV C | |
| 44 WNV C | |

Figure 4
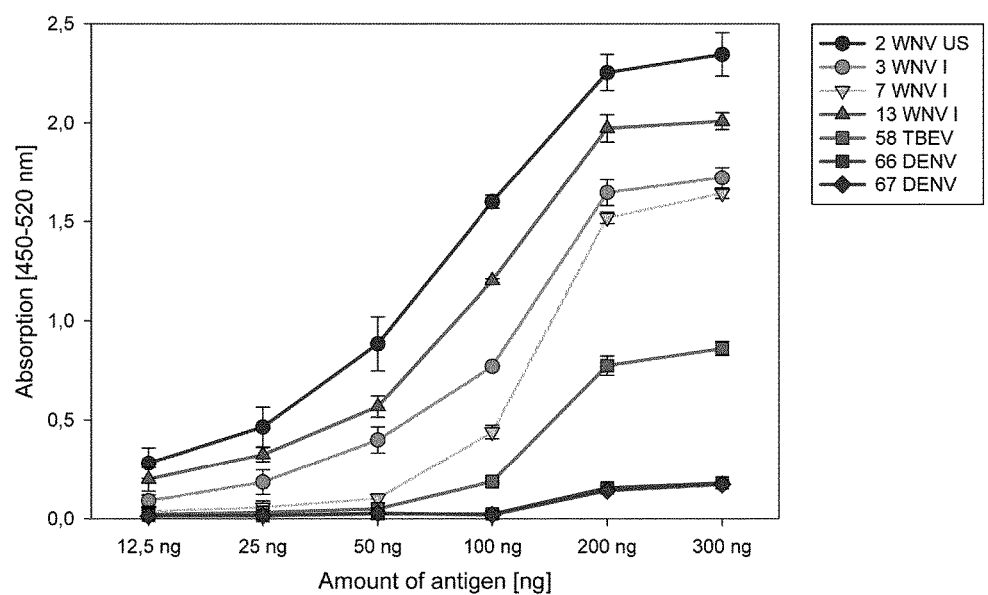
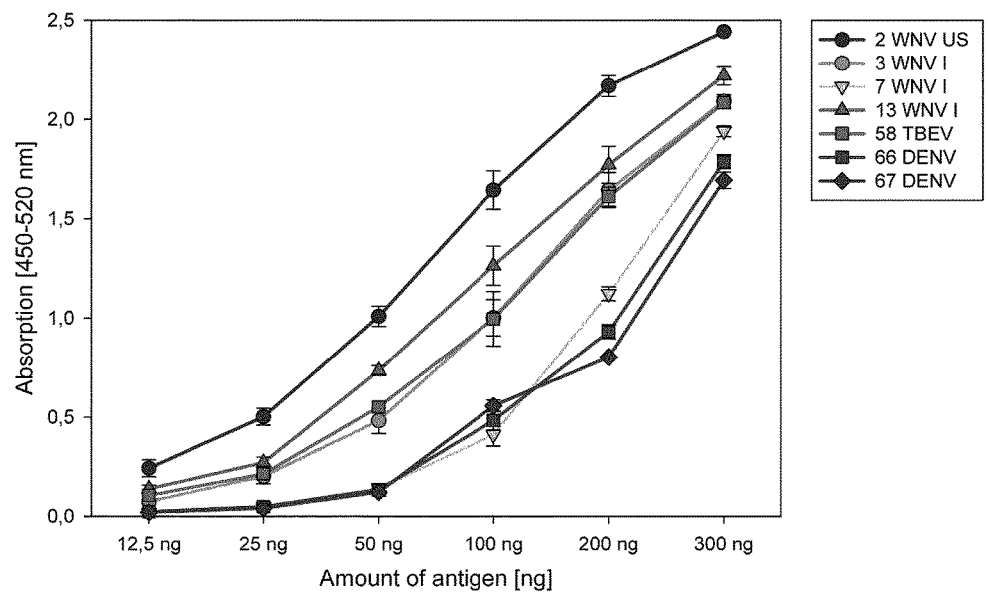

Figure 5
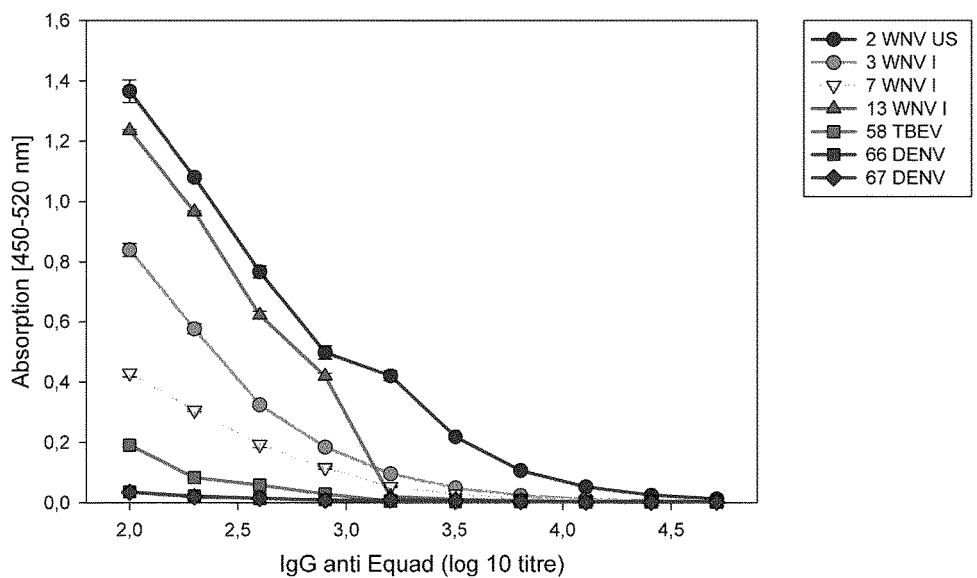
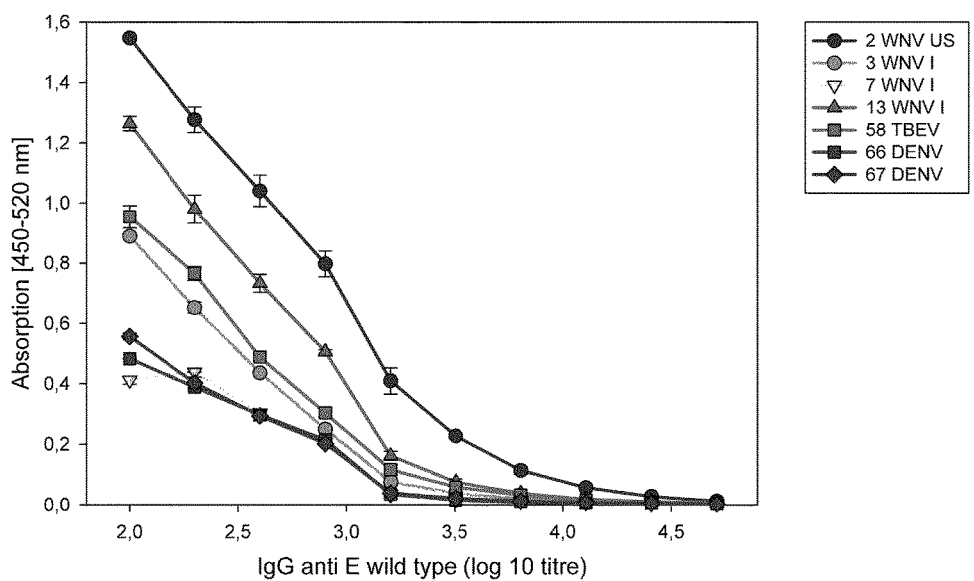

Figure 7 (continued)

C

```
                    A0              B0          C0              D0                          a
              1              10            20          30          40          50            60
WNV     FNCLGMSNRDFLEGVSGATWVDLVLEGDSCVTIMSKDKPTIDVKMMNMEAANLAEVRSYCYLA
DEN2    MRCIGISNRDFVEGVSGGSWVDIVLEHGSCVTTMAKNKPTLDFELIKTEAKQPATLRKYCIEA
DEN3    MRCVGVGNRDFVEGLSGATWVDVVLEHGGCVTTMAKNKPTLDIELQKTEATQLATLRKLCIEG
TBEV    SRCTHLENRDFVTGTQGTTRVTLVLELGGCVTITAEGKPSMDVWLDAIYQENPAKTREYCLHA b                                               d
                    E0                                                              
              70            80          90          100         110         120
WNV     TVSDLSTKAACPTMGEAHNDKRADPAFVCRQGVVDRGWGNGCGLFGKGSIDTCAKFACS..TK
DEN2    KLTNTTTESRCPTQGEPTLNEEQDKRFVCKHSMVDRGWGNGCGLFGKGGIVTCAMFTCK..KN
DEN3    KITNITTDSRCPTQGEAILPEEQDQNYVCKHTYVDRGWGNGCGLFGKGSLVTCAKFQCL..ES
TBEV    KLSDTKVAARCPTMGPATLAEEHQGGTVCKRDQSDRGWGNHCGLFGKGSIVACVKAACEAKKK

αA'                      F0            G0        H0
                                                     ▼
              130       140         150         160         170         180
WNV     AIGRTILKENIKYEVAIFVHGPTTVESHGNYSTQVGATQAGRFSITPAAPSYTLKLGEYGEVT
DEN2    MEGKIVQPENLEYTVVITPHSGEEHAV.GNDT....GKHGKEVKITPQSSITEAELTGYGTVT
DEN3    IEGKIVQHENLKYTVIITVHTGDQHQV.GNET......QGVTAEITSQASTAEAILPEYGTLG
TBEV    ATGHVYDANKIVYTVKVEPHTGDYVAA..NET....HSGRKTASFTISSEKTILTMGEYGDVS g           αA        'h'
              190         200         210         220         230         240
WNV     VDCEPRSGIDTNAYYMTVGT.......KTFLVHREWFMDLNLPWSSAG...STVWRNRETLME
DEN2    MECSPRTGLDFNEMVLLQMKD......KAWLVHRQWFLDLPLPWLPGADTQGSNWIQKETLVT
DEN3    LECSPRTGLDFNEMILLTMKD......KAWMVHRQWFFDLPLPWTSGATTKTPTWNRKELLVT
TBEV    LLCRVASGVDLAQTVILELDKTVEHLPTAWQVHRDWFNDLALPWKHEG...AQNWNNAERLVE
```

Figure 7 (continued)

```
                                         αB              k'      l                                           10
WNVE   ──────────────────────────────────────────────────▭──────────▶═══════════════════════────────────
              250       260       270       280       290       300
WNV    FEEPHATKQSVIALGSQEGALHQALAGAIPVEFSSNTVKLTS.GHLKCRVKMEKLQLKGTTYG
DEN2   FKNPHAKKQDVVVLGSQEGAMHTALTGATEIQMSSGNL.LFT.GHLKCRLRMDKLQLKGMSYS
DEN3   FKNAHAKKQEVVVLGSQEGAMHTALTGATEIQTSGGTS.IFA.GHLKCRLKMDKLKLKGMSYA
TBEV   FGAPHAVKMDVYNLGDQTGVLLKALAGVPVAHIEGTKY.HLKSGHVTCEVGLEKLKMKGLTYT

A              B           C                           D'
WNVE   ════════════════──────═══════════════──────════════════════─────────────────
              310       320       330       340       350       360
WNV    VCSK.AFKFLGTPADTGHGTVVLELQYTGTDGPCKVPISSVASLNDLTPVGRLVTVNPFVSVA
DEN2   MCTG.KFKVVKEIAETQHGTIVIRVQYEGDGSPCKIPFEIMDLEKR.HVLGRLITVNPIVTE.
DEN3   MCLN.TFVLKKEVSETQHGTILIKVEYKGEDAPCKIPFSTEDGQGK.AGNGRLITANPVVTK.
TBEV   MCDKTKFTWKRAPTDSGHDTVVMEVTFSGT.KPCRIPVRAVAHGSPDVNVAMLITPNPTIEN.

E         F           G
WNVE   ════════════─────═════════─────════════════
              370       380       390       400
WNV    TANAKVLIELEPPFGDSYIVVGRGEQQINHHWHKS
DEN2   .KDSPVNIEAEPPFGDSYIIIGVEPGQLKLNWFKK
DEN3   .KEEPVNIEAEPPFGESNIVIGIDKALKINWYRK
TBEV   ..NGGGFIEMQLPPGDNIIYVG....ELSHQWFQK
```

DISTINGUISHING FLAVIVIRUS INFECTION USING A RECOMBINANT MUTANT ENVELOPE PROTEIN

CROSS-REFERENCES TO RELATED APPLICATIONS

This application is a national stage application, filed under 35 U.S.C. § 371, of International Application No. PCT/EP2014/067912, filed on Aug. 22, 2014, and claims the benefit of and priority to European Patent Application No. 14160442.1, filed Mar. 18, 2014, the content of each of which is incorporated herein by reference in its entirety and for all purposes.

SEQUENCE LISTING

The instant application contains a Sequence Listing which has been submitted via EFS-Web. The content of the text file named "49839_504N01US_ST25.txt", which was created on Dec. 18, 2017 and is 73.5 KB in size, is hereby incorporated by reference in its entirety.

The present invention relates to mutant peptides of the E protein of the West Nile virus and other flaviviruses useful for discriminating flaviviral infections, as well as kits, methods and uses related thereto.

BACKGROUND

West Nile Virus (WNV) is an emerging mosquito-transmitted flavivirus that continues to spread and cause disease throughout several parts of the world, including Europe and the Americas. Specific diagnosis of WNV infections using current serological testing is complicated by the high degree of cross-reactivity between antibodies against other clinically relevant flaviviruses, including dengue, tick-borne encephalitis (TBEV), Japanese encephalitis (JEV), and yellow fever (YFV) viruses. Cross-reactivity is particularly problematic in areas where different flaviviruses co-circulate or in populations that have been immunized with vaccines against TBEV, JEV, or YFV. The majority of cross-reactive antibodies against the immunodominant flavivirus envelope (E) protein target a conserved epitope in the fusion loop at the distal end of domain II.

Methods:

We tested a loss-of-function bacterially expressed recombinant WNV E protein containing mutations in the fusion loop and an adjacent loop domain as a possible diagnostic reagent. By comparing the binding of sera from humans infected with WNV or other flaviviruses to the wild type and the mutant E proteins, we analyzed the potential of this technology to specifically detect WNV antibodies.

Results:

Using this system, we could reliably determine WNV infections. Antibodies from WNV-infected individuals bound equally well to the wild type and the mutant protein. In contrast, sera from persons infected with other flaviviruses showed significantly decreased binding to the mutant protein. The data have important implications for the development of improved, specific serological assays for the detection of WNV antibodies in regions where other flaviviruses co-circulate or in populations that are immunized with other flavivirus vaccines.

Keywords:

West Nile virus, diagnosis, antibodies, envelope protein

BACKGROUND

The mosquito-transmitted West Nile Virus (WNV) belongs to the Flaviviridae family of positive stranded RNA viruses, which also includes other arthropod-borne viruses such as dengue (DENV), tick borne encephalitis (TBEV), Japanese encephalitis (JEV), and yellow fever (YFV) viruses. WNV circulates in nature between mosquitoes and birds, but humans and other mammals also can be infected. In humans, about twenty percent of infected individuals develop flu-like symptoms, whereas in a subset of patients, primarily the elderly and immunocompromised, severe and sometimes fatal neurological complications can develop [1]. WNV was first isolated in Africa and later found to circulate in Asia, Australia, and sporadically in Europe. WNV was introduced into the United States in 1999 and rapidly spread throughout the Americas in the ensuing decade [2]. In addition, WNV has become endemic in several Southern and Eastern European countries during the past five years [3-6].

Several genetic lineages of WNV exist, and most isolates belong either to lineage 1 or lineage 2. Whereas in the Americas only WNV strains belonging to lineage 1 have been identified, in Europe strains of lineages 1 and 2 are circulating, sometimes even in the same area [7, 8].

WNV infections can be diagnosed by directly detecting the viral RNA, or by measuring antibodies produced against it in serum or cerebrospinal fluid (CSF). As viremia is transient, of low magnitude, and often precedes clinical manifestations, RNA detection can be challenging. In comparison, IgM antibodies are produced approximately 4 to 7 days after infection and IgG antibodies appear a few days later [9]. Therefore, antibody-based detection systems, such as ELISAs or indirect immunofluorescence tests, are commonly used for WNV diagnosis. However, a limitation of serological diagnosis for WNV infection is the structural similarity of the immunodominant envelope (E) protein among Flavivirus genus members. Antibodies produced against the E protein can be cross-reactive, leading to false-positive test results [10-12]. This problem occurs in many parts of the world due to co-circulation of different flaviviruses and historical vaccination with live attenuated or inactivated TBEV, JEV, or YFV vaccines. In Europe, cross-reactivity of antibodies against TBEV and WNV has been observed, especially in countries where TBEV vaccination is common [13]. Consequently, positive results obtained with the existing methods must be confirmed by lower-throughput virus neutralization tests, which require high-security and biosafety laboratories, which adds to the expense of the testing and delay in establishing a diagnosis [14].

Previous work has established that cross-reactive antibodies target the highly conserved fusion loop of the flavivirus E protein [15]. Moreover, binding of such cross-reactive antibodies can be diminished by inserting mutations into this epitope in the E protein or in virus-like particles (VLPs) [16-20]. Here, using bacterially expressed wild type or loss-of-function mutant WNV E proteins, we evaluated the binding of antisera derived from humans infected with different flaviviruses. This assay allowed us to determine rapidly and reliably WNV infections.

Methods

Antigens

The WNV E ectodomain (amino acid residues 1 to 404) and the quadruple mutant (T76A, M77G, W101R, L107R) of the New York 1999 strain (Acc. Nr. FJ151394) were expressed from the pET21a plasmid in *Escherichia coli*, and purified after an oxidative refolding protocol, as described previously [20,21]. The proteins were isolated as a monodispersed peak on a Superdex 75 or 200, 16/60 size-exclusion column using fast-protein liquid chromatography (GE Healthcare).

Serum Samples

Serum samples from confirmed WNV-infections (described in [22]) were obtained during outbreaks in Italy and Greece in 2010. The Italian samples (University of Padova, Italy) were derived from seroprevalence studies, blood donors or patients with West Nile neuroinvasive disease. The Greek samples (University of Thessaloniki, Greece) were obtained from patients with neuroinvasive disease, taken during the acute phase of illness (3-17 days). WNV infections were confirmed by virus neutralization tests. In addition, two WNV-positive samples were obtained from Seracare (USA). Serum samples from Canada were obtained from patients with confirmed WNV-specific T-cell responses [21]. None of the patients was vaccinated against other flaviviruses or had a recent travel history to other countries endemic for WNV. Serum samples from JEV-vaccinated individuals were obtained from the Robert-Koch Institute (Berlin, Germany). Sera from confirmed TBEV and DENV-infected individuals and negative controls were obtained from Padova University Hospital (Italy). All confirmed DENV cases were international travellers returning from endemic countries with diagnosis of recent primary DENV infection and with laboratory tests positive for IgM/IgG or IgG against only DENV. Confirmed TBEV IgG-positive serum samples were selected from a seroprevalence study in forest rangers. The TBEV IgG-positive samples were from subjects vaccinated against TBEV or with a history of confirmed TBEV infection. The neutralizing titer for WNV was negative in all of these cases (data not shown). Ethical approval was obtained from the Padova University Hospital ethics committee. All persons provided written consent.

Antibodies against DENV were detected by using DENV IgG and IgM capture DxSelect (Focus Diagnostics, Cypress, Calif., USA). Antibodies against TBEV were tested by using anti-TBE Virus IgG, IgM Enzygnost® ELISA (Siemens Healthcare, Germany).

Antibody Measurements

Nunc polysorb plates (Thermo Scientific, Germany) were coated overnight with indicated amounts of recombinant E ectodomain protein or E-quadruple mutant (in coating buffer (15 mM $Na_2CO_3$, 35 mM $NaHCO_3$ pH 9.6)) per well with gentle agitation at 4° C. The plates were washed three times with 350 µL per well of PBS/Tween (0.05%), followed by blocking with 5% non-fat dry milk powder (200 µL per well) for 2 h at room temperature (RT). After a second wash step, human sera (dilution 1:100 in 5% non-fat dry milk powder, 100 µL per well) were incubated for 1.5 h at RT. The sera were removed by a third wash step and 100 µL of the secondary antibody (1:10.000 diluted HRP-conjugated Goat-anti-Human IgG (Fisher Scientific)) was added for 1 h at RT. After washing, the TMB-substrate (BioLegend, Germany) was added to the wells and the plate was incubated for 30 min at RT in darkness. To stop the reaction, 1M $H_2SO_4$ was added, followed by measurement at 450 nm and 520 nm (reference wavelength) in an ELISA Reader (Infiniti M200, Tecan). All antibody tests were performed in duplicates in at least two independent experiments.

Equal loading of wild type and mutant E protein was verified using the humanized E16 monoclonal antibody (dilution 1:1000), which targets an epitope on domain III of the E protein, distant from the fusion loop [23] (data not shown).

Statistical Analysis

Statistical analysis was performed using Mann-Whitney Rank Sum Test in SigmaStat.

Results and Discussion

To analyze the influence of the E protein fusion loop on the specificity of anti-flavivirus IgG antibody binding to the E protein, we used a bacterially expressed wild type E-protein and a loss-of-function mutant (Equad), which contains four mutations within and proximal to the fusion loop [20] (FIG. 1). Both proteins were incubated with sera from humans infected with WNV from outbreaks in Europe and America. Although the overall signal strength varied substantially between individuals, all samples showed clearly detectable signals that did not differ markedly between the wild type and the mutant E-proteins (FIG. 2). Binding was similar in sera from patients infected with WNV strains belonging to genetic lineage 1 or lineage 2 [24], as demonstrated by signals obtained with sera from the United States, Canada or Italy (lineage 1) and Greece (lineage 2). Next, the assay was evaluated for its specificity by testing sera from humans containing antibodies against the heterologous flaviviruses, TBEV and DENV. In contrast to the WNV-positive samples, we observed statistically significant differences in binding between the wild-type and quadruple mutant E proteins (FIG. 3). Most samples showed the expected strong cross-reactivity, with high binding to wild type WNV E; however, the values for binding of the heterologous sera to the fusion loop mutant were substantially lower. Although some DENV-infected sera showed binding to the mutant WNV E protein, the values obtained with the wild type E protein were all significantly higher.

To assess the relative amount of antibody against wild type and mutant E proteins, sera from WNV-, TBEV- or DENV-infected individuals were incubated with increasing amounts of the two protein antigens in the solid phase. For the WNV-positive sera, the signal for binding the Equad mutant saturated at ~200 ng per well (FIG. 4). In contrast, saturation was not observed with the wild type protein until 300 ng of protein was added. This possibly reflects the limiting amount of WNV-specific antibodies that target other non-fusion loop epitopes. Increasing the antigen amount from 50 ng to 100 ng resulted in enhanced detection of sera, especially for those showing moderate binding at the lower amounts, as exemplified by WNV serum 7 (see FIG. 2), but increased the background binding of some samples (data not shown). Serum dilution assays confirmed the marked differences in titers against the mutant and the wild type E protein shown by the DENV- and TBEV positive sera (FIG. 5).

By calculating the average ratios between the signal for the wild-type and mutant protein in FIGS. 1 and 2, a value could be assigned for each of the flaviviruses, which distinguished their pattern of reactivity. For WNV, the average ratio was 1.22 (standard deviation (SD) of 0.2), for DENV 5.92 (SD of 3.1) and for TBEV 6.06 (SD of 2.1), with a statistically significant difference between WNV and the other two infections (P=0.005, Mann-Whitney Rank Sum Test).

To analyze the suitability of this system to discriminate between infections with different flaviviruses of the JEV-serocomplex, we analysed sera from individuals vaccinated against JEV. Due to the low antibody titres in these sera 100 ng of antigen per well were required. Similar to the DENV and TBEV infections, in all samples there was decreased binding to the Equad antigen compared to the wild-type E protein. However, under the conditions used, the differences were less pronounced and not statistically significant when compared to the WNV samples, a finding which is not unexpected given the higher amino acid sequence identity (approx. 80%) of the WNV E-protein to JEV as compared to TBEV or DENV (approx. 40% and 50%, respectively). This indicates that the principle of discrimination also applies to JEV, but the definition of average ratios will require more refinement for WNV-related viruses from the same JEV serocomplex.

In summary, we present a new assay for the serologic diagnosis of WNV infections, which is based on the relative difference in antibody binding to mutant and wild type E protein of WNV. The data suggest that defined values could be established that allow the differentiation of flavivirus infections. The observation that antibody binding to the E protein varied substantially among WNV-infected individuals is consistent with previous observations describing the heterogeneity of the human humoral immune response to WNV infections [22, 25]. However, for WNV, there were no significant differences observed between the binding towards wild type and mutant E protein, unless the antigens were present at high density. Because the human antibody response against WNV is skewed towards non-neutralizing epitopes including the fusion loop [21, 26], some difference in binding was expected. However, DENV- and TBEV-positive sera show a more pronounced difference in the binding to wild type and mutant E protein, which reflects the immunodominance of the fusion-loop epitope as a cross-reactive determinant [18, 27-29]. Although diminished binding of cross-reactive DENV-infected sera using a similar Equad protein has been shown previously [20], sera from WNV- and TBEV infected patients were not analyzed in that study. The quadruple mutant contains four mutations adjacent to and within the fusion loop of the protein, which impact the binding of cross-reactive flavivirus antibodies. Using a VLP-based system, Roberson et al. [19] analyzed a double-mutant (G106R and L107H) in the fusion loop of the E protein for WNV diagnosis. Our approach differs in number and positions of the mutations and in the antigen platform. A recombinant bacteria-derived protein has the advantage over mammalian cell-culture derived VLPs as it can be produced rapidly, inexpensively, and in higher yield, and likely can be quantified more precisely for diagnostic applications.

Therefore, our results may be useful for the development of a specific rapid diagnostic test for the detection of WNV IgG and possibly, IgM antibodies. IgM detection would be particularly useful for the investigation of recent infections. This assay can be used to measure IgM antibodies, by simply changing the secondary antibody or generating an IgM-capture assay. Alternatively, a recent infection can also be diagnosed by measuring a rise in IgG antibody titers over time [11].

In addition, the principle described herein can be applied to other flavivirus infections (e.g. DENV, YFV, TBEV, JEV, USUV) and is not limited to WNV.

Conclusions

By using a recombinant loss-of-function mutant of the WNV E-protein, infections with WNV can be discriminated from those with TBEV and DENV based on antibody measurements. Whereas under the conditions used no substantive difference in binding of WNV antibodies to the wild type or mutant E protein was observed, anti-TBEV or -DENV antibodies bound significantly less well to the mutant protein lacking the cross-reactive fusion loop epitope.

REFERENCES

[1] Hayes E B, Sejvar J J, Zaki S R, Lanciotti R S, Bode A V, Campbell G L: Virology, pathology, and clinical manifestations of West Nile virus disease. Emerg Infect Dis 2005, 11:1174-1179.

[2] Murray K O, Mertens E, Despres P: West Nile virus and its emergence in the United States of America. Vet Res 2010, 4: 67.

[3] Barzon L, Pacenti M, Franchin E, Lavezzo E, Martello T, Squarzon L, Toppo S, Fiorin F, Marchiori G, Russo F, Cattai M, Cusinato R, Palu G: New endemic West Nile virus lineage 1a in northern Italy, July 2012. Euro Surveill 2012: 17.

[4] Sirbu A, Ceianu C S, Panculescu-Gatej R I, Vazquez A, Tenorio A, Rebreanu R, Niedrig M, Nicolescu G, Pistol A.: Outbreak of West Nile virus infection in humans, Romania, July to October 2010. Euro Surveill 2011; 16

[5] Sambri V, Capobianchi M, Charrel R, Fyodorova M, Gaibani P, Gould E, Niedrig M, Papa A, Pierro A, Rossini G, Varani S, Vocale C, Landini M P: West Nile virus in Europe: emergence, epidemiology, diagnosis, treatment, and prevention. Clin Microbiol Infect 2013, 8:699-704.

[6] Papa A: West Nile virus infections in Greece: an update. Expert Rev Anti Infect Ther 2012, 10:743-750.

[7] Magurano F, Remoli M E, Baggieri M, Fortuna C, Marchi A, Fiorentini C, Bucci P, Benedetti E, Ciufolini M G, Rizzo C, Piga S, Salcuni P, Rezza G, Nicoletti L: Circulation of West Nile virus lineage 1 and 2 during an outbreak in Italy. Clin Microbiol Infect 2012, 18: E545-547.

[8] Barzon L, Pacenti M, Franchin E, Squarzon L, Lavezzo E, Cattai M, Cusinato R, Palù, G:
The complex epidemiological scenario of West Nile virus in Italy. Int J Environ Res Public Health. 2013, 10:4669-4689.

[9] Diamond M S, Mehlhop E, Oliphant T, Samuel M A: The host immunologic response to West Nile encephalitis virus. Front Biosci 2009, 14:3024-3034.

[10] Papa A, Karabaxoglou D, Kansouzidou A: Acute West Nile virus neuroinvasive infections: cross-reactivity with dengue virus and tick-borne encephalitis virus. J Med Virol 2011, 83:1861-1865.

[11] Sambri V, Capobianchi M R, Cavrini F, Charrel R, Donoso-Mantke O, Escadafal C, Franco L, Gaibani P, Gould E A, Niedrig M, Papa A, Pierro A, Rossini G, Sanchini A, Tenorio A, Varani S, Vázquez A, Vocale C Zeller H: Diagnosis of west nile virus human infections: overview and proposal of diagnostic protocols considering the results of external quality assessment studies. Viruses 2013, 5: 2329-2348.

[12] Sanchini A, Donoso-Mantke O, Papa A, Sambri V, Teichmann A, Niedrig M: Second international diagnostic accuracy study for the serological detection of West Nile virus infection. PLoS Negl Trop Dis 2013, 7:e2184

[13] Donoso-Mantke O, Karan L S, Ruzek D: Tick-Borne Encephalitis Virus: A General Overview, In *Flavivirus Encephalitis*, Edited by Daniel Ruzek, ISBN: 978-953-307-669-0, InTech, 2011.

[14] Maeda A, Maeda J: Review of diagnostic plaque reduction neutralization tests for flavivirus infection. Vet J 2013 1:33-40.

[15] Crill W D, Chang G J: Localization and characterization of flavivirus envelope glycoprotein cross-reactive epitopes. J Virol. 2004, 78:13975-13986.

[16] Diamond M S, Pierson T C, Fremont D H: The structural immunology of antibody protection against West Nile virus. Immunol Rev 2008, 225:212-225 [17] Chiou S S, Crill W D, Chen L K, Chang G J: Enzyme-linked immunosorbent assays using novel Japanese encephalitis virus antigen improve the accuracy of clinical diagnosis of flavivirus infections. Clin Vaccine Immunol 2008, 15:825-35.

[18] Crill W D, Trainor N B, Chang G J: A detailed mutagenesis study of flavivirus cross-reactive epitopes using West Nile virus-like particles. J Gen Virol 2007, 88:1169-74.

[19] Roberson J A, Crill W D, Chang G J: Differentiation of West Nile and St. Louis encephalitis virus infections by use of noninfectious virus-like particles with reduced cross-reactivity. J Clin Microbiol 2007, 10:3167-74.

[20] Vogt M R, Dowd K A, Engle M, Tesh R B, Johnson S, Pierson T C, Diamond M S: Poorly neutralizing cross-reactive antibodies against the fusion loop of West Nile virus envelope protein protect in vivo via Fcgamma receptor and complementdependent effector mechanisms. J Virol 2011, 85:11567-11580.

[21] Oliphant T, Nybakken G E, Austin S K, Xu Q, Bramson J, Loeb M, Throsby M, Fremont D H, Pierson T C, Diamond M S: Induction of epitope-specific neutralizing antibodies against West Nile virus. J Virol 2007, 81:11828-11839.

[22] Chabierski S, Makert G R, Kerzhner A, Barzon L, Fiebig P, Liebert U G, Papa A, Richner J M, Niedrig M, Diamond M S, Palù, G, Ulbert S: Antibody Responses in Humans Infected with Newly Emerging Strains of West Nile Virus in Europe. PlosOne 2013, 8:e66507

[23] Nybakken G E, Oliphant T, Johnson S, Burke S, Diamond M S, Fremont D H: Structural basis of West Nile virus neutralization by a therapeutic antibody. Nature 2005, 437: 764-769.

[24] Lanciotti R S, Ebel G D, Deubel V, Kerst A J, Murri S, Meyer R, Bowen M, McKinney N, Morrill W E, Crabtree M B, Kramer L D, Roehrig J T.: Complete genome sequences and phylogenetic analysis of West Nile virus strains isolated from the United States, Europe, and the Middle East. Virology 2002, 298: 96-105.

[25] Faggioni G, Pomponi A, De Santis R, Masuelli L, Ciammaruconi A, Monaco F, Di Gennaro A, Marzocchella L, Sambri V, Lelli R, Rezza G, Bei R, Lista F.: West Nile alternative open reading frame (N-NS4B/WARF4) is produced in infected West Nile Virus (WNV) cells and induces humoral response in WNV infected individuals. Virol J 2013, 22:283.

[26] Throsby M, Geuijen C, Goudsmit J, Bakker A Q, Korimbocus J, Kramer R A, Clijsters-van der Horst M, de Jong M, Jongeneelen M, Thijsse S, Smit R, Visser T J, Bijl N, Marissen W E, Loeb M, Kelvin D J, Preiser W, ter Meulen J, de Kruif J.: Isolation and characterization of human monoclonal antibodies from individuals infected with West Nile Virus. J Virol 2006, 80:6982-6992.

[27] Smith S A, de Alwis A R, Kose N, Harris E, Ibarra K D, Kahle K M, Pfaff J M, Xiang X, Doranz B J, de Silva A M, Austin S K, Sukupolvi-Petty S, Diamond M S, Crowe J E Jr.: The Potent and Broadly Neutralizing Human Dengue Virus-Specific Monoclonal Antibody 1C19 Reveals a Unique Cross-Reactive Epitope on the be Loop of Domain II of the Envelope Protein. MBio 2013, 4.

[28] Tsai W Y, Lai C Y, Wu Y C, Lin H E, Edwards C, Jumnainsong A, Kliks S, Halstead S, Mongkolsapaya J, Screaton G R, Wang W K: High-avidity and potently neutralizing cross-reactive human monoclonal antibodies derived from secondary dengue virus infection. J Virol 2013, 87:12562-12575.

[29] Beltramello M, Williams K L, Simmons C P, Macagno A, Simonelli L, Quyen N T, Sukupolvi-Petty S, Navarro-Sanchez E, Young P R, de Silva A M, Rey F A, Varani L, Whitehead S S, Diamond M S, Harris E, Lanzavecchia A, Sallusto F: The human immune response to Dengue virus is dominated by highly cross-reactive antibodies endowed with neutralizing and enhancing activity. Cell Host Microbe 2010, 8:271-283.

FIGURE LEGENDS

FIG. 1: Sequence alignment of fusion loop domain of E proteins from different flaviviruses, WNV E: West Nile virus wild type E-protein (SEQ ID No: 10), WNV-Equad: WNV E-quadruple mutant (point mutations are marked in red) (SEQ ID No: 11), TBEV-E: TBEV (SEQ ID No: 5), DENV: DENV E protein, serotypes 1-4 (SEQ ID Nos: 6-9). Amino acids positions of the full length protein are indicated in the top row.

FIG. 2: Analyses of WNV infected human sera on 50 ng per well of the microtiter plate of E wild type (grey columns) compared to the mutant Equad (black columns), sera from different areas, as indicated next to the numbers (G: Greece, I: Italy, C: Canada, US: USA).

FIG. 3: Comparison of IgG binding to 50 ng per well of wild type E (grey columns) and Equad (black columns) using negative (NEG), TBEV- or DENV-positive sera. Asterisks indicate statistically significant differences between wild type and mutant WNV-Envelope protein (TBEV: **, P=<0.001; DENV: *, P=0.010; Mann-Whitney Rank Sum Test)

FIG. 4: Antigen titration of Equad (A) and E wild type (B). Different sera were incubated with an increasing amount of recombinant proteins per well of the microtiter plate. Differences between individual sera at 300 ng of antigen were not statistically significant.

FIG. 5: Sera dilution curves using constant antigen amounts (100 ng) of the Equad mutant (A) and wild type E protein (B)

Figure 6:
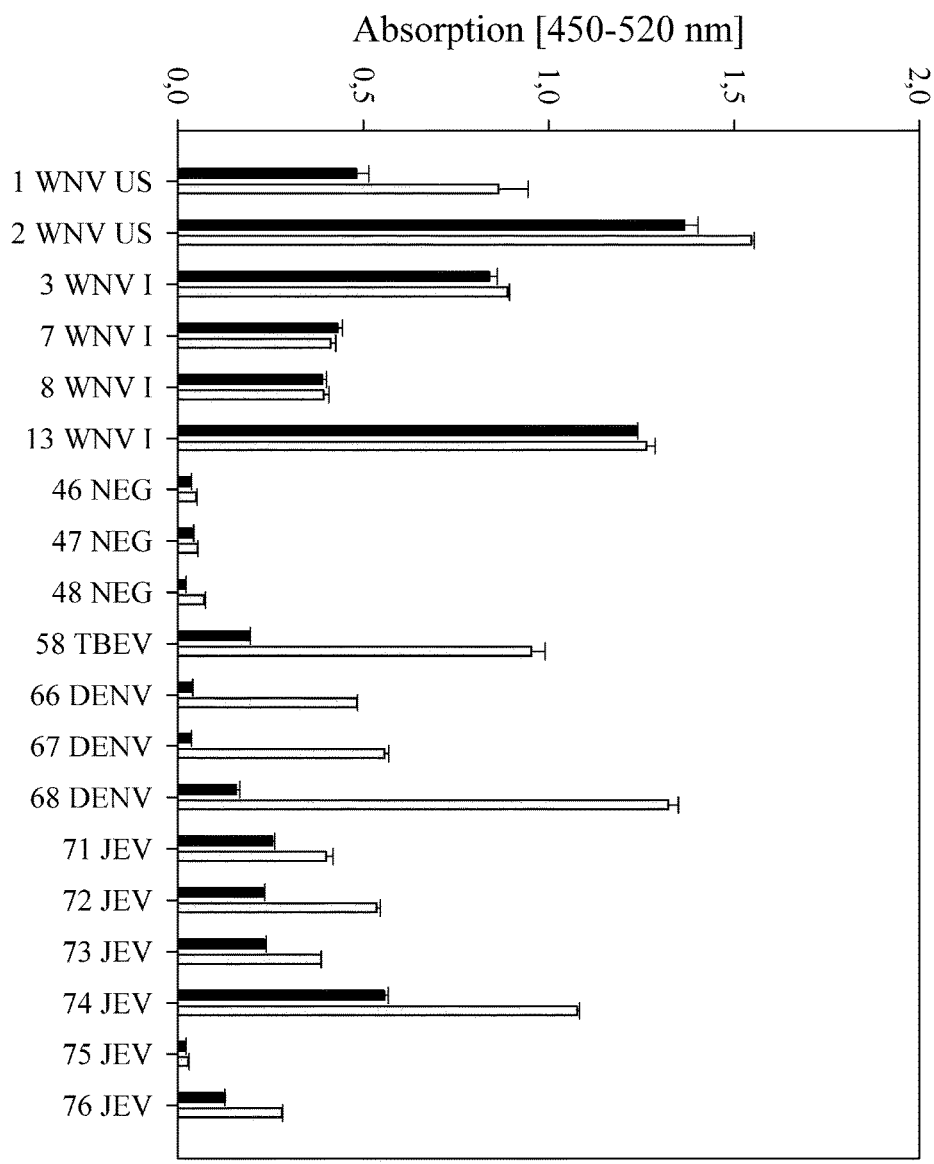

FIG. 6: Comparison of IgG binding to wild type E (grey columns) and Equad (black columns) using negative (NEG), WNV-, TBEV-, DENV- and JEV-positive sera.

Figure 7:
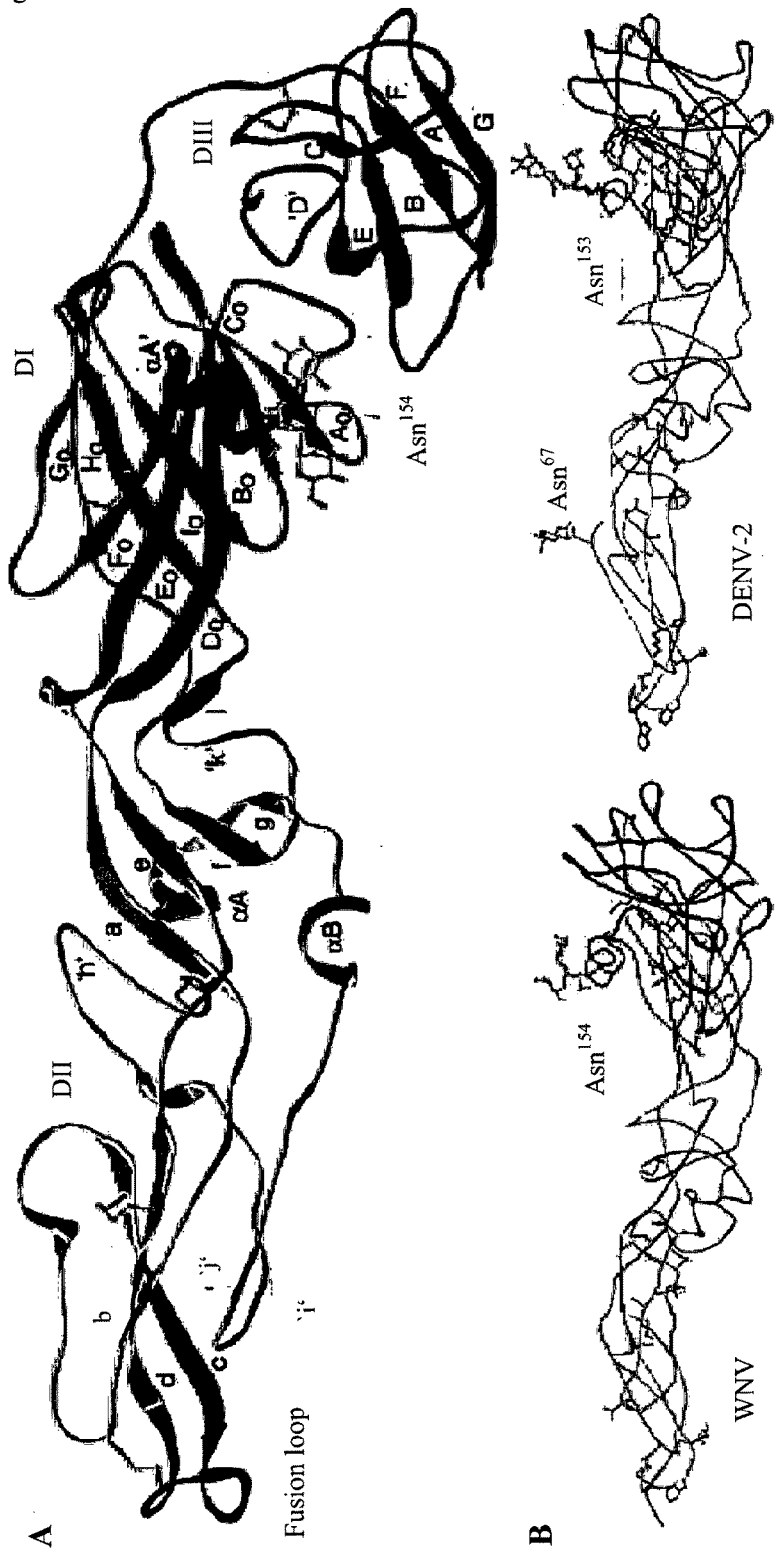

FIG. 7: Figure from Nybakken et al, 2006: Structure of WNV E protein. (A) DI, DII, and DIII of monomeric E adopt a topology typical of E proteins from other flaviviruses. The fusion loop (residues 98 to 110) is highlighted at the tip of DII. The carbohydrate on Asn154 of DI protrudes next to a novel a-helix. Disulfide bonds are shown in gold. (B) (Left) Tube representation of WNV E, with potential dimer contacts shown. (Right) Tube representation of DENV-2 E (1OAN), with known dimer contacts shown. (C) Structural alignment of E structures from WNV SEQ ID No: 22, DENV-2 SEQ ID No: 23, DENV-3 SEQ ID No: 24, and TBEV SEQ ID No: 25. Conservation and similarity are depicted in dark and light grey, respectively. The glycosylation site is marked with an inverted triangle. DIII starts at amino acid 298 and ends at the terminal amino acid of the ectodomain.

Figure 8:
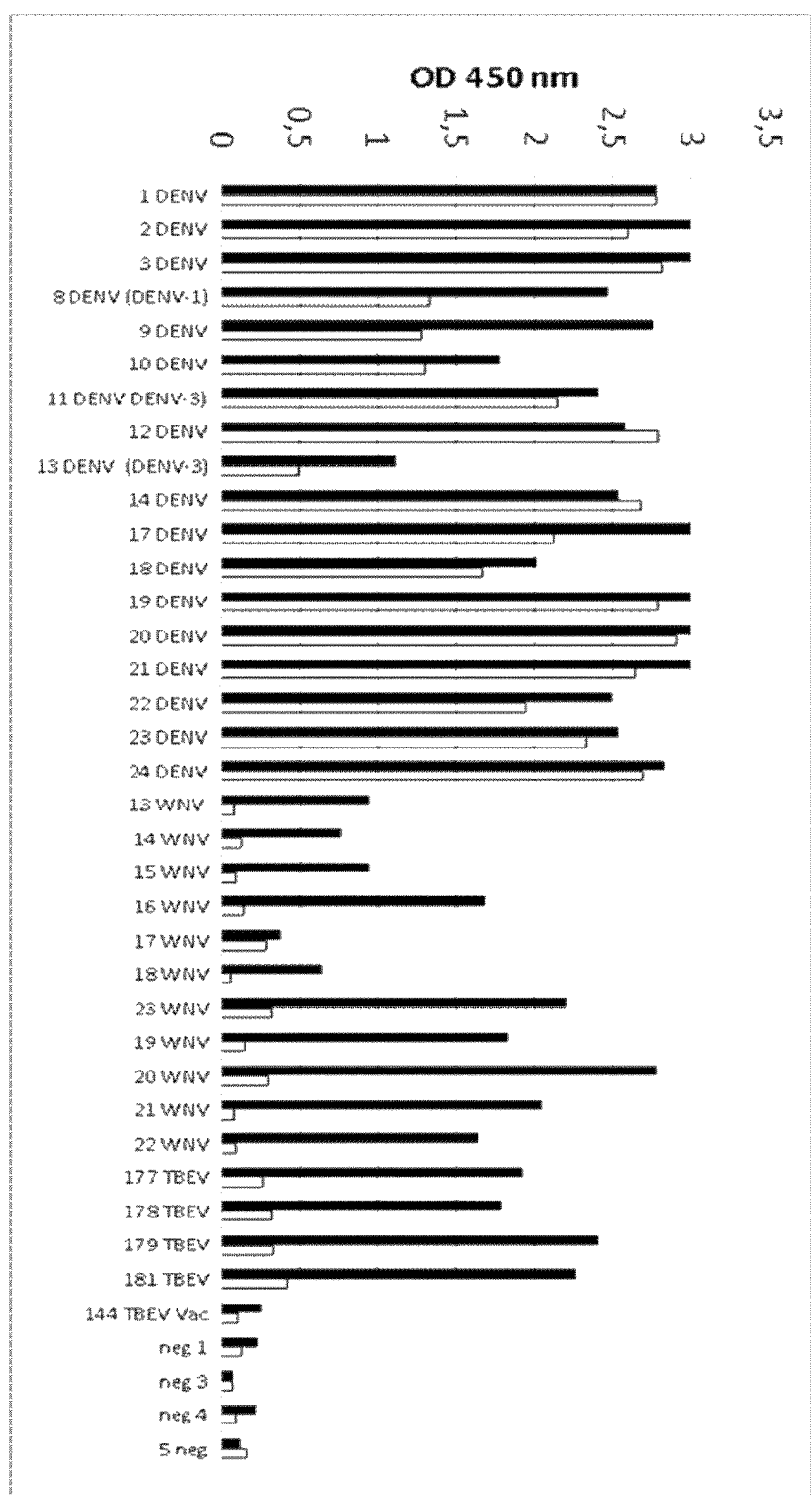

FIG. 8: human sera infected with DENV, WNV, TBEV or negative control sera were incubated with the ectodomain of wt DENV-2 E protein (black columns) and the quadruple mutant T76R, Q77E, W101R, L107R of the ectodomain of DENV-2 E protein (white columns).

Figure 9:
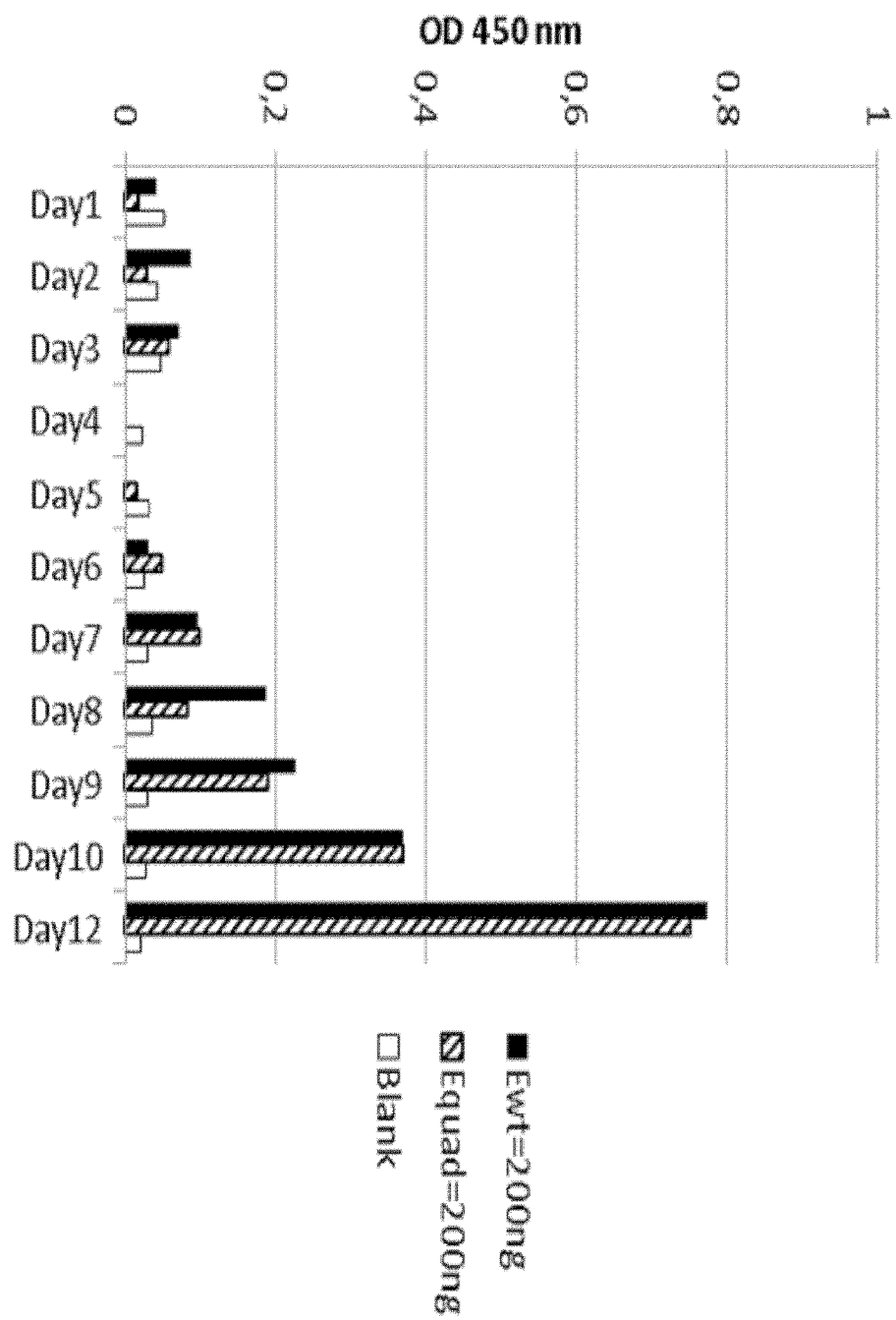

FIG. 9: Sera from a Rhesus macaque infected with WNV at day 0, analyzed for IgM binding on Ewt and Equad mutant at the indicated days after infection. Black columns: WNV E protein wt ectodomain, 200 ng; striped columns: human WNV E protein quadruple mutant T76A, M77G, W101R, L107R ectodomain; white columns: blank.

SEQUENCES

West Nile Virus New York 1999 strain: Acc. Nr. FJ151394

Ewt (amino acids 1-415 of WNV-NY-1999)
(SEQ ID No: 1)

FNCLGMSNRDFLEGVSGATWVDLVLEGDSCVTIMSKDK
PTIDVKMMNMEAVNLAEVRSYCYLATVSDLSTKAACPT
MGEAHNDKRADPAFVCRQGVVDRGWGNGCGLFGKGSI
DTCAKFACSTKAIGRTILKENIKYEVAIFVHGPTTVESHG
NYSTQVGATQAGRFSITPAAPSYTLKLGEYGEVTVDCEP
RSGIDTNAYYVMTVGTKTFLVHREWFMDLNLPWSSAGS
TVWRNRETLMEFEEPHATKQSVIALGSQEGALHQALAG
AIPVEFSSNTVKLTSGHLKCRVKMEKLQLKGTTYGVCSK
AFKFLGTPADTGHGTVVLELQYTGTDGPCKVPISSVASL
NDLTPVGRLVTVNPFVSVATANAKVLIELEPPFGDSYIVV
GRGEQQINHHWHKSGSSIGKAFTTTLKGA

Equad (mutations bold, underlined)
T76A, 89 M77G, W101R, L107R
(SEQ ID No: 2)

FNCLGMSNRDFLEGVSGATWVDLVLEGDSCVTIMSKDK
PTIDVKMMNMEAVNLAEVRSYCYLATVSDLSTKAACPA
GGEAHNDKRADPAFVCRQGVVDRGRGNGCGRFGKGSI
DTCAKFACSTKAIGRTILKENIKYEVAIFVHGPTTVESHG
NYSTQVGATQAGRFSITPAAPSYTLKLGEYGEVTVDCEP
RSGIDTNAYYVMTVGTKTFLVHREWFMDLNLPWSSAGS
TVWRNRETLMEFEEPHATKQSVIALGSQEGALHQALAG
AIPVEFSSNTVKLTSGHLKCRVKMEKLQLKGTTYGVCSK
AFKFLGTPADTGHGTVVLELQYTGTDGPCKVPISSVASL
NDLTPVGRLVTVNPFVSVATANAKVLIELEPPFGDSYIVV
GRGEQQINHHWHKSGSSIGKAFTTTLKGA

Equad ectodomain (mutations bold, underlined)
T76A, 89 M77G, W101R, L107R
(SEQ ID No: 3)

FNCLGMSNRDFLEGVSGATWVDLVLEGDSCVTIMSKDK
PTIDVKMMNMEAVNLAEVRSYCYLATVSDLSTKAACPA
GGEAHNDKRADPAFVCRQGVVDRGRGNGCGRFGKGSI
DTCAKFACSTKAIGRTILKENIKYEVAIFVHGPTTVESHG
NYSTQVGATQAGRFSITPAAPSYTLKLGEYGEVTVDCEP
RSGIDTNAYYVMTVGTKTFLVHREWFMDLNLPWSSAGS
TVWRNRETLMEFEEPHATKQSVIALGSQEGALHQALAG
AIPVEFSSNTVKLTSGHLKCRVKMEKLQLKGTTYGVCSK
AFKFLGTPADTGHGTVVLELQYTGTDGPCKVPISSVASL
NDLTPVGRLVTVNPFVSVATANAKVLIELEPPFGDSYIVV
GRGEQQINHHWHKSGSSI

-continued

Ewt ectodomain (amino acids 1-404 of WNV-NY-1999)
(SEQ ID No: 4)
FNCLGMSNRDFLEGVSGATWVDLVEGDSCVTIMSKDK

PTIDVKMMNMEAVNLAEVRSYCYLATVSDLSTKAACPT

MGEAHNDKRADPAFVCRQGVVDRGWGNGCGLFGKGSI

DTCAKFACSTKAIGRTILKENIKYEVAIFVHGPTTVESHG

NYSTQVGATQAGRFSITPAAPSYTLKLGEYGEVTVDCEP

RSGIDTNAYYVMTVGTKTFLVHREWFMDLNLPWSSAGS

TVWRNRETLMEFEEPHATKQSVIALGSQEGALHQALAG

AIPVEFSSNTVKLTSGHLKCRVKMEKLQLKGTTYGVCSK

AFKFLGTPADTGHGTVVLELQYTGTDGPCKVPISSVASL

NDLTPVGRLVTVNPFVSVATANAKVLIELEPPFGDSYIVV

GRGEQQINHHWHKSGSSI

Fusion loop domain of the wt E protein from West Nile Virus:
(SEQ ID No: 10; see FIG. 1)
ATVSDLSTKAACPTMGEAHNDKRADPAFVCRQGVVDRGWGNGCGLFGKGSIDTCAKFA Fusion loop domain of the T76A, 89 M77G, W101R, L107R mutant of the E
protein from West Nile Virus:
(SEQ ID No: 11; see FIG. 1)
ATVSDLSTKAACPAGGEAHNDKRADPAFVCRQGVVDRGRGNGCGRFGKGSIDTCAKFA Fusion loop domain of the wt E protein from TBEV Virus:
(SEQ ID No: 5; see FIG. 1)
AKLSDTKVAARCPTMGPATLAKEHQGGTVCKRDQSDRGWGNHCGLFGKGSIVACVKAA Fusion loop domain of the wt E protein from Dengue Virus, serotype 1:
(SEQ ID No: 6; see FIG. 1)
AKISNTTTDSRCPTQGEATLVEEQDANFVCRRTFVDRGWGNGCGLFGKGSLLTCAKFK Fusion loop domain of the wt E protein from Dengue Virus, serotype 2:
(SEQ ID No: 7; see FIG. 1)
AKLTNTTTESRCPTQGEPSLVEEQDKRFVCRHSMVDRGWGNGCGLFGKGGIVTCAMFT Fusion loop domain of the wt E protein from Dengue Virus, serotype 3:
(SEQ ID No: 8; see FIG. 1)
GKITNITTDSRCPTQGEAVLPEEQDQNYVCKHTYVDRGWGNGCGLFGKGSLVTCAKFQ Fusion loop domain of the wt E protein from Dengue Virus, serotype 4:
(SEQ ID No: 9; see FIG. 1)
ASISNITTATRCPTQGEPYLKEEQDQQYICRRDVVDRGWGNGCGLFGKGGVVTCAKFA As shown in the examples, specifically mutating positions 76, 77, 101, and 107 of the E protein of WNV as follows: T76A, M77G, W101R, L107R, results in a mutated E protein which is surprisingly useful for discriminating between WNV infection and other flavivirus infections. This allows for the first time to reliably and rapidly determine WNV infections in a serological assay.

In one embodiment, the present invention relates to a mutant peptide corresponding to the T76A, M77G, W101R, L107R quadruple mutant of the E protein of the West Nile Virus (WNV).

The E protein of West Nile Virus (WNV) is well known to a skilled person and corresponds to the envelope protein of WNV. In particular, amino acids 1-415 of the wildtype E protein of West Nile Virus New York 1999 strain are shown in SEQ ID No: 1. In a further preferred embodiment, the E protein of WNV is an E protein of a lineage 2 WNV, more preferably wherein the E protein comprises the sequence according to SEQ ID No: 20.

The WNV genome encodes 10 proteins, including three structural (capsid, premembrane [prM], and envelope [E]) and seven nonstructural (NS1, NS2A, NS2B, NS3, NS4A, NS4B, and NS5) proteins. These are translated as a single polypeptide, which is subsequently cleaved by viral and cellular proteases (see Nybakken G E et al; J Virol. December 2006; 80(23): 11467-11474). The initial step toward virion generation occurs when the 11-kb positive-strand RNA genome, in complex with capsid protein, buds through the endoplasmic reticulum membrane. A lipid envelope coats the nascent flavivirus particles and contains 180 molecules each of E and prM organized into 60 asymmetric trimeric spikes consisting of prM-E heterodimers. At the apices of the spikes, prM caps the fusion loop of E, presumably to prevent premature fusion as the virus passes through the acidic secretory pathway. A furin-catalyzed membrane-proximal cleavage releases the N-terminal prepeptide from prM (39, 44), initiating the transition from immature to mature virion.

Formation of the mature virion requires structural rearrangement of the E proteins from trimeric prM-E heterodimers into homodimeric rafts that smoothly cover the lipid membrane with quasi-icosahedral symmetry. The smooth, 500-A-diameter surface of the mature flavivirus differs from those of many other viruses (e.g., influenza virus, human immunodeficiency virus, and alphaviruses), as it lacks spikes or protrusions.

The E proteins of flaviviruses exhibit a three-domain architecture. The central β-barrel consisting of eight strands defines domain I (DI), an elongated domain containing the 13-residue fusion loop at one end defines domain II (DII), and the opposite end adopts an immunoglobulin (Ig)-like fold and is referred to as domain III (DIII) in literature (see FIG. 7, taken from Nybakken et al. (supra)). Domain I of the WNV E protein is an eight-stranded β-barrel in the center portion of the protein and is comprised of 127 amino acids (residues 1 to 51, 134 to 195, and 284 to 297). DII of the WNV E protein consists of 170 residues inserted into DI (residues 52 to 133 and 196 to 283). The distal end of DII contains the putative fusion loop (residues 98 to 110), a conserved glycine-rich, hydrophobic sequence. DIII of the WNV E protein is an Ig-like domain with seven β-strand at the C-terminal end of the ectodomain.

An ectodomain is preferably understood as a domain of a membrane protein that extends into the extracellular or extraviral space. In the WNV E protein, the ectodomain preferably corresponds to amino acids 1 to 404 of the E protein. A domain preferably forms a compact three-dimensional structure and often can be stable and folded independent from the remaining part of the whole protein.

The present mutant ectodomain peptides of the invention could be refolded successfully from inclusion bodies after bacterial expression, as shown in the examples.

A "peptide" is preferably understood as a linear chain of 10 to 500 amino acid monomers linked by peptide bonds. Preferably, the amino acid monomers are naturally occurring amino acids, more preferably naturally occurring L-amino acids. The peptides may be unmodified, or may contain modifications at the C-terminus, the N-terminus and/or side chains. For example, the peptides may be amidated and/or carboxylated at the termini. Suitable L-amino acids are: Glycine, Alanine, Valine, Leucine, Isoleucine, Serine, Cysteine, Threonine, Methionine, Proline, Phenylalanine, Tyrosine, Tryptophan, Histidine, Lysine, Arginine, Aspartate, Glutamate, Asparagine, and Glutamine. A preferred modification of a side chain is an S—S bond formed between two Cys residues.

A "quadruple mutant" peptide is preferably understood as mutant peptide which contains four mutations as compared to the corresponding wildtype peptide. Therefore, a quadruple mutant peptide differs from the corresponding wildtype peptide in four amino acids. "T76A" is preferably understood as that the T (threonine) residue at position 76 from the N terminus of the wildtype peptide is mutated to A (alanine).

Methods for introducing mutations in a peptide sequence are known in the art. For example, in case of recombinant expression, adequate primers and cloning procedures may be used to express such mutated peptide sequence. Alternatively, the peptides of the invention may be produced by chemical synthesis by methods known in the art.

In another embodiment, the present invention relates to a mutant peptide with the sequence of SEQ ID No: 2. This sequence corresponds to amino acids 1-415 of the E protein of WNV with the mutations T76A, M77G, W101R, L107R.

The mutant peptide of the example was designed based on the sequence of the West Nile Virus New York 1999 strain, which is found under GenBank accession number FJ151394. Therefore, in a preferred embodiment, the West Nile Virus is the West Nile Virus New York 1999 strain. In a further preferred embodiment, the West Nile Virus has the genome sequence according to accession number FJ151394.

In a further preferred embodiment, the West Nile Virus is of lineage 1 or lineage 2. Several genetic lineages of WNV exist, and most isolates belong either to lineage 1 or lineage 2. Whereas in the Americas only WNV strains belonging to lineage 1 have been identified, in Europe strains of lineages 1 and 2 are circulating, sometimes even in the same area. As shown in the Examples, WNV of both lineage 1 and 2 could be detected with the mutant peptides and kits of the invention (see e.g. FIG. 2). In particular, all samples showed clearly detectable signals that did not differ markedly between the wild type and the mutant E-proteins. Binding was similar in sera from patients infected with WNV strains belonging to genetic lineage 1 or lineage 2 [24], as demonstrated by signals obtained with sera from the United States, Canada or Italy (lineage 1) and Greece (lineage 2).

The West Nile Virus New York 1999 strain is a lineage 1 strain.

Sequences of lineage 2 strains are know to a skilled person. For example, the E protein of the nea santa strain 2010 may be used. Amino acids 1 to 501 of the E protein are disclosed in Genbank entry AED99787:

```
                                                              (SEQ ID No: 20)
         FNCLGMSNRD FLEGVSGATW VDLVLEGDSC VTIMSKDKPT IDVKMMNMEA ANLADVRSYC    60

YLASVSDLST RAACPTMGEA HNEKRADPAF VCKQGVVDRG WGNGCGLFGK GSIDTCAKFA   120

CTTKATGWII QKENIKYEVA IFVHGPTTVE SHGNYSTQTG ATQAGRFSIT PSAPSYTLKL   180

GEYGEVTVDC EPRSGIDTSA YYVMSVGAKS FLVHREWFMD LNLPWSSAGS TTWRNRETLM   240

EFEEPHATKQ SVVALGSQEG ALHQALAGAI PVEFSSNTVK LTSGHLKCRV KMEKLQLKGT   300

TYGVCSKAFK FAGTPADTGH GTVVLELQYT GTDGPCKVPI SSVASLNDLT PVGRLVTVNP   360

FVSVATANSK VLIELEPPFG DSYIVVGRGE QQINHHWHKS GSSIGKAFTT TLRGAQRLAA   420

LGDTAWDFGS VGGVFTSVGK AIHQVFGGAF RSLFGGMSWI TQGLLGALLL WMGINARDRS   480

IAMTFLAVGG VLLFLSVNVH A
```

```
                                     -continued
Amino acids 1 to 404 of the E protein of the nea santa strain 2010
are shown in SEQ ID No: 21:
                                                            (SEQ ID No: 21)
FNCLGMSNRD  FLEGVSGATW  VDLVLEGDSC  VTIMSKDKPT  IDVKMMNMEA  ANLADVRSYC   60

YLASVSDLST  RAACPTMGEA  HNEKRADPAF  VCKQGVVDRG  WGNGCGLFGK  GSIDTCAKFA  120

CTTKATGWII  QKENIKYEVA  IFVHGPTTVE  SHGNYSTQTG  ATQAGRFSIT  PSAPSYTLKL  180

GEYGEVTVDC  EPRSGIDTSA  YYVMSVGAKS  FLVHREWFMD  LNLPWSSAGS  TTWRNRETLM  240

EFEEPHATKQ  SVVALGSQEG  ALHQALAGAI  PVEFSSNTVK  LTSGHLKCRV  KMEKLQLKGT  300

TYGVCSKAFK  FAGTPADTGH  GTVVLELQYT  GTDGPCKVPI  SSVASLNDLT  PVGRLVTVNP  360

FVSVATANSK  VLIELEPPFG  DSYIVVGRGE  QQINHHWHKS  GSSI
```

In a further preferred embodiment, the peptide of the invention is produced recombinantly, preferably produced recombinantly by bacterial expression, more preferably by expression in *Escherichia coli*, and/or wherein the peptide is purified after an oxidative refolding protocol.

In a further preferred embodiment, the peptide produced recombinantly is produced in a eukaryotic cell, more preferably a eukaryotic cell selected from an insect cell, yeast cell and mammalian cell. Such eukaryotic expression systems are well known to a skilled person. For example, *S. cerevisiae, S. pombe* or *Hansenula* strains may be used as yeast host cells.

In case expression in insect cells is intended, S2 cells, in particular *Drosophila* S2 cells, may be used. In this preferred embodiment, the peptides are preferably produced by stable transfection of insect cells, in particular S2 cells.

In a further preferred embodiment, the peptide of the invention exhibits a three-dimensional folding and/or is refolded after bacterial expression, and/or wherein the peptide is purified and/or is not part of a virus-like particle or a virus particle.

As shown in the Examples, the ectodomain of the quadruple mutant of the WNV E protein was used successfully for discriminating a WNV infection from other flaviviral infections. The ectodomain of the WNV E protein preferably corresponds to amino acids 1 to 404 of the E protein as described above. In particular, by quantifying the binding of human antisera to the human wt ectodomain on the one hand and to the corresponding 76A, M77G, W101R, L107R quadruple mutant ectodomain on the other hand, it was surprisingly possible to discriminate between WNV infections on the one hand and DENV and TBEV infections on the other hand in a statistically significant manner (FIG. 3). Also, it was surprisingly possibly to discriminate between WNV infections and JEV vaccinations (FIG. 6). Therefore, in yet another embodiment, the present invention relates to a mutant peptide corresponding to the T76A, M77G, W101R, L107R quadruple mutant of the ectodomain of the E protein of the West Nile Virus (WNV).

The sequence of the T76A, M77G, W101R, L107R quadruple mutant of the ectodomain of the E protein of the West Nile Virus used in the experiments is depicted in SEQ ID No: 3 and corresponds to amino acids 1 to 404 of SEQ ID No: 2. Therefore, in yet another embodiment, the present invention relates to a mutant peptide with the sequence of amino acids 1 to 404 of SEQ ID No: 2. In yet another embodiment, the present invention relates to a mutant peptide with the sequence of SEQ ID No: 3.

In a preferred embodiment of the mutant peptides of the invention, the West Nile Virus is the West Nile Virus New York 1999 strain.

In a further preferred embodiment of the mutant peptides of the invention, the West Nile Virus has the genome sequence according to accession number FJ151394.

In a preferred embodiment of the mutant peptides of the invention, the West Nile Virus is of lineage 1 or lineage 2.

The mutant peptides of the invention allow rapid and reliable discrimination of WNV infections, without the need for generating complicated virus particles or virus-like particles. Preferably, the mutant peptides of the invention may be expressed recombinantly using a suitable host, such as insect cells or bacterial cells. In the examples, the mutant peptide of the invention was expressed recombinantly in *E. coli* cells using a pET21a plasmid. The mutant peptides are expressed as inclusion bodies. Methods for expression in bacterial host cells and insect host cells are known in the art.

In a further preferred embodiment of the mutant peptides of the invention, the peptide is produced recombinantly, preferably produced recombinantly by bacterial expression, more preferably by expression in *Escherichia coli*.

In a further preferred embodiment of the mutant peptides of the invention, the peptide is purified after an oxidative refolding protocol.

As described in the Examples, the oxidative refolding protocol was performed as described in Vogt M R (J Virol 2011, 85:11567-11580, Ref. [20]) and Oliphant T et al. (J Virol 2007, 81:11828-11839; Ref [21]). Inclusion bodies containing insoluble aggregates are denatured in the presence of 6 M guanidine hydrochloride and 20 mM β-mercaptoethanol and refolded in the presence of 400 mM L-arginine, 100 mM Tris-base (pH 8.0), 2 mM EDTA, 0.2 mM phenylmethylsulfonyl fluoride, and 5 and 0.5 mM reduced and oxidized glutathione, respectively.

Refolded protein is preferably separated from aggregates, as described in the Examples. Separation from aggregates was performed in the Examples on a Superdex 75 or 200, 16/60 size-exclusion column using fast-protein liquid chromatography (GE Healthcare, Piscataway, N.J.).

In a further preferred embodiment of the mutant peptides of the invention, the peptide exhibits a three-dimensional folding and/or is refolded after bacterial expression.

The mutant peptides of the invention are preferably employed in a refolded form, which exhibits three-dimensional folding. This enables samples from animals comprising antibodies, such as human sera to bind to the respective epitopes.

The mutant peptides of the invention which were expressed recombinantly in a bacterial host and which were refolded as described above, exhibited an appropriate three-dimensional folding.

In a further preferred embodiment, the mutant peptides of the invention further contain the correct disulfide bonds.

In order to determine that the mutant peptides of the invention and wildtype peptides employed in kits, methods and uses of the invention exhibit three-dimensional folding, one or more of the following analyses can be performed preferably (see Oliphant et al., Ref [21]): (i) elution as a monodispersed peak at the appropriate size on a gel filtration column; (ii) immunoreactivity with expected MAbs based on parallel yeast surface display studies; (iii) mass spectrometry analysis; (iv) circular dichroism spectroscopy; and (v) crystallographic analysis.

The mutant peptides of the invention may be glycosylated or unglycosylated.

Bacterial expression results in unglycosylated peptides, which can be refolded effectively. This allows easy and rapid expression and refolding. Therefore, in a further preferred embodiment of the mutant peptides of the invention, the peptide is unglycosylated.

A recombinant produced peptide has the advantage over mammalian cell-culture derived VLPs (virus-like particles) as it can be produced rapidly, inexpensively, and in higher yield, and can be quantified more precisely for diagnostic applications.

Therefore, in one preferred embodiment, the mutant peptides of the invention are not part of a virus-like particle and are not part of a virus particle.

The mutant peptides of the invention correspond to the ectodomain of the E protein. The folded mutant peptides of the invention are therefore soluble in an aqueous, buffered solution, such as PBS or PBS/Tween®-20 (0.05%).

Therefore, the invention further relates to an aqueous, buffered solution, such as PBS, wherein a mutant peptide of the invention is dissolved.

The invention further relates to a mutant peptide of the invention in a 15 mM $Na_2CO_3$, 35 nM $NaHCO_3$ pH 9.6 solution. The invention further relates to a mutant peptide of the invention dissolved in a 15 mM $Na_2CO_3$, 35 nM $NaHCO_3$ pH 9.6 solution. The invention further relates to a mutant peptide of the invention in a coating buffer.

In a further preferred embodiment of the mutant peptides of the invention, the peptide is purified and/or is not part of a virus-like particle or a virus particle.

The preferred embodiments for the mutant peptides of the invention also apply to the wildtype peptides (except mutations) described below for use in methods, uses and kits of the invention.

In another embodiment, the present invention relates to a nucleic acid encoding a mutant peptide of the invention as described herein or a biologically active variant thereof.

Methods for determining the sequence of a nucleic acid encoding a mutant peptide of the invention or a biologically active variant thereof are known in the art. Such nucleic acids may be generated using adequate primers and cloning procedures, for example by starting from the sequence of accession number FJ151394.

The nucleic acid encoding a mutated peptide of the invention or a biologically active variant thereof is preferably present in a gene expression construct, which allows expression of the mutated peptide of the invention. Elements of such constructs depend on the vector and host for expression. Typically, such constructs contain suitable promotor sequences, which are preferably inducible, and terminator sequences.

Therefore, in a yet further embodiment, the present invention relates to a gene expression construct comprising a nucleic acid encoding a mutant peptide of the invention or a biologically active variant thereof, which allows expression of a mutant peptide of the invention.

The nucleic acid and/or gene expression construct is in a preferred embodiment present in a suitable vector. The vector is typically chosen to allow for efficient production in a host. For example, a suitable plasmid may be used for expression in a bacterial host. For expression in *E. coli*, the plasmid pET21a was used in the Examples. In case expression in insect cells is intended, S2 cells, in particular *Drosophila* S2 cells may be used. In this preferred embodiment, the peptides are preferably produced by stable transfection of insect cells, in particular S2 cells.

Therefore in a yet further embodiment, the present invention relates to a vector, preferably plasmid, more preferably a pET21 a plasmid, comprising the nucleic acid or gene expression construct of the invention.

In a further preferred embodiment the present invention relates to a host cell, such as a eukaryotic cell, more preferably a eukaryotic cell selected from an insect cell, yeast cell and mammalian cell, or bacterial cell, preferably bacterial host cell, more preferably *Escherichia coli* cell comprising the vector or plasmid of the invention.

In a further preferred embodiment, the present invention relates to a method for producing a mutant peptide of the present invention or a biologically active variant thereof, comprising
 (i) cultivating a host cell of the invention.

In a more preferred embodiment, the method further comprises
 (ii) isolating a mutant peptide of the invention or a biologically active variant thereof, and
 (iii) optionally refolding the mutant peptide of the invention or the biologically active variant thereof.

It was surprisingly found that a kit comprising a mutant ectodomain peptide of the invention and the corresponding wildtype ectodomain peptide allows for the first time to provide a rapid, immuno-assay for discriminating WNV infections from other flaviviral infections. By determining the ratio of amount of (a) the antibody-wt peptide complex and (b) the antibody-mutant peptide complex, WNV infections can be identified, diagnosed, and discriminated against other flaviviral infections.

Therefore, in another embodiment, the present invention relates to a kit which comprises, preferably consists of:
 (a) at least one mutant West Nile Virus peptide of the invention, and
 (b) at least one wildtype peptide selected from the group of:
  (i) the ectodomain of the wildtype E protein of the West Nile Virus (WNV), preferably wherein the West Nile Virus is the West Nile Virus New York 1999 strain and/or has the a genome sequence according to accession number FJ151394,
  (ii) a peptide with the sequence of amino acids 1 to 404 of SEQ ID No: 1, and
  (iii) a peptide with the sequence of SEQ ID No: 4.

In a further preferred embodiment, the E protein of WNV is an E protein of a lineage 2 WNV, more preferably wherein the E protein comprises the sequence according to SEQ ID No: 20.

The kit comprises, preferably consists of:
 (a) 1, 2, 3, 4, 5, 6, 7, 8, 9, or 10 different mutant West Nile Virus peptides of the invention, and
 (b) 1, 2, 3, 4, 5, 6, 7, 8, 9, or 10 different wildtype peptides as described above.

In one preferred embodiment, the kit comprises, preferably consists of: one mutant West Nile Virus peptide of the invention and one wildtype peptide as described above.

The at least one peptide of (b) refers to at least one wt ectodomain peptide of WNV. SEQ ID No: 1 shows the sequence of amino acids 1 to 414 the wt E protein from West Nile Virus New York 1999 strain. The ectodomain is represented by amino acids 1 to 404 of SEQ ID No: 1. SEQ ID No: 4 shows amino acids 1 to 404 of SEQ ID No: 1. SEQ ID No: 20 shows the sequence of the N terminal portion of the wt E protein of a lineage 2 WNV strain. The ectodomain is represented by amino acids 1 to 404 of SEQ ID No: 20.

Preferred mutant West Nile Virus peptides of the invention for use in such kit are:
a mutant peptide corresponding to the T76A, M77G, W101R, L107R quadruple mutant of the ectodomain of the E protein of the West Nile Virus (WNV),
the mutant peptide with the sequence of amino acids 1 to 404 of SEQ ID No: 2, and
the mutant peptide with the sequence of SEQ ID No: 3.

Such mutant patent was used successfully in uses and methods of the invention as shown in the examples. As described above, the experiments were successfully performed with a mutant peptide with the sequence of SEQ ID No: 3, which corresponds to the T76A, M77G, W101R, L107R quadruple mutant of the ectodomain of the E protein of WNV and the corresponding wt ectodomain peptide with the sequence of SEQ ID No: 4.

In order to ensure equal loading of the mutant peptide and wt peptide to the solid support, various methods are available. For example, an antibody may be used which equally recognizes the mutant peptide and the wt peptide. In one preferred embodiment, an antibody may be used in kits, uses and methods of the invention, which recognizes an epitope on domain DIII of the E protein. Such epitope is distant from the mutations. In another preferred embodiment, equal loading of the mutant peptide and wt peptide to the solid support is achieved by measuring protein or peptide amount and/or concentration of a sample. In particular, the concentration of the peptide in a solution, such as an aqueous solution is measured, e.g. by measuring absorption, and by applying equal amounts for loading on the solid support, e.g. by pipetting or pumping.

As controls and reference samples, it is preferred that the kit further comprises animal samples, such as bird or mammalian samples, preferably human samples. Such samples may be CSF or serum samples, in particular serum samples, or blood, sputum or saliva samples.

In case it is intended to discriminate acute infections by determining IgM in sera, it is preferred that the kit also comprises reference or control samples from animals, such as mammalians, in particular humans, with confirmed acute infections.

Accordingly, in case it is intended to discriminate chronic infections by determining IgG in sera, it is preferred that the kit also comprises reference or control samples from animals, such as humans with confirmed chronic infections.

It is further preferred that the kit also comprises reference or control samples from animals, such as humans with confirmed vaccination against a flaviviral infection.

Such confirmed infections as reference or control samples preferably encompass animal samples, such as bird or mammalian samples from confirmed acute WNV infections and/or confirmed chronic WNV infections, in particular IgG-positive or IgM-positive or IgG/Ig-M positive samples, such as serum samples or CSF samples.

Therefore, the kit of the invention preferably further comprises reference or control samples, such as serum samples or CSF samples from animals, preferably birds or mammals, in particular humans, vaccinated against WNV or other flaviviral infections, such as dengue virus (DENV), tick-borne encephalitis virus (TBEV), Japanese encephalitis virus (JEV), usutu virus (USUV) and/or yellow fever virus (YFV), in particular human serum samples from JEV vaccinated individuals.

In another preferred embodiment, the kit of the invention further comprises reference or control samples, such as serum samples or CSF samples from animals, such as birds or mammals, in particular humans with confirmed flaviviral infection other than WNV, such as confirmed acute or confirmed chronic flaviviral infection other than WNV, in particular IgG-positive or IgM-positive or IgG/Ig-M positive samples, such as serum samples or CSF samples.

In particular, the kit of the invention further comprises reference or control samples, such as serum samples or CSF samples from animals, such as birds or mammals, in particular humans with confirmed TBEV infection, such as confirmed acute or confirmed chronic TBEV infection, in particular TBEV IgG-positive or IgM-positive or IgG/Ig-M positive samples, such as serum samples or CSF samples.

In particular, the kit of the invention further comprises reference or control samples, such as serum samples or CSF samples from animals, such as birds or mammals, in particular humans with confirmed DENV infection, such as confirmed acute or confirmed chronic DENV infection, in particular DENV IgG-positive or IgM-positive or IgG/Ig-M positive samples, such as serum samples or CSF samples. DENV may be of serotype 1, 2, 3, or 4.

In a further preferred embodiment, the sample as used in kits, methods and uses of the invention is selected from serum, blood, sputum, saliva and CSF sample.

In particular, the kit of the invention further comprises reference or control samples, such as serum samples or CSF samples from animals, such as birds or mammals, in particular humans with confirmed JEV infection, such as confirmed acute or confirmed chronic JEV infection, in particular JEV IgG-positive or IgM-positive or IgG/Ig-M positive samples, such as serum samples or CSF samples.

Moreover, the kit of the invention further comprises control or reference samples, such as serum samples or CSF samples from animals, such as birds or mammals, in particular humans which are confirmed to have no flaviviral infection and are not vaccinated against a flavivirus and who therefore are negative control mammals, in particular humans.

In another preferred embodiment, the above kit of the invention further comprises animal samples, such as birds or mammalian samples human serum samples from confirmed WNV infections. In another preferred embodiment, the above kit of the invention further comprises human serum samples from confirmed WNV infections. Such samples are control or reference samples.

In one preferred embodiment, the above kit of the invention further comprises reference or control human serum samples from
JEV vaccinated individuals, and/or
confirmed TBEV-infected individuals, in particular TBEV IgG-positive serum samples, and/or
DENV-infected individuals, in particular DENV IgG-positive and/or IgG/Ig-M positive serum samples, and/or
negative control individuals.

In one preferred embodiment, the above kit of the invention further comprises reference or control animal samples, such as birds or mammalian samples, from JEV infected or vaccinated individuals, and/or
confirmed TBEV-infected individuals, and/or
DENV-infected individuals, and/or
negative control individuals.

The samples are preferably serum, blood, sputum, saliva or CSF samples.

In case of mammalian samples, the positive reference or control sample is preferably IgG-positive, or IgM-positive or IgG/Ig-M positive samples.

In case of samples from birds, the positive reference or control sample are preferably IgY-positive samples.

These reference or control samples are suitable as positive or negative controls when performing the methods of the invention.

In case of an ELISA assay, a secondary antibody may be encompassed in a kit of the invention, which allows the detection of the formed mutant peptide-antibody complex and the formed wildtype peptide-antibody complex, respectively.

In an ELISA, an enzyme is typically attached to the secondary antibody, such as horseradish peroxidase (HRP). HRP can catalyze a reaction with the substrate TMB.

Alternatively, a third antibody may be used for detecting the secondary antibody, as shown in Example S2. The third antibody is preferably labelled with a detectable label, such as an enzyme, in this embodiment.

Therefore, in one preferred embodiment, the above kit of the invention further comprises an HRP-conjugated goat anti-human IgG antibody and/or TMB.

Therefore, in one preferred embodiment, the above kit of the invention further comprises an anti-mammalian IgG or anti-IgM antibody, in particular an anti-human or anti-horse IgG or anti-IgM antibody.

In case of samples from birds, the secondary antibody is preferably an anti-IgY-antibody, such as an anti-raptor IgY-antibody, anti-corvid IgY antibody or anti-passerine IgY antibody.

In the examples, the mutant peptides of the invention and the corresponding wt peptides are coated or bound to a solid support, namely a well plate. This is performed non-covalently using a coating buffer in the examples. Such solid support coated with peptides of the invention and optionally the corresponding wt peptides can be used in methods of the invention for discriminating WNV infections from other flaviviral infections.

Therefore, in yet another embodiment, the present invention relates to a solid support, preferably a plate, more preferably a well plate, even more preferably a Nunc polysorb plate, coated with at least one mutant peptide of the invention.

"Coating of a solid support" or "binding to a solid support" according to the present invention is preferably understood as covalent or non-covalent, preferably non-covalent binding to a solid support. Preferably, a solid support may be coated with a peptide or an antibody by incubation in the presence of a suitable coating buffer such as a carbonate/bicarbonate buffer as described in the Examples. Thereby, the peptide or an antibody is bound to the solid support. Alternatively, a bioaffine binding pair may be used for coating. Suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. For example, a peptide which further contains a biotin moiety may be bound to a solid support, which is in turn coated with streptavidin.

In a preferred embodiment, the solid support of the invention is further coated with at least one wildtype peptide selected from the group of:
(i) the ectodomain of the wildtype E protein of the West Nile Virus (WNV), preferably wherein the West Nile Virus is the West Nile Virus New York 1999 strain and/or has the a genome sequence according to accession number FJ151394, and/or is of lineage 1 or lineage 2,
(ii) a peptide with the sequence of amino acids 1 to 404 of SEQ ID No: 1, and
(iii) a peptide with the sequence of SEQ ID No: 4.

Preferably, the wildtype peptide corresponds to the mutant peptide, which means that the length and sequence of the wt peptide and the mutant peptide, respectively, is identical, with the exception of the mutations. However, it is preferably also possible to the wt peptide e.g. contains N-terminal and/or C-terminal deletions or contains further moieties as described below, or may contain 1, 2, 3, 4 or 5 further mutations, as long as the wt peptide is not a loss-of-function mutant with regard to the fusion loop, as described below.

It is preferred that the wildtype peptide is coated on a spatially different area than the mutant peptide, in order to distinguish between the formed complexes with an antibody. For example, in case of an array, such as microarray or nanoarray, or chip, multiple spots may be coated with only at least one mutant peptide, and multiple different, non-overlapping spots may be coated with only at least one wt peptide.

In the case of a well plate, one or more wells may be coated with only at least one mutant peptide, and one or more different wells may be coated with only at least one wt peptide.

Alternatively, at least one solid support may only be coated with only at least one mutant peptide. Optionally, at least one further solid support may only be coated with only at least one wt peptide.

Therefore, in a more preferred embodiment, the solid support is coated with at least one wildtype peptide on (an) area(s) spatially distinct from the area(s) coated with at least one mutant peptide.

In one other preferred embodiment, the present invention relates to a solid support coated with at least one mutant peptide of the invention. In a further preferred embodiment, the solid support does not contain a corresponding wt peptide.

In one further preferred embodiment, the present invention relates to a kit consisting of at least one mutant peptide of the invention. In a further preferred embodiment, the kit does not contain a corresponding wt peptide.

In an even more preferred embodiment, the solid support is a well plate and the individual wells are coated either only with at least one wildtype peptide or at least one mutant peptide.

In a further embodiment, the present invention relates to the use of a mutant peptide of the invention as described herein, or of a kit of the invention as described herein, or of a solid support of the invention as described herein, for distinguishing flavivirus infections. As shown in the Figures, flaviviral infections could be distinguished reliably in a statistically significant manner. In particular, WNV infections can be diagnosed and distinguished from other flaviviral infections, such as dengue virus (DENV), tick-borne encephalitis virus (TBEV), Japanese encephalitis virus (JEV), usutu virus (USUV) and/or yellow fever virus (YFV), more preferably from dengue virus (DENV) and tick-borne encephalitis virus (TBEV) infections.

A "flavivirus infection" is preferably understood as infection with a virus of the genus flavivirus in the family Flaviviridae. Further, a flavivirus infection is preferably understood as infection of an animal, preferably a bird or mammal, preferably a human, by a flavivirus. Preferably, flaviviruses typically have a size of about 40-65 nm, are enveloped and have an icosahedral nucleocapsid, and are positive-sense, single-stranded RNA viruses of approximately 10,000-11,000 bases.

Flaviviruses preferably encompass following viruses:
Tick-Borne Viruses
Mammalian Tick-Borne Virus Group
Alkhurma virus (ALKV)
Deer tick virus (DT)
Gadgets Gully virus (GGYV)
Kadam virus (KADV)
Karshi virus
Kyasanur Forest disease virus (KFDV)
Langat virus (LGTV)
Louping ill virus (LIV)
Omsk hemorrhagic fever virus (OHFV)
Powassan virus (POWV)
Royal Farm virus (RFV)
Tick-borne encephalitis virus (TBEV)
Turkish sheep encephalitis virus (TSE)
Seabird Tick-Borne Virus Group
Meaban virus (MEAV)
Saumarez Reef virus (SREV)
Tyuleniy virus (TYUV)
Mosquito-Borne Viruses
Without Known Vertebrate Host
Aedes flavivirus
Barkedji virus
Calbertado virus
Cell fusing agent virus
Chaoyang virus
Culex flavivirus
Culex theileri flavivirus
Donggang virus
Kamiti River virus
Lammi virus
Nakiwogo virus
Nounane virus
Quang Binh virus
Aroa Virus Group
Aroa virus (AROAV)
Dengue Virus Group
Dengue virus (DENV)
Kedougou virus (KEDV)
Japanese Encephalitis Virus Group
Bussuquara virus
Cacipacore virus (CPCV)
Koutango virus (KOUV)
Ilheus virus (ILHV)
Japanese encephalitis virus (JEV)
Murray Valley encephalitis virus (MVEV)
Rocio virus (ROCV)
St. Louis encephalitis virus (SLEV)
Usutu virus (USUV)
West Nile virus (WNV)
Yaounde virus (YAOV)
Kokobera Virus Group
Kokobera virus (KOKV)
Ntaya Virus Group
Bagaza virus (BAGV)
Duck egg drop syndrome virus (BYDV)
Ilheus virus (ILHV)
Jiangsu virus (JSV)
Israel turkey meningoencephalomyelitis virus (ITV)
Ntaya virus (NTAV)
Tembusu virus (TMUV)
Spondweni Virus Group
Zika virus (ZIKV)
Yellow Fever Virus Group
Banzi virus (BANV)
Bouboui virus (BOUV)
Edge Hill virus (EHV)
Jugra virus (JUGV)
Saboya virus (SABV)
Sepik virus (SEPV)
Uganda S virus (UGSV)
Wesselsbron virus (WESSV)
Yellow fever virus (YFV)
Viruses with no Known Arthropod Vector
Entebbe Virus Group
Entebbe bat virus (ENTV)
Yokose virus (YOKV)
Modoc Virus Group
Apoi virus (APOIV)
Cowbone Ridge virus (CRV)
Jutiapa virus (JUTV)
Modoc virus (MODV)
Sal Vieja virus (SVV)
San Perlita virus (SPV)
Rio Bravo Virus Group
Bukalasa bat virus (BBV)
Carey Island virus (CIV)
Dakar bat virus (DBV)
Montana myotis leukoencephalitis virus (MMLV)
Phnom Penh bat virus (PPBV)
Rio Bravo virus (RBV)

Clinically relevant flaviviral infections are preferably understood as infections with flaviviruses which cause or may cause an illness in an animal, preferably bird or mammal, in particular human or horse. For example, clinically relevant flaviviral infections preferably encompasses infections with West Nile Virus, dengue virus (DENV), tick-borne encephalitis virus (TBEV), Japanese encephalitis virus (JEV), usutu virus (USUV) and/or yellow fever virus (YFV).

The E protein of the flaviviruses is a conserved envelope protein, as described above.

The E protein of Dengue viruses are known to a skilled person. For example, amino acids 1 to 495 of the E protein dengue virus, serotype 1, is disclosed in GenBank Accession No: AEV66294.1:

```
                                              (SEQ ID No: 12)
    mrcvgigsrd fveglsgatw vdvvlehgsc vttmakdkpt ldiellktev tnpavlrklc 61 ieakisnttt dsrcptqgea tlveeqdanf vcrrtfvdrg wgngcglfgk gslitcakfk
```

-continued

```
121 cvtklegkiv qyenlkysvi vtvhtgdqhq vgnestehgt tatitpqapt teiqltdyga 181 ltldcsprtg ldfnemvllt mkekswlvhk qwfldlplpw tsgastsqet wnrqdllvtf 241 ktahakkqev vvlgsqegam htaltgatei qtsgtttifa ghlkcrlkmd kltlkgmsyv 301 mctgsfklek elaetqhgtv lvqikyegtd apckipfstq dekgvtqngr litanpivtd 361 kekpvnieae ppfgesyivi gagekalkls wfkkgssigk mfeatargar rmailgdtaw 421 dfgsiggvft svgklvhqif gtaygvlfsg vswtmkigig vlltwlglns rstslsmtci 481 avglvtlylg vmvqa
```

For example, the E protein of dengue virus, serotype 2, as disclosed in GenBank Accession No: BAL05267.1 (amino acids 1-495) has the following sequence:

(SEQ ID No: 13)
```
  1 mrcigisnrd fvegvsggsw vdivlehgsc vttmaknkpt ldfeliktea kqpatlrkyc 61 ieakltnttt esrcptqgep slkeeqdkrf vckhsmvdrg wgngcglfgk ggivtcamft 121 ckknmegkiv qpenleytiv vtphsgeeha vgndtgkhgk eikvtpqssi teaeltgygt 181 vtmecsprtg ldfnemvllq menkawlvhr qwfldlplpw lpgadkqesn wiqketlvtf 241 knphakkqdv vvlgsqegam htaltgatei qmssgnllft ghlkcrlrmd klqlkgmsys 301 mctgkfkvvk eiaetqhgti virvqyegdg spckipfeim dlekryvlgr litvnpivte 361 kdspvnieae ppfgdsyiii gvepgqlkln wfkkgssigq mfettmrgak rmailgdtaw 421 dfgslggyft sigkalhqvf gaiygaafsg vswtmkilig viitwigmns rstslsyslv 481 vgivtlylg vmvqa
```

For example, the E protein of dengue virus, serotype 3, is disclosed in GenBank Accession No: AAD37780.1. The amino acids 1-493 have the following sequence:

(SEQ ID No: 14)
```
    mrcvgvgnrd fveglsgasw vdvvlehggc vttmaknkpt ldielqktea tqlatlrklc 61 iegkitnitt dsrcptqgea ilpeeqdqny vckhtyvdrg wgngcglfgk gslvtcakfq 121 clepiegkvv qhenlkytvi itvhtgdqhq vgndtqgvtv eitpqastve ailpeygtlg 181 lecsprtgld fnemilltmk nkawmvhrqw ffdlplpwts gattetptwn rkellvtfkn 241 ahakkqevvv lgsqegamht altgateiqn sggtsifagh lkcrlkmdkl elkgmsyamc 301 lntfylkkev setqhgtili kveykgedap ckipfstedg qgkahngrli tanpvvtkke 361 epvnieaepp fgesnivigi gdkalkinwy kkgssigkmf eatargarrm ailgdtawdf 421 gsvggvlnsl gkmvhqifgs aytalfsgvs wimkigigvl ltwiglnskn tsmsfsciai 481 giitlylgvv vqa
```

For example, the E protein of dengue virus, serotype 4, is disclosed in GenBank Accession No: AEV66313.1. The amino acids 1-495 have the following sequence:

(SEQ ID No: 15)
```
    mrcvgvgnrd fvegvsggaw vdlvlehggc vttmaqgkpt ldfeliktta kevallrtyc 61 ieasisnitt atrcptqgep ylkeeqdqqy icrrdvvdrg wgngcglfgk ggvvtcakfs 121 csgkitgnlv qienleytvv vtvhngdtha vgndtsnhge tatitprsps vevklpdyge 181 ltldceprsg idfnemilmk mktktwlvhk qwfldlplpw tagadtsevh wnhkermvtf
```

```
241 kvphakrqdv tvlgsqegam hsalagatev dsgdgnhmfa ghlkckvrme klrikgmsyt 301 mcsgkfsidk emaetqhgtt vvkvkyegtg apckvpieir dvnkekvvgr iisstpfaen 361 tnsvtniele ppfgdsyivi gvgdsaltlh wfrkgssigk mfestyrgak rmailgetaw 421 dfgsvggllt slgkavhqvf gsvyttmfgg vswmvrilig llvlwigtns rntsmamsci 481 avggitlflg ftvha
```

For example, the E protein of JEV is disclosed in GenBank Accession No: AAQ73507 and the N-terminal portion has the following sequence:

```
                                              (SEQ ID No: 16)
fnclgm gnrdfiegas gatwvdlvle gdscltiman dkptldvrmi nieasqlaev rsycyhasvt distvarcpt tgeahnekra dssyvckqgf tdrgwgngcg lfgkgsidtc akfsctskai grtiqpenik yevgifvhgt ttsenhgnys aqvgasqaak ftvtpnapsi tlklgdygev tldceprsgl nteafyvmtv gsrsflvhre wfhdlalpwt spsstawrnr ellmefeeah atkqsvvalg sqegglhqal agaivveyss svkltsghlk crlkmdklal kgttygmctk kfsfaknpad tghgtvviel sysgsdgpck ipivsvasln dmtpvgrlvt vnpfvatssa nskylvemep pfgdsyivvg rgdkqinhhw hkagstlgka fsttlkgaqr laalgdtawd fgsiggvfns igkavhqvfg gafrtlfggm switqglmga lllwmgvnar drsialafla tggvlvflat nvha.
```

In a further embodiment, the present invention relates to the use of a mutant peptide of the invention as described herein, or of a kit of the invention as described herein, or of a solid support of the invention as described herein, for distinguishing a West Nile Virus infection from other flavivirus infections, preferably for distinguishing a West Nile Virus infection from other clinically relevant flaviviral infections and/or from dengue virus (DENV), tick-borne encephalitis virus (TBEV), Japanese encephalitis virus (JEV), usutu virus (USUV) and/or yellow fever virus (YFV) infections.

As explained above, it is possible using the peptides and kits of the invention to reliably and quickly distinguish an infection with WNF from an infection with other flaviviruses, such as: dengue virus (DENV), in particular serotype 1, 2, 3, 4 and 5, tick-borne encephalitis virus (TBEV), Japanese encephalitis virus (JEV), usutu virus (USUV) and/or yellow fever virus (YFV) infections. In the examples, a WNV infection could be distinguished with statistical significance from DENV infections of various serotypes and TBEV infections.

Therefore, in a most preferred embodiment of a use of the invention, a West Nile Virus infection can be distinguished from dengue virus (DENV) and/or TEBV virus infections. A dengue virus infection may be an infection with Dengue virus serotype 1, 2, 3, 4 or 5, more preferably 1, 2, 3, or 4.

In a further embodiment, the present invention relates to the use of a mutant peptide of the invention as described herein, or of a kit of the invention as described herein, or of a solid support of the invention as described herein, for specifically detecting antibodies binding to the West Nile Virus (WNV). Prior art assays suffer from high cross-reactivities. Specific detection of antibodies binding to WNV was not possible. This problem is solved by the mutant peptides and kits of the invention. In a preferred embodiment, these antibodies are in samples from animals, such as mammals or birds, infected with West Nile Virus or other flaviviruses. In one preferred embodiment, these antibodies are in sera from humans infected with West Nile Virus or other flaviviruses. In a preferred embodiment, these antibodies are IgG and/or IgM antibodies.

In a further preferred embodiment, these antibodies are in samples from animals, in particular birds or mammals infected with West Nile Virus or other flaviviruses. In a more preferred embodiment, the animal is a mammal, such as a human or horse, and the antibodies are IgA, IgG and/or IgM antibodies. In a further more preferred embodiment, the animal is a bird, such as a raptor, corvid or passerine, and the antibodies are IgY antibodies.

As the antibodies detected in the uses and methods of the invention are preferably antibodies present in sera of animals, such as birds or mammals, preferably humans, these detected antibodies are preferably naturally occurring antibodies, more preferably antibodies naturally occurring in mammals, preferably humans, or birds.

Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. Naturally occurring antibodies including antibody isotypes known as IgA, IgD, IgE, IgG and IgM are preferred formats of detected antibodies. Naturally occurring antibodies in birds include antibodies of isotype IgY.

In a more preferred embodiment, the antibodies in mammalian sera, preferably human sera, are in IgG or IgM format.

In a further more preferred embodiment, the antibodies in mammalian saliva, preferably human saliva, are in IgA format.

In a further more preferred embodiment, the antibodies in bird samples are in IgY format.

As described above, IgM antibodies are produced approximately 4 to 7 days after infection with WNV and IgG antibodies appear a few days later.

Therefore, for methods and uses of the invention wherein the human suffers or is suspected to suffer from an acute flaviviral infection, in particular 4 to 7 days after infection, the antibodies detected in the peptide-antibody complexes are preferably in IgM format.

Therefore, for methods and uses of the invention wherein the human suffers or is suspected to suffer from a chronic flaviviral infection, in particular 8, 9, 10, 14 or more days after infection, the antibodies detected in the peptide-antibody complexes are preferably in IgM format.

Therefore, for methods and uses of the invention wherein the mammal suffers or is suspected to suffer from an acute flaviviral infection, in particular 4 to 7 days after infection, the antibodies detected in the peptide-antibody complexes are preferably in IgM format.

Therefore, for methods and uses of the invention wherein the mammal suffers or is suspected to suffer from a chronic flaviviral infection, in particular 8, 9, 10, 14 or more days after infection, the antibodies detected in the peptide-antibody complexes are preferably in IgM format.

Therefore, the animal, preferably bird or mammalian sample, preferably human sample, is preferably obtained 1, 2, 3, 4, 5, 6, 7, 8, 9, 10, 11, 12, 13, 14, or more days after infection or suspected infection with a flavivirus. For example, the sample may be obtained about 2, 3, 4, 5, 6, 7, 8 or more weeks or about 2, 3, 4, 5, 6, 7, 8 or more months after infection or suspected infection with a flavivirus.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two beta sheets create a "sandwich" shape, held together by interactions between conserved cysteines and other charged amino acids.

There are five types of mammalian Ig heavy chain denoted by α, δ, ε, γ, and µ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while µ and ε have approximately 550 amino acids. Each heavy chain has two regions, the constant region (CH) and the variable region (VH). In one species, the constant region is identical in all antibodies of the same isotype, but differs in antibodies of different isotypes. Heavy chains γ, α and δ have a constant region composed of three tandem Ig domains, and a hinge region for added flexibility; heavy chains µ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

For the kits, methods and uses of the invention preferably also employ further antibodies, such as optionally labelled secondary or third antibodies, anti-human IgG- or anti-human IgM-antibodies or anti-human IgA antibodies, or anti-mammalian IgG-antibodies such as an anti-horse IgG antibody, an optionally labelled secondary antibody which specifically recognizes an epitope on the wildtype and mutant peptides, which is at least 5, 10, or 15 amino acids distant from the fusion loop domain, in particular wherein the fusion loop domain corresponds to amino acids 63 to 120 of the E protein of a flavivirus.

For such antibodies, the term "antibody" preferably encompasses both naturally occurring and artificial antibody formats.

In addition to naturally occurring antibodies, artificial antibody formats including antibody fragments have been developed. Some of them are described in the following. However, any other antibody format is preferably also encompassed by the present invention as well.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, preferably means any polypeptide which has structural similarity to a naturally occurring antibody and which has the required binding specificity, which is determined by the CDRs of the polypeptides. Hence, "antibody" is preferably intended to relate to an immunoglobulin-derived structure with the required specific binding, such as specific binding to human IgM in case of an anti-human IgM antibody, including but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to respective antigen. The antibody may be any polypeptide which comprises at least one antigen binding fragment. Antigen binding fragments consist of at least the variable domain of the heavy chain and the variable domain of the light chain, arranged in a manner that both domains together are able to bind to the specific antigen.

An "antibody fragment" preferably also contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

As the first generation of full sized antibodies presented some problems, many of the second generation antibodies have comprised only fragments of the antibody. Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides. A recombinant antibody fragment is the single-chain Fv (scFv) fragment. In general, it has a high affinity for its antigen and can be expressed in a variety of hosts. Dissociation of scFvs results in monomeric scFvs, which can be complexed into dimers (diabodies), trimers (triabodies) or larger aggregates such as TandAbs and Flexibodies. Antibodies with two binding domains can be created either through the binding of two scFv with a simple polypeptide link (scFv)2 or through the dimerization of two monomers (diabodies). Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany).

Certain antibody molecules including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTE™ technology (molecules possessing antigen binding regions of different specificity with a peptide linker) and knobs-into-holes engineering.

Accordingly, the antibody as employed or used herein may be a Fab, a Fab', a F(ab')2, a Fv, a disulfide-linked Fv, a scFv, a (scFv)2, a bivalent antibody, a bispecific antibody, a multispecific antibody, a diabody, a triabody, a tetrabody or a minibody.

In another preferred embodiment, the antibody is a monoclonal antibody. Monoclonal antibodies are monospecific antibodies that are identical because they are produced by one type of immune cell that are all clones of a single parent cell.

As detailed above in the context with antibodies, each heavy chain of a naturally occurring antibody has two regions, the constant region and the variable region. There are five types of mammalian immunoglobulin heavy chain: γ, δ, α, μ and ε, which define classes of immunoglobulins IgM, IgD, IgG, IgA and IgE, respectively.

A secondary antibody as used herein is preferably labelled with a detectable label in order to allow for detection. The term "detectable label" as used herein preferably refers to any substance that is capable of producing a signal via direct or indirect detection. The detectable label thus may be detected directly or indirectly. For direct detection label suitable for use in the present invention can be selected from any known detectable marker groups, like chromogens, fluorescent groups, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of detectable labels are luminescent metal complexes, such as ruthenium or europium complexes, e.g. as used for ECLIA, enzymes, e.g. as used for ELISA and ELISA capture assay, and radioisotopes; e.g. as used for RIA.

A preferred assay of the invention is an ELISA assay. Therefore, an enzyme, such as horseradish peroxidase is a preferred detectable label for such secondary antibody.

Indirect detection systems comprise, for example, that the detection reagent, e.g. the detection antibody, is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g. by the detectable labels as mentioned above.

In a further embodiment, the present invention relates to the use of a mutant peptide of the invention as described herein, or of a kit of the invention as described herein, or of a solid support of the invention as described herein, for a serological assay. Therefore, a mutant peptide of the invention as described herein, or a kit of the invention as described herein, or a solid support of the invention may be used for the diagnostic identification of antibodies in the serum, in particular by detecting WNV antibodies and/or distinguishing WNV antibodies from antibodies binding to other flaviviruses.

Therefore, in a preferred embodiment, the serological assay is for the detection of WNV antibodies. Such assay is of high importance in regions where other flaviviruses co-circulate and/or in animal populations, in particular human populations, that are immunized with other flavivirus vaccines. In such regions, crossreactivity of antibodies represents a major problem for serological assays of the prior art.

Therefore, in a more preferred embodiment, the serological assay is for the detection of WNV antibodies in regions where other flaviviruses co-circulate and/or in populations that are immunized with other flavivirus vaccines.

In particular, WNV IgG antibodies may be detected successfully, and a rise in IgG antibody titers over time may be measured. In a further embodiment, the present invention relates to the use of a mutant peptide of the invention as described herein, or of a kit of the invention as described herein, or of a solid support of the invention as described herein, for detecting WNV IgG antibodies. In a preferred embodiment, a rise in IgG antibody titers over time may be measured. For example, samples may be obtained as the day of symptoms onset (d0), and/or at day 10, day 15, day 20 or day 30 after day of symptoms onset.

The embodiments of the present invention are also useful for detecting and discriminating acute WNV infections characterized by IgM antibodies. An early identification is important for further supportive treatment of a patient. In a further embodiment, the present invention relates to the use of a mutant peptide of the invention as described herein, or of a kit of the invention as described herein, or of a solid support of the invention as described herein, for detecting WNV IgM antibodies.

In a preferred embodiment, the WNV IgM antibodies are detected in an IgM-capture assay or IgM-capture ELISA assay. In such IgM-capture assay, anti-IgM antibodies may be bound to a solid support such as an array, chip, bead, or plate, such as a well plate or multi-well plate.

In a further embodiment, the present invention relates to the use of a mutant peptide of the invention as described herein, or of a kit of the invention as described herein, or of a solid support of the invention as described herein, for determining WNV infections rapidly and reliably.

The present invention also provides a method for distinguishing a West Nile Virus infection from other flavivirus infections, as evidenced in the examples for dengue virus (DENV), tick-borne encephalitis virus (TBEV) and Japanese encephalitis virus (JEV). In the examples, solid supports, namely plates coated with mutant peptides of the invention and the corresponding wt peptide, were brought into contact with antibodies in human sera from persons who are infected with either WNV or other flaviviruses (DENV or TBEV) or vaccinated against other flaviviruses (JEV). The amounts of antibodies bound to (a) the wt peptide and (b) the mutant peptide, respectively, were determined in the Examples. This was performed using a secondary anti-human IgG antibody in the Examples (HRP-conjugated goat anti-human IgG). This secondary antibody was in turn detected by the enzymatic reaction catalyzed by HRP. The ratio (a)/(b) between the amounts determined for (a) the at least one wildtype peptide and (b) the at least one mutant peptide was determined. It was surprisingly found that statistically significant differences in ratio were determined for WNV infections as compared to infections with other flaviviruses. Whereas the ratio was low, i.e. close to 1, for WNV infections (1.22±0.2), the ratio was elevated, i.e. clearly higher than 1, for other infections: 5.92±3.1 for DENV and 6.06±2.1 for TBEV.

In another embodiment, the present invention relates to a method for distinguishing a West Nile Virus infection from other flavivirus infections, preferably from other clinically relevant flaviviral infections and/or from dengue virus (DENV), tick-borne encephalitis virus (TBEV), Japanese encephalitis virus (JEV), usutu virus (USUV) and/or yellow fever virus (YFV) infections, most preferably from dengue virus (DENV) and/or TEBV virus infections, comprising the following steps:
(i) contacting at least one solid support of the invention with an animal, in particular sample containing or suspected to contain antibodies binding to a flavivirus, in particular West Nile Virus,
preferably wherein the animal sample is serum or cerebrospinal fluid, more preferably human serum or human cerebrospinal fluid,
(ii) determining the amount of bound antibodies,
(iii) determining the ratio (a)/(b) between the amounts determined for (a) the at least one wildtype peptide and (b) the at least one mutant peptide,
wherein an elevated ratio, preferably a ratio of about 5.92±3.1 or about 6.06±2.1 indicates that the animal, preferably human is not infected with West Nile Virus, and is infected with another flavivirus or is vaccinated against another flavivirus, or wherein a low ratio, preferably a ratio of about 1.22±0.2 indicates that the animal, preferably human is infected with West Nile Virus or is vaccinated against West Nile Virus.

In a preferred embodiment, the animal is a mammal, such as a human or horse, or the animal is a bird. In a particularly preferred embodiment, the animal is a human.

In a preferred embodiment, the amount of bound antibodies in step (ii) is determined by using a secondary antibody.

For example, a secondary anti-mammal Ig-A, anti-IgG or anti-IgM-antibody, preferably anti-human Ig-A, anti-IgG or anti-IgM-antibody, is used in the case of a mammalian sample, preferably human sample. For example, a secondary anti-bird IgY antibody is used in the case of a bird sample.

In a preferred embodiment, it is possible to use one, two, three, four, five, six or more solid supports of the invention. It is possible that one solid support is coated both with at least one mutant peptide of the invention and at least one wildtype peptide of the invention. In this embodiment, the coated areas are spatially distinct and non-overlapping. This allows quantification of the binding of the antibodies to the different peptides. For example a solid support such as a well plate may be used as shown in the Examples. As shown in the examples, separate wells may be coated with either only a mutant peptide or only a wildtype peptide of the invention.

Alternatively, a plurality of solid supports may be used. For example, each solid support, such as a well plate, array or bead may be coated either with at least one mutant peptide or at least a wildtype peptide only.

In a preferred embodiment of the method of the invention, the amount of bound antibodies in step (ii) is measured by contacting an HRP-conjugated goat anti-human IgG antibody with the solid support after step (i), more preferably wherein TMB substrate is added subsequently. This allows determining the amount of peptide-antibody complexes in an ELISA assay.

In a preferred embodiment of the methods, kits, and solid supports of the invention, equal loading of at least one mutant peptide and at least one wildtype peptide on each well or spot of the coated solid support is ensured using a suitable antibody, as shown in the examples. In another preferred embodiment, equal loading of the mutant peptide and wt peptide to the solid support is achieved by measuring protein or peptide amount and/or concentration of a sample. In particular, the concentration of the peptide in a solution, such as an aqueous solution is measured, e.g. by measuring absorption, and by applying equal amounts for loading on the solid support, e.g. by pipetting or pumping.

In another preferred embodiment of the methods, kits, and solid supports of the invention, 50 ng to 300 ng, more preferably 50 ng to 200 ng, even more preferably 50 ng, 100 ng or 200 ng of a mutant peptide or wildtype peptide is coated to each well or spot of the solid support.

It was shown that the method of the invention can be performed using various amounts of peptide. For example 50 ng, 100 ng, 200 ng or 300 ng were detected.

The methods of the invention are preferably in vitro methods.

In another embodiment, the present invention relates to a method for distinguishing a West Nile Virus infection from other flavivirus infections, preferably from other clinically relevant flaviviral infections and/or from dengue virus (DENV), tick-borne encephalitis virus (TBEV), Japanese encephalitis virus (JEV), usutu virus (USUV) and/or yellow fever virus (YFV) infections, most preferably from dengue virus (DENV) and/or TEBV virus infections, comprising the following steps:
(i) performing an ELISA assay with a solid support of the invention and an animal sample containing or suspected to contain antibodies binding to a flavivirus, in particular West Nile Virus, wherein the solid support is coated with at least one mutant peptide of the invention and at least one corresponding wt peptide,
preferably wherein the animal sample is human serum or human cerebrospinal fluid,
(ii) determining the amount of antibodies bound to (a) the at least one wildtype peptide and (b) the at least one mutant peptide,
(iii) determining the ratio (a)/(b) between the amounts determined for (a) the at least one wildtype peptide and (b) the at least one mutant peptide,
wherein an elevated ratio, preferably a ratio of about 5.92±3.1 or about 6.06±2.1 indicates that the animal, preferably human is not infected with West Nile Virus, and is infected with another flavivirus or is vaccinated against another flavivirus, or wherein a low ratio, preferably a ratio of about 1.22±0.2 indicates that the animal, preferably human is infected with West Nile Virus or is vaccinated against West Nile Virus.

In yet another embodiment, the present invention relates to a method for distinguishing a West Nile Virus infection from other flavivirus infections, preferably from other clinically relevant flaviviral infections and/or from dengue virus (DENV), tick-borne encephalitis virus (TBEV), Japanese encephalitis virus (JEV), usutu virus (USUV) and/or yellow fever virus (YFV) infections,
most preferably from dengue virus (DENV) and/or TEBV virus infections, comprising the following steps:
(1) contacting at least one mutant peptide of the invention with an animal sample containing or suspected to contain antibodies binding to a flavivirus, in particular West Nile Virus,
preferably wherein the animal sample is human serum or human cerebrospinal fluid,
(2) contacting at least one wildtype peptide selected from the group of:
(i) the ectodomain of the wildtype E protein of the West Nile Virus (WNV), preferably wherein the West Nile Virus is the West Nile Virus New York 1999 strain and/or has the a genome sequence according to accession number FJ151394
(ii) a peptide with the sequence of amino acids 1 to 404 of SEQ ID No: 1, and
(iii) a peptide with the sequence of SEQ ID No: 4,
with an animal sample, in particular human serum or human cerebrospinal fluid,
(3) determining the amount of bound antibodies in steps (1) and (2), in particular by using a secondary anti-human IgG or IgM antibody,
(4) determining the ratio (a)/(b) between the amounts determined for (a) the at least one wildtype peptide and (b) the at least one mutant peptide,
wherein an elevated ratio, preferably a ratio of about 5.92±3.1 or about 6.06±2.1 indicates that the animal, preferably human is not infected with West Nile Virus, and is infected with another flavivirus or is vaccinated against another flavivirus, or wherein a low ratio, preferably a ratio of about 1.22±0.2 indicates that the animal, preferably human is infected with West Nile Virus or is vaccinated against West Nile Virus.

In yet another embodiment, the present invention relates to the use of a recombinant peptide representing the ectodomain of a loss-of-function mutant of the WNV E-protein for discriminating West Nile virus infections from infections with other flavivirus(es) or vaccinations against other flavivirus(es). In a preferred embodiment, the loss-of-function mutant of the WNV E-protein, preferably loss-of-function mutant of the WNV E-protein ectodomain, is mutant peptide as described above, i.e. a mutant peptide selected from
(a) the T76A, M77G, W101R, L107R quadruple mutant of the ectodomain of the E protein of the West Nile Virus (WNV), or
(b) a peptide with the sequence of amino acids 1 to 404 of SEQ ID No: 2,
(c) a peptide with the sequence of SEQ ID No: 3.

Other peptides which may be used according to the invention as loss-of-function mutant of the WNV E-protein are the mutant peptide corresponding to the ectodomain of
(1) the W101R mutant of the WNV E protein, or
(2) the W101R L107R mutant of the WNV E protein,
(3) the T76R M77E W101R L107R mutant of the WNV E protein,
in particular the mutant peptide corresponding to the ectodomain of the T76R M77E W101R L107R mutant of the WNV E protein.

A "loss-of-function mutant" of the E-protein of a flavivirus is preferably understood as a mutant E protein of a flavivirus, which is not recognized by antibodies specifically binding the fusion loop domain of the wt E protein of the flavivirus, preferably wherein the mutant E protein of a flavivirus is not recognized by antibodies specifically binding the fusion loop domain of the wt E protein of the flavivirus which are obtained from heterologous flaviviral infections. "Not recognized" is preferably understood as that the Kd value for binding of such antibody to the mutant E protein is at least 10-fold, preferably at least 100-fold, more preferably at least 1000-fold higher than the Kd value for binding of the antibody to the of the wt E protein of the flavivirus. Therefore, the loss-of-function mutants of the E proteins of the invention are preferably loss-of-function mutants with regard to the fusion loop of a flavivirus E protein. The "fusion loop" or "fusion loop domain" is preferably understood as the amino acid sequence of the fusion loop of DII, also known as "DII-fl" in the art. In particular, the fusion loop domain preferably corresponds to amino acids 63 to 120 of the E protein of WNV, TBEV and DENV, serotypes 1 to 4. Accordingly, "loss-of-function peptides" are preferably peptides of the invention which contain part of the sequence of the loss-of-function E protein mutants of a flavivirus. For example, loss-of-function peptides representing the ectodomain preferably refer to the peptides having the sequence of the ectodomain of a loss-of-function mutant of the E-protein of a flavivirus.

In a preferred embodiment, West Nile virus infections can be discriminated from infections with other clinically relevant flavivirus infections, in particular dengue virus (DENV), tick-borne encephalitis virus (TBEV), Japanese encephalitis virus (JEV), usutu virus (USUV) and/or yellow fever virus (YFV) infections. In a more preferred embodiment, West Nile virus infections can be discriminated from dengue virus and/or TEBV virus infections, even more preferably, dengue virus is selected from dengue virus (DENV) serotype 1, 2, 3, 4 and 5.

As described above, the principle of using recombinant loss-of-function mutants of the WNV E-protein ectodomain can be applied to other flaviviral infections. Therefore, the present invention also discloses kits, methods and uses for discriminating a specific flaviviral infection from other flaviviral infections or vaccinations against such other flaviviruses: In yet another embodiment, the present invention relates to the use recombinant peptide representing the ectodomain of a loss-of-function mutant of the E-protein specific flavivirus, preferably selected from dengue virus (DENV), tick-borne encephalitis virus (TBEV), Japanese encephalitis virus (JEV), usutu virus (USUV) and yellow fever virus, more preferably selected from dengue virus (DENV) serotype 1, 2, 3, 4 and 5, and tick-borne encephalitis virus (TBEV), for discriminating infections with such specific flavivirus from infections with other flavivirus(es), preferably from infections with other clinically relevant flavivirus infections.

For example, a recombinant peptide representing the ectodomain of a loss-of-function mutant of the E-protein of TBEV may be used, as well as its corresponding wt peptide, i.e. the corresponding ectodomain peptide without mutations. In a preferred embodiment, the peptide representing the ectodomain of the T76A, M77G, W101R, L107R quadruple mutant or the T76R, M77E, W101R, L107R quadruple mutant of the E protein of TBEV may be used. Such mutant TBEV peptide may be used together with its corresponding peptide representing the ectodomain of the wt E protein of TBEV. The peptides can be used for discriminating TBEV infections from other flaviviral infections in particular WNV, and/or DENV infections and/or JEV infections.

For example, a recombinant peptide representing the ectodomain of a loss-of-function mutant of the E-protein of DENV serotype 1, 2, 3, 4 or 5 may be used, as well as its corresponding wt peptide, i.e. the corresponding ectodomain peptide without mutations.

In a preferred embodiment, the peptide representing the ectodomain of
(a) the T76R, Q77E, W101R, L107R quadruple mutant of the E protein of DENV serotype 1, 2, 3, 4 or 5 and/or
(b) the T76A, Q77G, W101R, L107R quadruple mutant of the E protein of DENV serotype 1, 2, 3, 4 or 5 may be used.

Such mutant DENV serotype 1, 2, 3, 4 or 5 peptide may be used together with its corresponding peptide representing the ectodomain of the wt E protein of DENV serotype 1, 2, 3, 4 or 5. The peptides can be used for discriminating DENV serotype 1, 2, 3, 4 or 5 infections from other flaviviral infections in particular WNV, and/or TBEV or other DENV serotype infections or JEV infections.

In a particularly preferred embodiment, the T76R, Q77E, W101R, L107R quadruple mutant of the E protein of DENV serotype 2 may be used. The sequence of the DENV serotype 2 sequence is shown above. Therefore, in a particularly preferred embodiment, the present invention further relates to a mutant DENV, serotype 2 peptide of the invention having the sequence of amino acids 1 to 404 of SEQ ID No: 13, wherein the peptide has the following mutations: T76R, Q77E, W101R, L107R. Such ectodomain peptide of a loss-of-function E protein of DENV serotype 2 was successfully produced in insect cells, namely S2 cells, and was successfully used in the methods of the invention for distinguishing DENV serotype 2 infections in humans from other flaviviral infections, namely WNV and TBEV infections, as shown in Example S1 and FIG. 8.

For example, a recombinant peptide representing the ectodomain of a loss-of-function mutant of the E-protein of JEV may be used, as well as its corresponding wt peptide, i.e. the corresponding ectodomain peptide without mutations. The peptides can be used for discriminating JEV infections from other flaviviral infections in particular WNV, TBEV, usutu virus and/or DENV infections.

In a preferred embodiment of the invention, the mutant peptide of a specific flavivirus is used together with the recombinant peptide representing the ectodomain of the wildtype E-protein of such specific flavivirus.

The present invention further provides novel loss-of-function mutant proteins of the WNV E-protein, which are useful in the kits, uses and methods of the invention. In a preferred embodiment, such proteins have mutations at positions 76, 77, 101 and/or 107 of the WNV E protein. In a more preferred embodiment, such proteins have mutations at positions 76, 77, 101 and 107 of the WNV E protein, and optionally 1 to 40 further mutations at positions within the ectodomain, such as 1, 2, 3, 4, 5, 6, 7, 8, 9, 10, 15, 20, 25, 30, 35 or 40 further mutations at positions within the ectodomain, wherein such mutations at such further positions are preferably not within the fusion loop domain of the E protein. In a more preferred embodiment, such protein is a quadruple mutant having mutations at positions 76, 77, 101 and 107 of the WNV E protein.

The mutations at positions 76, 77, 101 and 107 as described herein are preferably independently selected from a deletion, insertion or substitution, in a more preferred embodiment, the mutations are all substitutions.

The further mutations are preferably independently selected from a deletion, insertion or substitution, in a more preferred embodiment, the further mutations are all substitutions.

Therefore, in a further embodiment, the present invention relates to the T76X1, M77X2, W101R, L107R mutant of the E protein of the West Nile Virus (WNV), wherein X1 is a naturally occurring amino acid except T and R, in particular X1 is a neutral or negatively charged amino acid, and wherein X2 is a naturally occurring amino acid except M and E, in particular X2 is a neutral or positively charged amino acid, in particular wherein the E protein without mutations comprises a sequence of a lineage 1 or lineage 2 WNV strain, more preferably wherein the E protein without mutations comprises a sequence (i) according to SEQ ID No: 1 and/or SEQ ID No: 4, or (ii) SEQ ID No: 20 and/or SEQ ID No: 21.

In a more preferred embodiment, X1 is selected from Glycine, Alanine, Valine, Leucine, Isoleucine, Serine, Cysteine, Methionine, Phenylalanine, Tyrosine, Tryptophan, Asparagine, Glutamine, Aspartate and Glutamate, most preferably X1 is Alanine.

In another more preferred embodiment, X2 is selected from Glycine, Alanine, Valine, Leucine, Isoleucine, Serine, Cysteine, Methionine, Phenylalanine, Tyrosine, Tryptophan, Asparagine, Glutamine, Histidine, Lysine, and Arginine, most preferably X2 is Glycine.

In a preferred embodiment of such mutant protein of the invention, the protein is produced recombinantly, more preferably produced recombinantly by bacterial expression, even more preferably by expression in *Escherichia coli*, and/or wherein the protein is purified after an oxidative refolding protocol.

In a preferred embodiment of such mutant protein of the invention, the protein exhibits a three-dimensional folding and/or is refolded after bacterial expression.

In another preferred embodiment of such mutant protein of the invention, the peptide the peptide is purified and/or is not part of a virus-like particle or a virus particle.

In a preferred embodiment of such mutant protein of the invention, the protein is glycosylated or unglycosylated, preferably unglycosylated.

The preferred embodiments of above mutant ectodomain peptides of the invention also apply to these mutant proteins of the invention.

In yet another embodiment, the present invention relates to mutant peptide selected from:

(i) the ectodomain of the mutant WNV E-protein of the invention described above, and (ii) amino acids 1-404 of the mutant WNV E-protein of the invention described above.

As described above in detail, the use of peptides relating to an ectodomain of the E protein of WNV is especially useful, as such peptides can be expressed and purified quickly and can be used an reliable immune-assay formats, without the need for complex systems, such as VLPs. Therefore, in a preferred embodiment of such mutant peptide of the invention, the peptide is produced recombinantly, more preferably produced recombinantly by bacterial expression, even more preferably by expression in *Escherichia coli*, and/or wherein the peptide is purified after an oxidative refolding protocol.

In a preferred embodiment of such mutant peptide of the invention, the peptide exhibits a three-dimensional folding and/or is refolded after bacterial expression.

In a preferred embodiment of such mutant peptide of the invention, the peptide is purified and/or is not part of a virus-like particle or a virus particle.

The preferred embodiments of above mutant ectodomain peptides of the invention also apply to these mutant ectodomain peptides of the invention.

Further, the invention may be applied to other flaviviruses. In particular, the invention further relates to a mutant ectodomain peptide of a flavivirus other than WNV, in particular of another clinically relevant flavivirus, preferably a flavivirus selected from dengue virus (DENV), tick-borne encephalitis virus (TBEV), Japanese encephalitis virus (JEV), usutu virus (USUV) and yellow fever virus (YFV). Such mutant peptide representing the ectodomain of an E protein of such flavivirus is preferably a loss-of-function mutant and/or contains mutations at positions 76, 77, 101 and 107 of the E protein, and/or contains mutations T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4, wherein Z1 is a naturally occurring amino acid except T for JEV, DENV, TBEV, usutu virus and except S for YFV, in particular Z1 is selected from A, G and R, and wherein Z2 is a naturally occurring amino acid except M for TBEV and except Q for DENV and except T for JEV, usutu virus and YFV, in particular Z2 is selected from A, G, S and E, and wherein Z3 is a naturally occurring amino acid except W, and wherein Z4 is a naturally occurring amino acid except L.

In an even more preferred embodiment, the mutant peptide representing the ectodomain is a quadruple mutant with mutations at positions 76, 77, 101 and 107 of the E protein of a DENV, TBEV, YFV, JEV or usutu virus and/or the mutant peptide representing the ectodomain is the quadruple mutant T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4 as compared to the corresponding wt ectodomain peptide; i.e. the mutant peptide contains the 4 mutations T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4 as compared to the corresponding wt ectodomain peptide, but does not contains further mutations.

Therefore, a yet further embodiment, the present invention relates to a mutant peptide representing the ectodomain of an E protein of a flavivirus selected from TBEV, dengue virus (DENV), wherein DENV is of serotype 1, 2, 3, 4 or 5, preferably of serotype 1, 2, 3 or 4, JEV, YFV and Usutu Virus, wherein positions 76, 77, 101 and 107 of the E protein are mutated. In a more preferred embodiment, the mutant peptide is a quadruple mutant, i.e. the peptide does not contain further mutations as compared to the corresponding E wt domain. In a yet further preferred embodiment, the ectodomain corresponds to amino acids 1 to 404 of the E protein of the virus. The positions may be mutated to any naturally occurring amino acids. Preferred mutations are described herein.

In a preferred embodiment, the flavivirus other than WNV is selected from TBEV and dengue virus (DENV), wherein DENV is of serotype 1, 2, 3, 4 or 5, preferably of serotype 1, 2, 3 or 4, JEV, YFV and Usutu Virus.

Therefore, in a further embodiment, the present invention relates to the T76Z1, M77Z2, W101Z3, L107Z4 mutant of the peptide representing the ectodomain of the E protein of a TBEV virus, or the T76Z1, Q77Z2, W101Z3, L107Z4 mutant of the peptide representing the ectodomain of the E protein of a dengue virus (DENV), in particular, wherein DENV is of serotype 1, 2, 3, 4 or 5, or the T76Z1, T77Z2, W101Z3, L107Z4 mutant of the peptide representing the ectodomain of the E protein of a JEV virus, or the the S76Z1, T77Z2, W101Z3, L107Z4 mutant of the peptide representing the ectodomain of the E protein of a YFV virus, or the T76Z1, T77Z2, W101Z3, L107Z4 mutant of the peptide representing the ectodomain of the E protein of an usutu virus, wherein Z1 is a naturally occurring amino acid except T for DENV, TBEV, usutu virus and JEV, and except S for YFV, in particular Z1 is selected from A, G and R, and wherein Z2 is a naturally occurring amino acid except M for TBEV and except Q for DENV and except T for JEV, usutu virus and YFV, in particular Z2 is selected from A, G, S and E, and wherein Z3 is a naturally occurring amino acid except W, and wherein Z4 is a naturally occurring amino acid except L.

In a more preferred embodiment, Z3 is R and/or Z4 is R, even more preferably Z3 and Z4 are both R.

In another preferred embodiment, Z1 is A or R.

In another preferred embodiment, Z2 is E or G.

In an even more preferred embodiment Z1 is A, Z2 is G, and Z3 and Z4 are both R, in particular wherein the virus is TBEV virus.

In a further even more preferred embodiment Z1 is A, Z2 is G, and Z3 and Z4 are both R, in particular wherein the virus is DENV virus. DENV may be of serotype 1, 2, 3, 4 or 5.

In an even more preferred embodiment Z1 is A, Z2 is G, and Z3 and Z4 are both R, in particular wherein the virus is JEV virus.

In an even more preferred embodiment Z1 is A, Z2 is G, and Z3 and Z4 are both R, in particular wherein the virus is usutu virus.

In an even more preferred embodiment Z1 is A, Z2 is G, and Z3 and Z4 are both R, in particular wherein the virus is YFV virus.

In a further more preferred embodiment Z1 is A, Z2 is E, and Z3 and Z4 are both R, in particular wherein the virus is TBEV virus.

In a further more preferred embodiment Z1 is A, Z2 is E, and Z3 and Z4 are both R, in particular wherein the virus is DENV virus. DENV may be of serotype 1, 2, 3, 4 or 5.

In a further more preferred embodiment Z1 is A, Z2 is E, and Z3 and Z4 are both R, in particular wherein the virus is JEV virus.

In a further more preferred embodiment Z1 is A, Z2 is E, and Z3 and Z4 are both R, in particular wherein the virus is usutu virus.

In a further more preferred embodiment Z1 is A, Z2 is E, and Z3 and Z4 are both R, in particular wherein the virus is YFV virus.

In a further more preferred embodiment Z1 is R, Z2 is E, and Z3 and Z4 are both R, in particular wherein the virus is TBEV virus.

In a further more preferred embodiment Z1 is R, Z2 is E, and Z3 and Z4 are both R, in particular wherein the virus is DENV virus. DENV may be of serotype 1, 2, 3, 4 or 5.

In a further more preferred embodiment Z1 is R, Z2 is E, and Z3 and Z4 are both R, in particular wherein the virus is JEV virus.

In a further more preferred embodiment Z1 is R, Z2 is E, and Z3 and Z4 are both R, in particular wherein the virus is usutu virus.

In a further more preferred embodiment Z1 is R, Z2 is E, and Z3 and Z4 are both R, in particular wherein the virus is YFV virus.

In a further more preferred embodiment Z1 is R, Z2 is G, and Z3 and Z4 are both R, in particular wherein the virus is TBEV virus.

In a further more preferred embodiment Z1 is R, Z2 is G, and Z3 and Z4 are both R, in particular wherein the virus is DENV virus. DENV may be of serotype 1, 2, 3, 4 or 5.

In a further more preferred embodiment Z1 is R, Z2 is G, and Z3 and Z4 are both R, in particular wherein the virus is JEV virus.

In a further more preferred embodiment Z1 is R, Z2 is G, and Z3 and Z4 are both R, in particular wherein the virus is usutu virus.

In a further more preferred embodiment Z1 is R, Z2 is G, and Z3 and Z4 are both R, in particular wherein the virus is YFV virus.

The ectodomain is preferably represented by amino acids 1 to 404 of the E protein of a flavivirus, in particular wherein the flavivirus is JEV, DENV, TBEV or usutu virus.

Therefore, in a further preferred embodiment of such mutant peptide of the invention, the mutant ectodomain has the sequence of amino acids 1-404 of the E protein with mutations T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4, wherein Z1 is a naturally occurring amino acid except T for JEV, DENV, TBEV, usutu virus, and except S for YFV, in particular Z1 is selected from A, G and R, and wherein Z2 is a naturally occurring amino acid except M for TBEV and except Q for DENV and except T for JEV, usutu virus and YFV, in particular Z2 is selected from A, G, S and E, and wherein Z3 is a naturally occurring amino acid except W, and wherein Z4 is a naturally occurring amino acid except L.

In a more preferred embodiment, Z3 is R and/or Z4 is R, even more preferably Z3 and Z4 are both R.

In another preferred embodiment, Z1 is A or R.

In another preferred embodiment, Z2 is E or G.

In an even more preferred embodiment Z1 is A, Z2 is G, and Z3 and Z4 are both R.

In a further more preferred embodiment Z1 is A, Z2 is E, and Z3 and Z4 are both R.

In a further more preferred embodiment Z1 is R, Z2 is E, and Z3 and Z4 are both R.

In a further more preferred embodiment Z1 is R, Z2 is G, and Z3 and Z4 are both R.

Therefore, in a yet further preferred embodiment, the present invention relates to a mutant peptide having a sequence of amino acids 1-404 of the quadruple mutant T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4 as compared to the corresponding wt E protein peptide; i.e. the mutant peptide contains the following four mutations at positions 76, 77, 101 and 107 as compared to the corresponding wt E protein peptide, but does not contains further mutations: T76Z1 (JEV, DENV, TBEV, usutu virus) or S76Z1 (YFV), M77Z2 (TBEV) or Q77Z2 (DENV) or T77Z2 (JEV, YFV, usutu virus), W101Z3, L107Z4.

In one more preferred embodiment, the E protein is a TBEV E protein. In a more preferred embodiment, the wildtype TBEV E protein, i.e. the E protein from TEBV virus without mutations, comprises the sequence according to SEQ ID No: 5.

In another more preferred embodiment, the E protein is a DENV E protein. In a more preferred embodiment, the wildtype DENV E protein, i.e. the E protein from dengue virus without mutations, comprises a sequence according to SEQ ID No: 6, 7, 8 or 9.

In a further embodiment, the present invention relates to a recombinant peptide representing the ectodomain of a loss-of-function mutant of the E-protein of a dengue, tick-borne encephalitis (TBEV), Japanese encephalitis (JEV), usutu virus (USUV) and/or yellow fever (YFV) virus.

The sequence of the E protein of the Usutu virus (Strain Vienna 2001) is disclosed in GenBank entry AAS59402:

(SEQ ID No: 17)

```
    fnclgms
301 nrdflegvsg atwvdvvleg dscitimakd kptidikmme teatnlaevr sycylatvsd
361 vstvsncptt geahnpkrae dtyvcksgvt drgwgngcglfgkgsidtca nftcslkamg
421 rmiqpenvky evgifihgst ssdthgnyss qlgasqagrf titpnspait vkmgdygeis
481 veceprngln teayyimsvg tkhflvhrew fndlalpwts passnwrnre illefeepha
541 tkqsvvalgs qegalhqala gavpvsfsgs vkltsghlkc rvkmekltlk gttygmctek
601 fsfaknpadt ghgtvvlelq ytgsdgpcki pisivaslsd ltpigrmvta npyvassean
661 akvlvemepp fgdsyivvgr gdkqinhhwh kagssigkaf ittikgaqrl aalgdtawdf
721 gsvggifnsv gkavhqvfgg afrtlfggms witqglmgal llwmgvnard rsialvmlat
781 ggvllflatn vha
```

The positions 76, 77, 101 and 107 corresponding to positions 76, 77, 101 and 107 in the ectodomain of the WNV E protein are shown bold and underlined.

Therefore, the present invention further relates in a further preferred embodiment to a mutant ectodomain peptide of the usutu virus E protein, comprising, more preferably having the following sequence:

Positions 76, 77, 101 and 107 are shown bold and underlined.

In a preferred embodiment, the wt E protein sequence of the YFV virus comprises SEQ ID No: 19. In a further preferred embodiment, the ectodomain of the wt E protein sequence of the YFV virus has the sequence of amino acids 1 to 404 of SEQ ID No: 19.

(SEQ ID No: 18)
```
    fnclgms 301 nrdflegvsg atwvdvvleg dscitimakd kptidikmme teatnlaevr sycylatvsd 361 vstvsncpZ1Z2 geahnpkrae dtyvcksgvt drgZ3gngcgZ4 fgkgsidtca
    nftcslkamg 421 rmiqpenvky evgifihgst ssdthgnyss qlgasqagrf titpnspait vkmgdygeis 481 veceprngln teayyimsvg tkhflvhrew fndlalpwts passnwrnre illefeepha 541 tkqsvvalgs qegalhqala gavpvsfsgs vkltsghlkc rvkmekltlk gttygmctek 601 fsfaknpadt ghgtvvlelq ytgsdgpcki pisivaslsd ltpigrmvta npyvassean 661 akvlvemepp fgdsyivvgr gdkqinhhwh kagssig,
``` wherein Z1, Z2, Z3 and Z4 are as defined above. In particular, Z2 is a naturally occurring amino acid except T, as the wt amino acid is T.

In a preferred embodiment, the wt E protein sequence of the usutu virus comprises SEQ ID No: 17. In a further preferred embodiment, the ectodomain of the wt E protein sequence of the usutu virus has the sequence of amino acids 1 to 404 of SEQ ID No: 17.

In yet a further preferred embodiment, the present invention relates to the T76R, Q77E, W101R, L107R quadruple mutant of the ectodomain of the E protein of DENV. DENV may be of serotype 1, 2, 3, 4 or 5, in particular DENV is of serotype 2. The corresponding wt sequence of the E protein is shown in SEQ ID No: 13.

The T76R, Q77E, W101R, L107R quadruple mutant of the ectodomain of the E protein of DENV serotype 2 has been shown to be particularly useful for distinguishing a DENV infection from a WNV and/or TBEV infection (see Example S1).

The N-terminal portion of the E protein of Yellow fever virus, encompassing the ectodomain is shown in Genbank entry AAA92706.1:

The mutant peptides of the invention relate to mutant loss-of-function peptides representing the ectodomain of the loss-of-function E protein mutants of a flavivirus.

In a yet further embodiment, also biologically active variants of the mutant peptides described herein are encompassed.

"Biologically active variants" of peptides are preferably understood as peptides which exhibit at least 70%, at least 80%, at least 90%, at least 91%, 92%, 93%, 94%, 95%, 96%, 97%, 98%, or 99% sequence identity to a mutant peptide described herein, in particular to a mutant peptide of the invention representing the ectodomain, and which are loss-of-function mutants as described above. For examples, it is known that amino acids at the N- or C-terminus of a peptide may be missing without affecting correct folding of the domain. For example, it is possible to also employ mutant WNV peptides which have sequence corresponding to amino acids 1-401 of the WNV E protein. As shown in the prior art, such peptide also folds correctly (Nybakken G E et al (2006, supra)). Also, the mutant peptides of the invention may contain 1 to 40 further mutations at positions within the ectodomain, such as 1, 2, 3, 4, 5, 6, 7, 8, 9, 10, 15, 20, 25, (SEQ ID No: 19)
```
    ahcigitdrd fiegvhggtw vsatleqdkc vtvmapdkps ldisletvai dgpaearkvc 61 ysavltnvki ndkcpstgea hleeenegdn ackrtysdrg wgngcglfgk gsivacakft 121 caksmslfev dqtkiqyvir aqlhvgakqe nwntdiktlk fdalsgsqea eftgygkatl 181 ecqvqtaldf snsyiaemek eswivdkqwa qdltlpwqsg sggvwremhh lvefepphaa 241 tikvlalgnq egslktaltg amrvtkdtnn sklyklhggh vacrvklsal tlkgtsykmc 301 tdkmsfvknp tdtghgtavm qvkvpkgapc ripvmvaddl taavnkgilv tvnpiastnd 361 devlievnpp fgdsyiivgt gdsrltyqwh kegssigklf tqtmkgaerl avmgdaawdf 421 gsaggfftsv gkgihtvfgs afqglfggls witkvimgvv liwvgintrn mtmsmsmilv 481 gvimmflslg vga
```

In positions 76, 77 (p s t) and 101, 107 (w g l) are shown bold and underlined.

30, 35 or 40 further mutations, in particular substitutions, at positions within the ectodomain, wherein such mutations at such further positions are preferably not within the fusion loop domain of the E protein.

Sequence identity can preferably be determined using the sequence comparison program NCBI-BLAST2 (Altschul et al., Nucleic Acids Res. 25:3389-3402 (1997)). NCBI-BLAST2 uses several search parameters, wherein all of those search parameters are set to default values including, for example, unmask=yes, strand=all, expected occurrences=10, minimum low complexity length=15/5, mufti-pass e-value=0.01, constant for mufti-pass=25, dropoff for final gapped alignment=25 and scoring matrix=BLOSUM62.

Therefore, in one further embodiment, the invention also relates to a mutant WNV peptide with the sequence of amino acids 1 to 403, 1 to 402, 1 to 401, 1 to 400 or 1 to 399 of SEQ ID No: 2.

Therefore, in a further embodiment, the invention also relates to a mutant WNV peptide with the sequence of amino acids 2 to 404, 3 to 404, 4 to 404, 5 to 404 or 6 to 404 of SEQ ID No: 2.

Similarly, combinations of N- and C-terminal deletions are possible, such as a mutant WNV peptide with the sequence of amino acids 2 to 403, 3 to 401, 4 to 400, 5 to 401 or 6 to 402 of SEQ ID No: 2.

Typically, the corresponding wt peptides are used in kits, methods and uses of the invention.

Therefore, in a further embodiment, the present invention also relates to biologically active variants of mutant peptides of the invention described herein. Such variants may have N-terminal and/or C-terminal deletions, in particular as compared to the ectodomain sequence. Also, it is possible, that such peptides may contain one or more further moieties, which may be attached covalently or non-covalently. Also, such moieties may be attached N-terminally and/or C-terminally and/or to an amino acid side chain, preferably N-terminally and/or C-terminally.

In a further embodiment, the present invention relates to a biologically active variant of a mutant peptide of the invention as described herein, wherein
  1, 2, 3, 4, or 5 of the N-terminal amino acids of the peptide are deleted, and/or
  1, 2, 3, 4, or 5 of the C-terminal amino acids of the peptide are deleted, and/or
  the peptide further contains one or more further moieties, preferably 1, 2, 3, 4 or 5 of amino acids of the homologous protein sequence, a heterologous peptide tag, such as a purification tag, a labeling moiety, such as a fluorescent moiety, and/or a separation moiety, such as a biotin moiety and/or
  the peptide contains 1 to 40 further mutations at positions within the ectodomain.

In one preferred embodiment, 1, 2, 3, 4, or 5 of the N-terminal amino acids of the ectodomain peptide are deleted, and 1, 2, 3, 4, or 5 of the C-terminal amino acids of the peptide are deleted, in particular as compared to the ectodomain sequence.

In another preferred embodiment, 1, 2, 3, 4, or 5 of the N-terminal amino acids of the peptide are deleted, and none of the C-terminal amino acids of the peptide are deleted, in particular as compared to the ectodomain sequence.

In yet another embodiment, 1, 2, 3, 4, or 5 of the C-terminal amino acids of the peptide are deleted, and none of the N-terminal amino acids of the peptide are deleted, in particular as compared to the ectodomain sequence.

In another such peptides may contain one or more further moieties, in particular as compared to the ectodomain sequence, which moieties may be attached covalently or non-covalently. Also, such moieties may be attached N-terminally and/or C-terminally and/or to an amino acid side chain, preferably N-terminally and/or C-terminally.

For example, 1, 2, 3, 4 or 5 of amino acids of the homologous protein sequence may be further present as compared to the ectodomain sequence. As the ectodomain sequence of the WNV E protein corresponds to amino acids 1-404 of the WNV E protein, amino acids 405, 405-406, 405-407, 405-408 or 405-409 may further be present C-terminally, covalently attached to amino acid 404 via a peptide bond. Such peptides may be generated by recombinant expression using methods known in the art, as described above.

In a further preferred embodiment, a heterologous peptide tag may be present, such as a purification tag. For example, a His-tag, FLAG-tag, myc-tag, GST-tag, HA-tag or v5-tag. Such tags may be used for detection and/or purification of a peptide by methods skilled in the art. Such tags may be present N-terminally and/or C-terminally, preferably C-terminally.

In another preferred embodiment, a labeling moiety may be present. Such moieties may be attached N-terminally and/or C-terminally and/or to an amino acid side chain. Such labeling moiety substance is capable of producing a signal via direct or indirect detection. The labeling moiety thus may be detected directly or indirectly. For direct detection, a labeling moiety can be selected from any known detectable marker group, like chromogens, fluorescent groups, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of labeling moieties are luminescent metal complexes, such as ruthenium or europium complexes, e.g. as used for ECLIA, enzymes, e.g. as used for ELISA, and radioisotopes; e.g. as used for RIA.

Indirect detection systems comprise, for example, that the peptide labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g. by the labeling moiety as mentioned above.

A particularly preferred labeling moiety is a fluorescent moiety e.g. fluorescein, coumarin, Cy3, Cy5, rhodamine, oxazine, resorufin, cyanine and derivatives thereof.

Depending on the chemical nature of the labeling moiety, the attachment is preferably performed N-terminally, C-terminally or to an amino acid side chain.

In a further preferred embodiment, a separation moiety, such as a biotin moiety may be present. A separation moiety is preferably understood as moiety allowing specific separation of the peptide from a solution comprising such peptide. For example, the peptide may be labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is attached to a solid support, such as an array, chip, well plate or bead, such as a magnetic bead, thereby allowing separation.

In one preferred embodiment, the mutant peptides of the invention contain 1 to 40 further mutations at positions within the ectodomain, such as 1, 2, 3, 4, 5, 6, 7, 8, 9, 10, 15, 20, 25, 30, 35 or 40 further mutations, in particular substitutions, at positions within the ectodomain, wherein such mutations at such further positions are preferably not within the fusion loop domain of the E protein.

In the kits of the invention, the wt peptides have a sequence corresponding to the sequence of the mutant peptide. For example, in case a mutant WNV peptide with the sequence of amino acids 1 to 401 of SEQ ID No: 2 is used, it is preferred that the corresponding wt peptide having the sequence of amino acids 1 to 401 of the wt E protein WNV is present and used in kits of the invention.

In case the mutant peptide further contains one or more further moieties, it is possible that the corresponding wt peptide also contains the one or more further moieties, or that the one or more further moieties are absent in the wt peptide. However, it is preferred, that also the wt peptide further contains the one or more further moieties present in the mutant peptides of the kits.

Therefore, in a further embodiment, the present invention relates to a kit comprising, preferably consisting of:
(a) at least one peptide representing the ectodomain of a mutated E protein of a specific flavivirus of the invention as described herein or a biologically active variant thereof, and optionally
(b) at least one peptide representing the ectodomain of the wildtype E protein of the same flavivirus, wherein optionally
1, 2, 3, 4, or 5 of the N-terminal amino acids of the ectodomain sequence are deleted, and/or
1, 2, 3, 4, or 5 of the C-terminal amino acids of the ectodomain sequence are deleted, and/or
the wildtype peptide further contains one or more further moieties,
preferably 1, 2, 3, 4 or 5 of amino acids of the homologous protein sequence, a heterologous peptide tag, such as a purification tag, a labeling moiety, such as a fluorescent moiety, and/or a separation moiety, such as a biotin moiety
the peptide contains 1 to 40 mutations at positions within the ectodomain.

In case the wt peptide contains mutations at positions within the ectodomain, such mutations preferably correspond to the "further" mutations in the mutated peptide of (a) and/or such mutations at such positions are preferably not within the fusion loop domain of the E protein.

In one preferred embodiment, the kit does not comprise a peptide of (b), in an even more preferred embodiment, the kit consists of the at least one mutant peptide of (a).

In another preferred embodiment, the kit comprises a peptide of (b).

The wt peptide may contain 1, 2, 3, 4, 5, 6, 7, 8, 9, 10 or more, preferably 1, 2, 3 or 4 further moieties, respectively.

Such one or more further moieties are preferably selected from (a) 1, 2, 3, 4 or 5 of amino acids of the homologous protein sequence, (b) a heterologous peptide tag, such as a purification tag, (c) a labeling moiety, such as a fluorescent moiety, and/or (d) a separation moiety, such as a biotin moiety.

In a preferred embodiment of such kit of the invention, or a mutant peptide of the invention as described herein, the peptide, or the at least one peptides are bound to one or more solid support(s), preferably wherein the solid support is selected from a plate, a well plate, an array, such as a microarray or nanoarray, or a bead, such as a magnetic bead.

In one preferred embodiment, the solid support does not comprise a peptide of (b), in an even more preferred embodiment, only the at least one mutant peptide or a biologically active variant thereof of (a) is bound to the solid support.

In a further embodiment, the present invention relates to the use of a mutant peptide of the invention or a biologically active variant thereof, or of a kit of the invention as described above, for discriminating infections with a specific flavivirus from infections with other flavivirus(es), preferably from infections with other clinically relevant flavivirus infections.

The preferred embodiments of such kits and uses are as described above for the other kits and uses of the invention.

In one preferred embodiment, the peptide, or the peptide in the kit is a mutated WNV peptide of the invention or a biologically active variant thereof as described above, in particular the T76A, M77G, W101R, L107R quadruple mutant of the ectodomain of the E protein of the West Nile Virus (WNV), and wherein a WNV infection can be discriminated from infections with TBEV and/or DENV and/or JEV.

In another preferred embodiment, the peptide, or the peptide in the kit is a mutated DENV peptide of the invention or a biologically active variant thereof, and wherein a DENV infection can be discriminated from infections with TBEV and/or WNV and/or JEV. In particular, the T76A, Q77G, W101R, L107R quadruple mutant of the E protein of DENV serotype 1, 2, 3, 4 or 5 or the T76R, Q77E, W101R, L107R quadruple mutant of the ectodomain of the E protein of DENV serotype 1, 2, 3, 4 or 5, in particular serotype 2, may be used.

In another preferred embodiment, the peptide, or the peptide in the kit is a mutated TBEV peptide or a biologically active variant thereof, preferably the T76A, M77G, W101R, L107R quadruple mutant of the ectodomain of the E protein of the TBEV virus, and wherein a TBEV infection can be discriminated from infections with WNV and/or DENV and/or JEV.

In one embodiment, the kits and solid supports of the invention contain 1, 2, 3, 4, 5, 6, 7, 8, 9, 10 or more of "couples" of mutant peptides or biologically active variants thereof of a specific flavivirus and the corresponding wt peptide of the specific flavivirus. For example, a kit or solid support of the invention may contain:
(a) the T76A, M77G, W101R, L107R quadruple mutant of the ectodomain of the E protein of the West Nile Virus (WNV) and its corresponding wt ectodomain WNV peptide, as described above, and
(b1) the T76A, Q77G, W101R, L107R quadruple mutant of the E protein of DENV serotype 1, 2, 3, 4 or 5 and its corresponding wt ectodomain DENV peptide, as described above, and/or (b2) the T76A, M77G, W101R, L107R quadruple mutant of the ectodomain of the E protein of the TBEV virus and its corresponding wt ectodomain TBEV peptide, and/or (b3) the T76R, Q77E, W101R, L107R quadruple mutant of the ectodomain of the E protein of DENV serotype 1, 2, 3, 4 or 5, in particular serotype 2, and its corresponding wt ectodomain DENV peptide.

In one embodiment, the kits and solid supports of the invention contain 1, 2, 3, 4, 5, 6, 7, 8, 9, 10 or more of "couples" of mutant peptides or biologically active variants thereof of a specific flavivirus and the corresponding wt peptide of the specific flavivirus. For example, a kit or solid support of the invention may comprise, preferably consist of:

(a) the T76A, M77G, W101R, L107R quadruple mutant of the ectodomain of the E protein of the West Nile Virus (WNV) and its corresponding wt ectodomain WNV peptide, as described above, and (b1) the T76A, Q77G, W101R, L107R quadruple mutant of the E protein of DENV serotype 1, 2, 3, 4 or 5 and its corresponding wt ectodomain DENV peptide, as described above, and/or (b2) the T76A, M77G, W101R, L107R quadruple mutant of the ectodomain of the E protein of the TBEV virus and its corresponding wt ectodomain TBEV peptide, and/or (b3) the T76R, Q77E, W101R, L107R quadruple mutant of the ectodomain of the E protein of DENV serotype 1, 2, 3, 4 or 5, in particular serotype 2, and its corresponding wt ectodomain DENV peptide as described above, more preferably the kit or solid support comprises, preferably consists of (a) and (b3).

In yet another embodiment, the kits and solid supports of the invention contain 2, 3, 4, 5, 6, 7, 8, 9, 10 or more different mutant peptides or biologically active variants thereof for 2, 3, 4, 5, 6, 7, 8, 9, 10 or more different specific flaviviruses. For example, a kit or solid support of the invention may comprise, preferably consist of:

(a) the T76A, M77G, W101R, L107R quadruple mutant of the ectodomain of the E protein of the West Nile Virus (WNV), and (b) the T76R, Q77E, W101R, L107R quadruple mutant of the ectodomain of the E protein of DENV serotype 2.

In yet another embodiment, the kits and solid supports of the invention contain 2, 3, 4, 5, 6, 7, 8, 9, 10 or more different mutant peptides or biologically active variants thereof for 2, 3, 4, 5, 6, 7, 8, 9, 10 or more different specific flaviviruses. For example, a kit or solid support of the invention may comprise, preferably consist of:

(a) the T76A, M77G, W101R, L107R quadruple mutant of the ectodomain of the E protein of the West Nile Virus (WNV), and (b1) the T76A, Q77G, W101R, L107R quadruple mutant of the E protein of DENV serotype 1, 2, 3, 4 or 5, and/or (b2) the T76A, M77G, W101R, L107R quadruple mutant of the ectodomain of the E protein of the TBEV, and/or (b3) the T76R, Q77E, W101R, L107R quadruple mutant of the ectodomain of the E protein of DENV serotype 2, more preferably the kit or solid support comprises, preferably consists of (a) and (b3).

In a further embodiment, the present invention relates to a method for discriminating infections with a specific flavivirus from infections with other flavivirus(es) in an immune-assay, preferably ELISA assay, using the mutant peptides of the invention or biologically active variants thereof and the corresponding wt peptides.

Therefore, in a further embodiment, the present invention relates to a method for discriminating infections with a specific flavivirus from infections with other flavivirus(es), preferably with other clinically relevant flavivirus infections, comprising the steps:

(1) contacting at least one mutant peptide representing the ectodomain of a mutant E protein of a specific flavivirus of the invention or a biologically active variant thereof
with antibodies binding to the specific flavivirus from an animal sample, (2) contacting at least one wildtype peptide representing the ectodomain of the wildtype E protein of the specific flavivirus of step (1)
with antibodies binding to the specific flavivirus from an animal sample, wherein optionally
1, 2, 3, 4, or 5 of the N-terminal amino acids of the ectodomain sequence are deleted, and/or
1, 2, 3, 4, or 5 of the C-terminal amino acids of the ectodomain sequence are deleted, and/or
the wildtype peptide further contains one or more further moieties, preferably 1, 2, 3, 4 or 5 of amino acids of the homologous protein sequence, a heterologous peptide tag, such as a purification tag, a labeling moiety, such as a fluorescent moiety, and/or a separation moiety, such as a biotin moiety, and/or
the peptide contains 1 to 40 mutations at positions within the ectodomain, (3) determining the amount of mutant peptide-antibody complex formed in step (1), and the amount of wildtype peptide-antibody complex formed in step (2), (4) determining the ratio (a)/(b) between the amounts measured in step (3) for (a) the wildtype peptide of step (2), and (b) the mutant peptide of step (1), wherein an elevated ratio (a)/(b), in particular a ratio above about 1.22, above about 2, above about 2.5, above about 3, above about 4, above about 4.5 above about 5, above about 5.5 or above about 6, indicates that the animal is not infected with the specific flavivirus, or wherein a low ratio (a)/(b), in particular a ratio of about 2 or lower, of about 1.7 or lower, of about 1.5 or lower, of about 1.3 or lower, or of about 1.2 or lower indicates that the animal is infected with the specific flavivirus.

The peptides are contacted with antibodies binding to the specific flavivirus from an animal sample, in particular bird or mammalian sample, such as a human sample. This is typically performed by adding either a solution containing a peptide to the animal sample or a solid support, to which antibodies from the animal sample are bound, e.g. by pumping, pipetting or capillary forces, or, by adding an animal sample to the peptides, depending on the assay format.

In case of a non-capture ELISA assay, the peptides are preferably bound to a solid support, and an optionally diluted animal sample, such as a diluted serum or blood sample, is added thereto e.g. by pumping, pipetting or capillary forces. In this embodiment, the solid support is preferably coated with at least one wildtype peptide on (an) area(s) spatially distinct from the area(s) coated with at least one mutant peptide.

Typically, one or more washing steps, e.g. with an aqueous buffered solution, are performed after each step to allow for removal of unbound or unspecifically bound entities.

The contacting is preferably performed under conditions conducive to the formation of antibody-peptide complexes.

Preferably, the peptides and antibodies are incubated for at least 10 min, at least 30 min, at least 1 or at least 1.5 hours.

Preferably, the pH in the contacting solution is between 5.5 to 8.5, more preferably between 6.5 and 7.8.

Preferably, the method is performed at a temperature between 15° C. and 40°, more preferably between 20° C. and 38° C., even more preferably at about 25° C. or room temperature.

According to the invention, the amount of mutant peptide-antibody complex formed in step (1), and the amount of wildtype peptide-antibody complex formed in step (2) is determined. Various assays known in the art are suitable therefore, such as an enzyme-linked immunoassay (ELISA), more preferably capture ELISA, an (electro-) chemiluminescence immunoassay (ECLIA), and a radioimmunoassay (RIA). Further preferred assays are sandwich fluorescence immunoassay (FIA), and Microparticle capture enzyme immunoassay (MEIA). Also, the assay may be in the form of test strips.

In a particularly preferred embodiment, the method employs an ELISA or capture ELISA assay. Capture ELISA is preferably also known as sandwich ELISA.

In step (4), the ratio (a)/(b) between the amounts measured in step (3) for (a) the wildtype peptide of step (2), and (b) the mutant peptide of step (1) is determined.

Therefore, following ratio is determined for the above method of the invention:

$$\text{ratio} = \frac{\text{amount of wildtype peptide} - \text{antibody complex formed in step (2)}}{\text{amount of mutant peptide} - \text{antibody complex formed in step (1)}}$$

As shown in the Examples for an ELISA assay with confirmed human WNV serum samples, confirmed human DENV serum samples and confirmed human TBEV serum samples, and mutant a WNV peptide of the invention, an elevated ratio (a)/(b), indicates that the human from whom the sample was obtained is not infected with WNV, whereas a low ratio (a)/(b) indicates that the human is infected with the specific flavivirus: for WNV samples, a low value of 1.22±0.2 was determined. Therefore, a low value is preferably a value close to 1, such as a ratio of about 2 or lower, of about 1.7 or lower, of about 1.5 or lower, of about 1.3 or lower, or of about 1.2 or lower.

For confirmed DENV samples and TBEV samples, ratios of 5.92±3.1 and 6.06±2.1, respectively, were determined. These are ratio values which are elevated, i.e. which are clearly higher than 1. Such elevated ratios, in particular a ratio above about 1.22, above about 2, above about 2.5, above about 3, above about 4, above about 4.5 above about 5, above about 5.5 or above about 6, indicate that the animal from whom the sample was obtained is not infected with WNV.

In a preferred embodiment of the method of the invention, determining the amount of mutant peptide-antibody complex formed in step (1), and the amount of wildtype peptide-antibody complex formed in step (2) is performed by an ELISA assay.

In case of a ELISA assay without initially capturing antibodies, like an ELISA assay as described in the examples, the amount of mutant peptide-antibody complex formed in step (1), and the amount of wildtype peptide-antibody complex formed in step (2) are determined by a suitable secondary antibody binding to an animal antibody may be used, such as an anti-mammalian IgG or anti-mammalian IgM antibody, or anti-mammalian IgA-antibody, in case of a mammalian sample, preferably an anti-human IgG or anti-human IgM antibody, or anti-human IgA-antibody, in case of a human sample, or as an anti-bird IgA antibody in case of a bird sample, wherein the secondary antibody described above is preferably labeled for detection. In case of an ELISA, the secondary is in one preferred embodiment labeled with an enzyme, such as HRP. Quantification may be performed by using a substrate such as TMB and an ELISA reader. In a further embodiment, the secondary antibody is in turn detected using a third antibody, which specifically binds to the secondary antibody. In this embodiment, the third antibody is preferably labelled with a detectable label, such as an enzyme. An ELISA assay wherein a secondary antibody is detected by a third antibody which in turn is labelled with a detectable label is shown in Example S2.

In such preferred embodiment, the method may be performed by:

- providing at least one mutant peptide and at least one wildtype peptide of steps (1) and (2) bound to a solid support, and
- determining the amounts of mutant peptide-antibody complexes and wildtype peptide-antibody complexes by a secondary antibody.

For example, the secondary antibody is an goat anti-human IgM antibody, or goat anti-human IgG-antibody, and the third antibody is a labelled antibody specifically binding to the goat anti-human IgM antibody, or the goat anti-human IgG-antibody.

In case the secondary antibody is labelled with an enzyme, such as HRP, a substrate such as TMB may be added, and incubated. Absorbance at a suitable wavelength, such as 450 nm and 520 nm for TMB may then be measured in an ELISA reader.

In case of a capture ELISA assay, a capture antibody specific for an antigen, such as anti-human IgA antibody, anti-human IgG or anti-human IgM antibody is bound to a solid support such as a well on a plate. In the present invention, the antigen captured by such anti-human IgA or anti-human IgG or anti-human IgM antibody is human IgA, human IgG or human IgM respectively in case the sample is a human sample. In the present invention, the antigen captured by an anti-horse IgA or anti-horse IgG or anti-horse IgM antibody is horse IgA, horse IgG or horse IgM, respectively, in case the sample is a horse sample.

In the preferred embodiment of a capture assay, in particular, a capture ELISA, the antibodies, such as IgA, IgM and/or IgG, or IgY antibodies from the animal sample, such as bird serum or mammalian, preferably human serum, are preferably bound to a solid support, in particular by using a solid support coated with an antibody capturing such antibodies, such as anti-human IgM and/or IgG antibodies in case of a human sample. An optionally diluted animal sample is added to such capturing support e.g. by pumping, pipetting or capillary forces. The peptides are typically added in form of a solution, such as a buffered aqueous solution. In this embodiment, the at least one wildtype peptide is preferably added on (an) area(s) spatially distinct from the area(s) to which at least one mutant peptide added.

For example, the different peptides may be added to different spots on an array or different wells of a well plate.

The use of a capture ELISA is particularly preferred for capturing human IgM antibodies, however, it is also possible to detect other isotypes like IgA, IgY- or IgG antibodies in a capture assay, as described above.

In another preferred embodiment of the method of the invention, determining the amount of mutant peptide-antibody complex formed in step (1), and the amount of wildtype peptide-antibody complex formed in step (2) is performed by a capture assay.

In such preferred embodiment, the method may be performed by:
- providing capture antibodies bound to a solid support,
- contacting the animal sample with the capture antibodies bound to a solid support, whereby antibody-antibody complexes bound to a solid support are formed,
- contacting the at least one mutant peptide and the at least one wildtype peptide of steps (1) and (2) with the antibody-antibody complexes bound to the solid support, and
- determining the amounts of mutant peptide-antibody complexes and wildtype peptide-antibody complexes by an optionally labeled secondary antibody,
    - more preferably wherein optionally labeled secondary antibody specifically recognizes an epitope on the wildtype and mutant peptides, which is at least 5, 10, or 15 amino acids distant from the fusion loop domain, in particular wherein the fusion loop domain corresponds to amino acids 63 to 120 of the E protein of a flavivirus.

Capture antibodies are preferably understood as antibodies which specifically bind to an isotype of antibody of the animal. For example, the capture antibody is an anti-human IgG- or anti-human IgM-antibody or anti-human IgA-antibody in the case the sample is a human sample. For example, the capture antibody is an anti-bird IgY-antibody in the case the sample is a bird sample.

The capture antibodies bound to a solid support may be obtained by methods known in the art, for example by using a bioaffine binding pair, or by coating a support such as plate in the presence of a coating buffer, as described in the examples for peptides.

The contacting of the at least one mutant peptide and the at least one wildtype peptide of steps (1) and (2) with the antibody-antibody complexes bound to the solid support may be performed by methods known in the art, in particular by adding a solution containing a peptide to the solid support, to which the antibodies from the animal sample are bound, e.g. by pumping, pipetting or capillary forces.

Typically, one or more washing steps, e.g. with an aqueous buffered solution, are performed after each step to allow for removal of unbound or unspecifically bound entities.

The contacting is preferably performed under conditions conducive to the formation of antibody-peptide complexes.

Preferably, the peptides and antibodies are incubated for at least 10 min, at least 30 min, at least 1 or at least 1.5 hours.

Preferably, the pH in the contacting solution is between 5.5 and 8.5, more preferably between 6.5 and 7.8.

Preferably, the method is performed at a temperature between 15° C. and 40°, more preferably between 20° C. and 38° C., even more preferably at about 25° C. or room temperature.

The amounts of mutant peptide-antibody complexes and wildtype peptide-antibody complexes are preferably determined by a suitable, optionally labeled, secondary antibody. A suitable secondary antibody recognizes both the mutant peptide and the corresponding wt peptide to a comparable extent, i.e. the Kd value for the binding of the secondary antibody to the mutant peptide differs by 20% or less, preferably by 20% or less from the Kd value for the binding of the secondary antibody to the corresponding wt peptide.

Preferably, the secondary antibody specifically recognizes an epitope on the wildtype and mutant peptides, which is at least 5, 10, or 15 amino acids distant from the fusion loop domain, in particular wherein the fusion loop domain corresponds to amino acids 63 to 120 of the E protein of a flavivirus. Thereby, such secondary antibody recognizes both the mutant peptide and the wt peptide to a comparable extent. In one preferred embodiment, the secondary antibody recognizes an epitope within domain DIII of the peptide.

The secondary antibody is preferably labeled. The same preferred embodiments apply as for other secondary antibodies and the detection steps therefore, as described above. Alternatively, the secondary antibody is detected by a suitable third antibody, which is preferably labelled.

In a further embodiment, the present invention relates an IgM capture assay for discriminating acute infections with a specific flavivirus from acute infections with other flaviviruses. Preferably, in this assay, IgM antibodies from a mammalian sample, in particular human or horse sample, are captured, using a solid support to which anti-mammalian IgM antibodies, in particular anti-human IgM antibodies or anti-horse IgM antibodies are bound, as described above.

The mutant peptides of the invention or biologically active variants thereof and the corresponding wt peptides are contacted with the solid support(s) to which the antibodies from the sample are bound or captured. This allows formation of the respective peptide-antibody complexes captured on the solid support(s). In order determine binding, the mutant peptides on the one hand and the wt peptides on the other hand are added to on non-overlapping areas of a solid support, e.g. by pipetting or pumping to distinct wells or spots, depending on the solid support.

The same preferred embodiments as for the above methods of the invention apply.

As described above, the amounts of mutant peptide-antibody complexes and wildtype peptide-antibody complexes are determined by using a suitable optionally labelled secondary antibody, which recognizes both the mutant peptide and the corresponding wt peptide to a comparable extent.

In a further embodiment, the present invention relates to a method for discriminating acute infections with a specific flavivirus from acute infections with other flavivirus(es), preferably from acute infections with other clinically relevant flaviviruses, comprising the steps:
- (1) providing at least one solid support to which anti-mammalian IgM antibodies are bound,
- (2) contacting the solid support with a mammalian sample containing or suspected to contain antibodies binding to a specific flavivirus, in particular wherein the mammalian sample is serum or cerebrospinal fluid,
- (3) contacting at least one peptide representing the ectodomain of a mutated E protein of a specific flavivirus of the invention or a biologically active variant thereof with at least one solid support of step (2), whereby mutant peptide-antibody complexes are allowed to form,
- (4) contacting at least one peptide representing the ectodomain of the wildtype E protein of the specific flavivirus, wherein optionally 1, 2, 3, 4, or 5 of the N-terminal amino acids of the ectodomain sequence are deleted, and/or 1, 2, 3, 4, or 5 of the C-terminal amino acids of the ectodomain sequence are deleted, and/or the wildtype peptide further contains one or more further moieties, preferably 1, 2, 3, 4 or 5 of amino acids of the homologous protein sequence, a heterologous peptide tag, such as a purification tag, a labeling moiety, such as a fluorescent moiety, and/or a separation moiety, such as a biotin moiety, and/or the peptide contains 1 to 40 mutations at positions within the ectodomain, with at least one solid support of step (2), whereby wildtype peptide-antibody complexes are allowed to form, with the proviso that the contacting of steps (3) and (4) takes place on non-overlapping areas of a solid support, (5) determining the amounts of mutant peptide-antibody complexes and wildtype peptide-antibody complexes by using an optionally labelled secondary antibody, more preferably wherein the optionally labeled secondary antibody specifically recognizes an epitope on the wildtype and mutant peptides, which is at least 5, 10, or 15 amino acids distant from the fusion loop domain, in particular wherein the fusion loop domain corresponds to amino acids 63 to 120 of the E protein of a flavivirus, (6) determining the ratio (a)/(b) between the amounts determined in step (5) for (a) the wildtype peptide of step (4) and (b) the mutant peptide of step (3), wherein an elevated ratio (a)/(b), in particular a ratio above about 1.22, above about 2, above about 2.5, above about 3, above about 4, above about 4.5 above about 5, above about 5.5 or above about 6, indicates that the mammal is not acutely infected with the specific flavivirus, or wherein a low (a)/(b), in particular a ratio of about 2 or lower, of about 1.7 or lower, of about 1.5 or lower, of about 1.3 or lower, or of about 1.2 or lower indicates that the mammal is acutely infected with the specific flavivirus.

In a preferred embodiment, the mammal is a human or a horse, in particular a human.

In a further embodiment, the present invention relates to a method for discriminating infections with a specific flavivirus from infections with other flavivirus(es), preferably from acute infections with other clinically relevant flaviviruses, comprising the steps:

(1) providing at least one solid support to which capture antibodies are bound, (2) contacting the solid support with an animal sample containing or suspected to contain antibodies binding to a specific flavivirus, in particular wherein the animal sample is serum or cerebrospinal fluid, (3) contacting at least one peptide representing the ectodomain of a mutated E protein of a specific flavivirus of the invention or a biologically active variant thereof with at least one solid support of step (2), whereby mutant peptide-antibody complexes are allowed to form, (4) contacting at least one peptide representing the ectodomain of the wildtype E protein of the specific flavivirus, wherein optionally 1, 2, 3, 4, or 5 of the N-terminal amino acids of the ectodomain sequence are deleted, and/or 1, 2, 3, 4, or 5 of the C-terminal amino acids of the ectodomain sequence are deleted, and/or the wildtype peptide further contains one or more further moieties, preferably 1, 2, 3, 4 or 5 of amino acids of the homologous protein sequence, a heterologous peptide tag, such as a purification tag, a labeling moiety, such as a fluorescent moiety, and/or a separation moiety, such as a biotin moiety with at least one solid support of step (2), and/or the peptide contains 1 to 40 mutations at positions within the ectodomain, whereby wildtype peptide-antibody complexes are allowed to form, with the proviso that the contacting of steps (3) and (4) takes place on non-overlapping areas of a solid support, (5) determining the amounts of mutant peptide-antibody complexes and wildtype peptide-antibody complexes by using an optionally labelled secondary antibody, more preferably wherein the optionally labeled secondary antibody specifically recognizes an epitope on the wildtype and mutant peptides, which is at least 5, 10, or 15 amino acids distant from the fusion loop domain, in particular wherein the fusion loop domain corresponds to amino acids 63 to 120 of the E protein of a flavivirus, (6) determining the ratio (a)/(b) between the amounts determined in step (5) for (a) the wildtype peptide of step (4) and (b) the mutant peptide of step (3), wherein an elevated ratio (a)/(b), in particular a ratio above about 1.22, above about 2, above about 2.5, above about 3, above about 4, above about 4.5 above about 5, above about 5.5 or above about 6, indicates that the mammal is not infected with the specific flavivirus, or wherein a low (a)/(b), in particular a ratio of about 2 or lower, of about 1.7 or lower, of about 1.5 or lower, of about 1.3 or lower, or of about 1.2 or lower indicates that the animal is infected with the specific flavivirus.

In case the animal is a mammal, and the capture antibodies may be anti-mammal IgA antibodies, or anti-mammal IgG antibodies or anti-mammal IgM-antibodies. In case the animal is a human, and the capture antibodies may be anti-human IgA antibodies, or anti-human IgG antibodies or anti-human IgM-antibodies. In case the animal is a bird, and the capture antibodies may be anti-bird IgY antibodies. As shown in Example S2, an anti-human IgM antibody may also be suitable for binding to monkey IgM.

In case the secondary antibody in methods of the invention is labelled with a radioisotope, radiation may be measured. In this embodiment, the assay is a RIA.

In a preferred embodiment of above methods of the invention, the specific flavivirus is selected from West Nile Virus (WNV), dengue virus (DENV), in particular serotype 1, 2, 3, 4, or 5, tick-borne encephalitis virus (TBEV), Japanese encephalitis virus (JEV), usutu virus (USUV) and yellow fever virus (YFV), more preferably selected from West Nile Virus (WNV), dengue virus (DENV), in particular serotype 1, 2, 3, 4, or 5, tick-borne encephalitis virus (TBEV) and Japanese encephalitis virus (JEV), even more preferably selected from West Nile Virus (WNV), dengue virus (DENV), in particular serotype 1, 2, 3, 4, or 5 and tick-borne encephalitis virus (TBEV), most preferably the specific flavivirus is WNV.

In a further preferred embodiment, of above methods of the invention, the specific flavivirus is WNV and the mutant WNV peptide used in the method is a mutant peptide selected from:

(a) the T76A, M77G, W101R, L107R quadruple mutant of the ectodomain of the E protein of the West Nile Virus (WNV), or (b) a peptide with the sequence of amino acids 1 to 404 of SEQ ID No: 2, (c) a peptide with the sequence of SEQ ID No: 3.

In an even more preferred embodiment, the wt WNV peptide used in such methods of the invention is at least one wildtype peptide selected from the group of:
  (i) the ectodomain of the wildtype E protein of the West Nile Virus (WNV), preferably wherein the West Nile Virus is the West Nile Virus New York 1999 strain and/or has the a genome sequence according to accession number FJ151394,
  (ii) a peptide with the sequence of amino acids 1 to 404 of SEQ ID No: 1, and
  (iii) a peptide with the sequence of SEQ ID No: 4.

In yet a further preferred embodiment, the flavivirus is DENV, in particular DENV serotype 2, and the mutant DENV peptide used in the method is a mutant peptide selected from:
  (i) the T76R, Q77E, W101R, L107R quadruple mutant of the ectodomain of the E protein of DENV, in particular DENV serotype 2 and (ii) the T76A, Q77G, W101R, L107R quadruple mutant of the ectodomain of the E protein of DENV. The corresponding wt sequence of the E protein of DENV serotype 2 is shown in SEQ ID No: 13. The ectodomain preferably corresponds to amino acids 1 to 404 of the sequence.

Alternatively, (iii) the T76A, Q77E, W101R, L107R quadruple mutant of the ectodomain of the E protein of DENV, or (iv) the T76R, Q77G, W101R, L107R quadruple mutant of the ectodomain of the E protein of DENV may be used, in particular, wherein DENV is of serotype 1, 2, 3, 4 or 5, in particular of serotype 2.

In yet a further preferred embodiment, the flavivirus is TBEV, and the mutant TBEV peptide used in the method is a mutant peptide selected from:
  (i) T76A, M77G, W101R, L107R quadruple mutant of the ectodomain of the E protein of the TBEV virus, (ii) the T76R, M77E, W101R, L107R quadruple mutant of the ectodomain of the E protein of TBEV, (iii) the T76A, M77E, W101R, L107R quadruple mutant of the ectodomain of the E protein of TBEV, or (iv) the T76R, M77G, W101R, L107R quadruple mutant of the ectodomain of the E protein of TBEV may be used.

In a further embodiment, methods of the invention are performed for 2, 3, 4, 5, 6, 7, 8, 9, 10 or more of "couples" of mutant ectodomain peptides of a specific flavivirus and the corresponding wt ectodomain peptide of the specific flavivirus. Such methods may be performed in parallel, for example by using solid supports which contain 2, 3, 4, 5, 6, 7, 8, 9, 10 or more different mutant ectodomain peptides for different specific flaviviruses, and 2, 3, 4, 5, 6, 7, 8, 9, 10 or more different corresponding wt ectodomain peptides for the different specific flaviviruses. Alternatively, the methods are performed temporally and/or spatially separately.

For example, the method may be performed using a kit or solid support of the invention as follows:
  (a1) the T76A, M77G, W101R, L107R quadruple mutant of the ectodomain of the E protein of the West Nile Virus (WNV) and its corresponding wt ectodomain WNV peptide, as described above, and/or
  (b1) the T76A, Q77G, W101R, L107R quadruple mutant of the E protein of DENV serotype 1, 2, 3, 4 or 5 and its corresponding wt ectodomain DENV peptide, as described above, and/or
  (b2) the T76A, M77G, W101R, L107R quadruple mutant of the ectodomain of the E protein of the TBEV virus and its corresponding wt ectodomain TBEV peptide, and/or
  (b3) the T76R, Q77E, W101R, L107R quadruple mutant of the ectodomain of the E protein of DENV serotype 2, and its corresponding wt ectodomain DENV serotype 2 peptide.

For example (a1) and (b3), (a1) and (b1), (a1) and (b2), (b2) and (b3), or (a1), (b3) and (b2) may be used.

Therefore, in one further embodiment of the invention, the methods of the invention as described above further comprise:
  (x) repeating the steps of a method of the invention 2, 3, 4, 5, 6, 7, 8, 9, 10 or more times for a different specific flavivirus, i.e.
    repeating steps (1) to (4) of the method for discriminating infections with a specific flavivirus, or
    repeating steps (1) to (6) in case of the method for discriminating acute infections, or
    repeating steps (i) to (iii) of the method for distinguishing a West Nile Virus infection from other flavivirus infections,
    for (a) further, different specific flavivirus(es).

The repeating of the steps may be performed at the same time, i.e. in parallel, e.g. by using a suitable solid support such as an array, chip or multi-well plate, or temporally and/or spatially separated.

For example, the method may be performed for WNV as specific flavivirus, and is repeated for TBEV and/or DENV using suitable mutant peptides of the invention or biologically active variant thereof and the respective corresponding wt peptides.

In a further embodiment, the present invention relates to a method of treating a patient infected with West Nile Virus, comprising the steps:
  (x1) performing a method of the invention
    for discriminating infections with a specific flavivirus, or
    for discriminating acute infections, or
    for distinguishing a West Nile Virus infection from other flavivirus infections,
  (x2) treating the patient with an effective amount of pain reliever and/or supportive treatment, such as intravenous fluids, airway management such as a tube, ventilatory support, prevention of secondary infections, and/or nursing care,
    in case the patient is diagnosed to suffer from a West Nile Virus infection in step (x1) by discriminating the infection from other flaviviral infections.

The methods, uses and kits of the present invention are useful for testing samples from animals, in particular animals developing antibodies, more preferably mammals and birds.

According to the present invention, an animal is preferably selected from the group consisting of a mammal and a bird.

According to the present invention, the mammal is preferably selected from a human, monkey, horse, donkey, cow, pig, dog and cat, more preferably human and horse, most preferably human.

According to the present invention, the bird is preferably selected from raptors, corvids and passerines.

The samples used investigated and/or used in the methods and kits of the invention are from animals, in preferably mammals, such as human or horses, and birds, such as raptors, corvids and passerines.

In a further preferred embodiment, the sample investigated and/or used in the methods and kits of the invention is selected from serum, blood, sputum, saliva and CSF.

In a preferred embodiment, serum, blood, sputum, saliva or CSF samples from mammals, such as humans or horses may be used in methods of the invention.

In a further preferred embodiment, serum, blood, sputum, saliva or CSF samples from birds, such as raptors, corvids and passerines, may be used in methods of the invention.

The invention further relates to a composition comprising a mutant peptide of the invention or a biologically active variant thereof. In a preferred embodiment, the composition is a gel, in particular hydrogel, or liquid, more preferably a solution, suspension or emulsion comprising a mutant peptide of the invention or a biologically active variant thereof.

In a more preferred embodiment, the solution is an aqueous solution, in particular buffered aqueous solution.

In one preferred embodiment, the pH of a liquid comprising the mutant peptide of the invention or a biologically active variant thereof is between 6.0 and 8.0, more preferably 6.5 and 7.8. In another preferred embodiment, the pH of a liquid comprising the mutant peptide of the invention or a biologically active variant thereof is between 8.0 and 10.0, more preferably 9.0 and 9.8.

In a more preferred embodiment, the composition of the invention further comprises auxiliary excipients, such as protease inhibitors, buffering compounds, such as phosphate, Tris or HEPES, and stabilizers, in particular wherein the composition is an aqueous liquid, such as an aqueous solution.

In another embodiment, the composition of the invention is solid, for example, the composition is frozen, or the mutant peptide of the invention is in dry form, for example it may be dried or freeze-dried.

In a further preferred embodiment, the mutant peptide of the invention or the biologically active variant thereof or the composition of the invention, or the mutant peptide or biologically active variant thereof and/or peptide of a kit of the invention is in a container, such as a vessel, tube, capillary or syringe. For example, the mutant peptide of the invention or the composition of the invention may be in a unit dose which allows diagnostic use in a method of the present invention.

The amount of mutant peptide, and optionally the wt peptide, suitable for performing a method of the invention depends on the peptide, assay format, detected antibody isotype, solid support if present, and the read-out.

Typically, the amount of mutant peptide WNV or biologically active variant thereof as described in the Examples in a non-capture ELISA format performed in a well plate is the range of 10 ng to 500 ng, more preferably 50 to 300 ng, even more preferably 50 to 200 ng per well.

FURTHER EXAMPLES

Example S1

Use of DENV-2 Mutant Peptide of the Invention for Discriminating Flaviviral Infections Methods Nunc polysorb plates (Thermo Scientific, Germany) were coated overnight with indicated amounts of recombinant wildtype DENV-2 E ectodomain peptide or DENV-2 E-quadruple mutant (in coating buffer (15 mM $Na_2CO_3$, 35 mM $NaHCO_3$ pH 9.6)) per well with gentle agitation at 4° C. The plates were washed three times with 350 µL per well of PBS/Tween (0.05%), followed by blocking with 5% non-fat dry milk powder (200 µL per well) for 2 h at room temperature (RT). After a second wash step, human sera (dilution 1:100 in 5% non-fat dry milk powder, 100 µL per well) were incubated for 1.5 h at RT. The sera were removed by a third wash step and 100 µL of the secondary antibody (1:5.000 diluted HRP-conjugated Goat-anti-Human IgG (Fisher Scientific)) was added for 1 h at RT. After washing, 100 µl TMB-substrate (BioLegend, Germany) was added to the wells and the plate was incubated for 30 min at RT in darkness. To stop the reaction, 50 µl 1M $H_2SO_4$ was added, followed by measurement at 450 nm and 520 nm (reference wavelength) in an ELISA Reader (Infinite M200, Tecan). All antibody tests were performed in duplicates in at least two independent experiments.

The DENV-2 E-quadruple mutant peptide used in the Example is the peptide having the sequence of amino acids 1 to 404 of SEQ ID No: 13, wherein the peptide has the following mutations: T76R, Q77E, W101R, L107R.

The wildtype DENV-2 E ectodomain peptide is the peptide having the sequence of amino acids 1 to 404 of SEQ ID No: 13.

Both peptides were produced recombinantly in S2 insect cells.

Results

Both proteins (300 ng per well) were coated onto 96-well plates and were incubated with human sera from patients infected with DENV, WNV, TBEV or negative control sera. As can be seen from FIG. 8, DENV-positive sera showed almost equal binding to wt and mutant DENV E peptide, whereas binding towards the mutant E peptide was strongly diminished in the WNV- and TBEV-infected sera. Hence, the quadruple mutant DENV E-protein of the invention can be used to discriminate DENV-infections from other flaviviruses.

Example S2

WNV IgM-ELISA Test Procedure

Methods

Nunc polysorb plates (Thermo Scientific, Germany) were coated overnight with 200 ng per well of recombinant wt WNV E ectodomain peptide or WNV E-quadruple mutant peptide (in coating buffer (15 mM $Na_2CO_3$, 35 mM $NaHCO_3$ pH 9.6)) at 4° C. Plates were washed three times with 350 µL per well of PBS/Tween (0.05%), followed by blocking with 5% non-fat dry milk powder (250 µL per well) for 2 h at room temperature (RT). After a second wash step, monkey sera (1:50, diluted in 5% non-fat dry milk powder, 100 µL per well) were incubated for 1.5 h at RT. Excess serum was removed by a third wash step. 100 µL of Goat-anti-Human IgM antibody (1:200 diluted (Sigma-Aldrich, USA)) was added and incubated for 1 h at RT. Excess anti-Human IgM antibodies were removed by a fourth wash step. Then 100 µL per well of secondary antibody (1:1000 diluted HRP-conjugated Rabbit-anti-Goat polyclonal immunoglobulin (DakoCytomation, Denmark)) was added and left for 1 h at RT. After the fifth washing, 100 µL per well of TMB-substrate (BioLegend, Germany) was added and plates were incubated for 10 minutes at RT in darkness. To stop the reaction, 50 µL per well of 1M $H_2SO_4$ was added and all plates were read within 30 minutes at 450 nm and a reference wavelength of 520 nm using an ELISA Reader (Infiniti M200, Tecan). Incubations before substrate addition were performed under gentle agitation. All antibody tests were performed in duplicates in at least two independent experiments.

The WNV E-quadruple mutant used in the Example is the peptide corresponding to amino acids 1 to 404 of the T76A, M77G, W101R, L107R mutant of the WNV E protein (SEQ ID No: 3).

The wt WNV E ectodomain peptide is the peptide corresponding to amino acids 1 to 404 of the WNV wt E protein (SEQ ID No: 4).

Results

Sera from a controlled WNV-infection study with Rhesus macaques were analyzed for binding of IgM to the wt and mutant WNV E peptide, respectively. The virus used was the WNV strain Ita09 (lineage 1). As can be seen in FIG. 9, the antigens are well recognized by IgM antibodies, as the signal increases after 8-9 days post infection.

The research which led to these results was funded by the European Union.

The invention claimed is:

1. A T76X1, M77X2, W101R, L107R mutant protein of a wildtype E protein of the West Nile Virus (WNV), wherein
X1 is a naturally occurring amino acid except T and R, and
X2 is a naturally occurring amino acid except M and E,
wherein T76X1 is understood as that the threonine residue at position 76 from the N terminus of the wildtype E protein is mutated to X1, and
wherein M77X2 is understood as that the methionine residue at position 77 from the N terminus of the wildtype E protein is mutated to X2, and
wherein W101R is understood as that the tryptophan residue at position 101 from the N terminus of the wildtype E protein is mutated to arginine, and
wherein L107R is understood as that the leucine residue at position 107 from the N terminus of the wildtype E protein is mutated to arginine,
and wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus,
or a biologically active variant thereof, wherein in said biologically active variant:
1, 2, 3, 4, or 5 of the N-terminal amino acids of the protein are deleted, and/or
1, 2, 3, 4, or 5 of the C-terminal amino acids of the protein are deleted, and/or
the protein further contains one or more further moieties, and/or
the peptide contains 1 to 40 further mutations at positions within the ectodomain.

2. The T76X1, M77X2, W101R, L107R mutant protein of the E protein of the West Nile Virus (WNV) according to claim 1, wherein
X1 is a neutral or negatively charged amino acid, or
X2 is a neutral or positively charged amino acid, or
the E-protein without mutations comprises the sequence according to SEQ ID No: 1 or SEQ ID No: 4,
the mutant protein is produced recombinantly, or
the mutant protein is produced recombinantly by bacterial expression, the mutant protein is produced recombinantly by bacterial expression in *Escherichia coli*, or the mutant protein is purified after an oxidative refolding protocol, or the mutant protein exhibits a three-dimensional folding or is refolded after bacterial expression, or the mutant protein is purified or the mutant protein is not part of a virus-like particle or a virus particle.

3. A mutant peptide selected from:
(i) the ectodomain of the mutant WNV E-protein of claim 1, and
(ii) amino acids 1-404 of the mutant WNV E-protein of claim 1, and
(iii) the T76Z1, M77Z2, W101Z3, L107Z4 mutant peptide of the peptide representing the ectodomain of the E protein of a TBEV virus, and wherein the corresponding wildtype E protein of the TBEV has a threonine residue at position 76 from the N terminus, a methionine residue at position 77 from the N terminus, a tryptophan residue at position 101 from the N terminus and a leucine residue at position 107 from the N terminus, or the T76Z1, Q77Z2, W101Z3, L107Z4 mutant peptide of the peptide representing the ectodomain of the E protein of a dengue virus (DENV), and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, or the T76Z1, T77Z2, W101Z3, L107Z4 mutant peptide of the peptide representing the ectodomain of the E protein of a JEV virus, and wherein the corresponding wildtype E protein of the JEV has a threonine residue at position 76 from the N terminus, a threonine residue at position 77 from the N terminus, tryptophan residue at position 101 from the N terminus and a leucine residue at position 107 from the N terminus, or the S76Z1, T77Z2, W101Z3, L107Z4 mutant peptide of the peptide representing the ectodomain of the E protein of a YFV virus, and wherein the corresponding wildtype E protein of the YFV has a serine residue at position 76 from the N terminus, a threonine residue at position 77 from the N terminus, tryptophan residue at position 101 from the N terminus and a leucine residue at position 107 from the N terminus, or the T76Z1, T77Z2, W101Z3, L107Z4 mutant peptide of the peptide representing the ectodomain of the E protein of an usutu virus, and wherein the corresponding wildtype E protein of the usutu virus has a threonine residue at position 76 from the N terminus, a threonine residue at position 77 from the N terminus, tryptophan residue at position 101 from the N terminus and a leucine residue at position 107 from the N terminus, wherein Z1 is a naturally occurring amino acid except T for DENV, TBEV, usutu virus and JEV, and except S for YFV, and wherein Z2 is a naturally occurring amino acid except M for TBEV and except Q for DENV and except T for JEV, usutu virus and YFV, and wherein Z3 is a naturally occurring amino acid except W, and wherein Z4 is a naturally occurring amino acid except L, and (iv) a recombinant peptide representing the ectodomain of a loss-of-function mutant peptide of the E-protein of a dengue, tick-borne encephalitis (TBEV), Japanese encephalitis (JEV), usutu virus (USUV), Zika virus (ZIKV) or yellow fever (YFV) virus, wherein said loss-of-function mutant protein is a mutant E protein of a virus, which is not recognized by antibodies binding the fusion loop domain of the wildtype E protein of the virus, and wherein "not recognized" is understood as that the Kd value for binding of such antibody to the mutant E protein is at least 10-fold higher than the Kd value for binding of the antibody to the wildtype E protein of the virus, and (v) the T76R, Q77E, W101R, L107R quadruple mutant peptide of the ectodomain of the E protein of DENV, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, and (vi) a mutant peptide representing the ectodomain of an E protein of a flavivirus selected from TBEV, dengue virus (DENV), JEV, YFV and Usutu Virus, wherein positions 76, 77, 101 and 107 of the E protein are mutated, wherein the positions are determined starting from the N terminus of the wildtype E protein, wherein the corresponding wildtype E protein have a threonine or serine residue at position 76 from the N terminus, a threonine, methionine or glutamine residue at position 77 from the N terminus, a tryptophan residue at position 101 from the N terminus and a leucine residue at position 107 from the N terminus, and (vii) the T76A, M77G, W101R, L107R quadruple mutant peptide of the ectodomain of the E protein of the West Nile Virus (WNV), and wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, or a peptide with the sequence of amino acids 1 to 404 of SEQ ID No: 2, or a peptide with the sequence of SEQ ID No: 3, or a biologically active variant thereof, wherein in said biologically active variant:
1, 2, 3, 4, or 5 of the N-terminal amino acids of the protein are deleted, and/or
1, 2, 3, 4, or 5 of the C-terminal amino acids of the protein are deleted, and/or
the protein further contains one or more further moieties, and/or
the peptide contains 1 to 40 further mutations at positions within the ectodomain.

4. A kit comprising:
(a) at least one peptide representing the ectodomain of a mutated E protein of a specific flavivirus selected from:
(i) the ectodomain of the mutant WNV E-protein of claim 1 or a biologically active variant thereof, and
(ii) amino acids 1-404 of the mutant WNV E-protein of claim 1 or a biologically active variant thereof, and
(iii) the T76Z1, M77Z2, W101Z3, L107Z4 mutant peptide of the peptide representing the ectodomain of the E protein of a TBEV virus or a biologically active variant thereof, and wherein the corresponding wildtype E protein of the TBEV has a threonine residue at position 76 from the N terminus, a methionine residue at position 77 from the N terminus, a tryptophan residue at position 101 from the N terminus and a leucine residue at position 107 from the N terminus, or the T76Z1, Q77Z2, W101Z3, L107Z4 mutant peptide of the peptide representing the ectodomain of the E protein of a dengue virus (DENV) or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, or the T76Z1, T77Z2, W101Z3, L107Z4 mutant peptide of the peptide representing the ectodomain of the E protein of a JEV virus or a biologically active variant thereof, and wherein the corresponding wildtype E protein of the JEV has a threonine residue at position 76 from the N terminus, a threonine residue at position 77 from the N terminus, tryptophan residue at position 101 from the N terminus and a leucine residue at position 107 from the N terminus, or the S76Z1, T77Z2, W101Z3, L107Z4 mutant peptide of the peptide representing the ectodomain of the E protein of a YFV virus or a biologically active variant thereof, and wherein the corresponding wildtype E protein of the YFV has a serine residue at position 76 from the N terminus, a threonine residue at position 77 from the N terminus, tryptophan residue at position 101 from the N terminus and a leucine residue at position 107 from the N terminus, or the T76Z1, T77Z2, W101Z3, L107Z4 mutant peptide of the peptide representing the ectodomain of the E protein of an usutu virus or a biologically active variant thereof, and wherein the corresponding wildtype E protein of the usutu virus has a threonine residue at position 76 from the N terminus, a threonine residue at position 77 from the N terminus, tryptophan residue at position 101 from the N terminus and a leucine residue at position 107 from the N terminus, wherein Z1 is a naturally occurring amino acid except T for DENV, TBEV, usutu virus and JEV, and except S for YFV or a biologically active variant thereof, and wherein Z2 is a naturally occurring amino acid except M for TBEV and except Q for DENV and except T for JEV, usutu virus and YFV or a biologically active variant thereof, and wherein Z3 is a naturally occurring amino acid except W, and wherein Z4 is a naturally occurring amino acid except L, and (iv) a recombinant peptide representing the ectodomain of a loss-of-function mutant peptide of the E-protein of a dengue, tick-borne encephalitis (TBEV), Japanese encephalitis (JEV), usutu virus (USUV), Zika virus (ZIKV) or yellow fever (YFV) virus or a biologically active variant thereof, wherein said loss-of-function mutant protein is a mutant E protein of a virus, which is not recognized by antibodies binding the fusion loop domain of the wildtype E protein of the virus, and wherein "not recognized" is understood as that the Kd value for binding of such antibody to the mutant E protein is at least 10-fold higher than the Kd value for binding of the antibody to the wildtype E protein of the virus, and (v) the T76R, Q77E, W101R, L107R quadruple mutant protein of the ectodomain of the E protein of DENV or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, and (vi) a mutant peptide representing the ectodomain of an E protein of a flavivirus selected from TBEV, dengue virus (DENV), JEV, YFV and Usutu Virus, wherein positions 76, 77, 101 and 107 of the E protein are mutated, wherein the positions are determined starting from the N terminus of the wildtype E protein, and wherein the corresponding wildtype E protein have a threonine or serine residue at position 76 from the N terminus, a threonine, methionine or glutamine residue at position 77 from the N terminus, a tryptophan residue at position 101 from the N terminus and a leucine residue at position 107 from the N terminus, or a biologically active variant thereof, and (vii) the T76A, M77G, W101R, L107R quadruple mutant protein of the ectodomain of the E protein of the West Nile Virus (WNV), and wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, or a peptide with the sequence of amino acids 1 to 404 of SEQ ID No: 2, or a peptide with the sequence of SEQ ID No: 3, wherein in said biologically active variant:

1, 2, 3, 4, or 5 of the N-terminal amino acids of the protein are deleted, and/or 1, 2, 3, 4, or 5 of the C-terminal amino acids of the protein are deleted, and/or the protein further contains one or more further moieties, and/or the peptide contains 1 to 40 further mutations at positions within the ectodomain and (b) at least one peptide representing the ectodomain of the wildtype E protein of the same flavivirus.

5. The kit according to claim 4, wherein the at least one peptide is bound to one or more solid support(s).

6. A method for discriminating infections with a specific flavivirus from infections with other flavivirus(es) comprising the steps:

(1) contacting at least one mutant peptide representing the ectodomain of a mutant E protein of a specific flavivirus selected from:

(i) the ectodomain of the mutant WNV E-protein of claim 1 or a biologically active variant thereof, and (ii) amino acids 1-404 of the mutant WNV E-protein of claim 1 or a biologically active variant thereof, and (iii) the T76Z1, M77Z2, W101Z3, L107Z4 mutant peptide of the peptide representing the ectodomain of the E protein of a TBEV virus or a biologically active variant thereof, and wherein the corresponding wildtype E protein of the TBEV has a threonine residue at position 76 from the N terminus, a methionine residue at position 77 from the N terminus, a tryptophan residue at position 101 from the N terminus and a leucine residue at position 107 from the N terminus, or the T76Z1, Q77Z2, W101Z3, L107Z4 mutant peptide of the peptide representing the ectodomain of the E protein of a dengue virus (DENV) or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, or the T76Z1, T77Z2, W101Z3, L107Z4 mutant peptide of the peptide representing the ectodomain of the E protein of a JEV virus or a biologically active variant thereof, and wherein the corresponding wildtype E protein of the JEV has a threonine residue at position 76 from the N terminus, a threonine residue at position 77 from the N terminus, tryptophan residue at position 101 from the N terminus and a leucine residue at position 107 from the N terminus, or the S76Z1, T77Z2, W101Z3, L107Z4 mutant peptide of the peptide representing the ectodomain of the E protein of a YFV virus or a biologically active variant thereof, and wherein the corresponding wildtype E protein of the YFV has a serine residue at position 76 from the N terminus, a threonine residue at position 77 from the N terminus, tryptophan residue at position 101 from the N terminus and a leucine residue at position 107 from the N terminus, or the T76Z1, T77Z2, W101Z3, L107Z4 mutant peptide of the peptide representing the ectodomain of the E protein of an usutu virus or a biologically active variant thereof, and wherein the corresponding wildtype E protein of the usutu virus has a threonine residue at position 76 from the N terminus, a threonine residue at position 77 from the N terminus, tryptophan residue at position 101 from the N terminus and a leucine residue at position 107 from the N terminus, wherein Z1 is a naturally occurring amino acid except T for DENV, TBEV, usutu virus and JEV, and except S for YFV or a biologically active variant thereof, and wherein Z2 is a naturally occurring amino acid except M for TBEV and except Q for DENV and except T for JEV, usutu virus and YFV or a biologically active variant thereof, and wherein Z3 is a naturally occurring amino acid except W, and wherein Z4 is a naturally occurring amino acid except L, and (iv) a recombinant peptide representing the ectodomain of a loss-of-function mutant peptide of the E-protein of a dengue, tick-borne encephalitis (TBEV), Japanese encephalitis (JEV), usutu virus (USUV), Zika virus (ZIKV) or yellow fever (YFV) virus or a biologically active variant thereof, wherein said loss-of-function mutant protein is a mutant E protein of a virus, which is not recognized by antibodies binding the fusion loop domain of the wildtype E protein of the virus, and wherein "not recognized" is understood as that the Kd value for binding of such antibody to the mutant E protein is at least 10-fold higher than the Kd value for binding of the antibody to the wildtype E protein of the virus, and (v) the T76R, Q77E, W101R, L107R quadruple mutant peptide of the ectodomain of the E protein of DENV or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, and (vi) a mutant peptide representing the ectodomain of an E protein of a flavivirus selected from TBEV, dengue virus (DENV), JEV, YFV and Usutu Virus, wherein positions 76, 77, 101 and 107 of the E protein are mutated, wherein the positions are determined starting from the N terminus of the wildtype E protein, wherein the corresponding wildtype E protein have a threonine or serine residue at position 76 from the N terminus, a threonine, methionine or glutamine residue at position 77 from the N terminus, a tryptophan residue at position 101 from the N terminus and a leucine residue at position 107 from the N terminus, or a biologically active variant thereof, and (vii) the T76A, M77G, W101R, L107R quadruple mutant peptide of the ectodomain of the E protein of the West Nile Virus (WNV), and wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, or a peptide with the sequence of amino acids 1 to 404 of SEQ ID No: 2, or a peptide with the sequence of SEQ ID No: 3, wherein in said biologically active variant:

1, 2, 3, 4, or 5 of the N-terminal amino acids of the protein are deleted, and/or 1, 2, 3, 4, or 5 of the C-terminal amino acids of the protein are deleted, and/or the protein further contains one or more further moieties, and/or the peptide contains 1 to 40 further mutations at positions within the ectodomain, with an animal sample containing or suspected to contain antibodies binding to the specific flavivirus, (2) contacting at least one wildtype peptide representing the ectodomain of the wildtype E protein of the specific flavivirus of step (1) with an animal sample, (3) determining the amount of mutant peptide-antibody complex formed in step (1), and the amount of wildtype peptide-antibody complex formed in step (2), (4) determining the ratio (a)/(b) between the amounts measured in step (3) for (a) the wildtype peptide of step (2), and (b) the mutant peptide of step (1), wherein a ratio (a)/(b) of above 2 indicates that the animal is not infected with the specific flavivirus, or wherein a ratio (a)/(b) of 2 or lower indicates that the animal is infected with the specific flavivirus.

7. The method according to claim 6, wherein determining the amount of mutant peptide-antibody complex formed in step (1), and the amount of wildtype peptide-antibody complex formed in step (2) is performed (a) by an ELISA assay, or (b) by a capture assay.

8. A method for discriminating acute infections with a specific flavivirus from acute infections with other flavivirus(es) comprising the steps:
(1) providing at least one solid support to which anti-mammalian IgM antibodies are bound,
(2) contacting the solid support with a mammalian sample containing or suspected to contain antibodies binding to a specific flavivirus,
(3) contacting at least one peptide representing the ectodomain of a mutated E protein of a specific flavivirus with at least one solid support of step (2), whereby mutant peptide-antibody complexes are allowed to form, and
wherein the at least one peptide is selected from:
  (i) the ectodomain of the mutant WNV E-protein of claim 1 or a biologically active variant thereof, and
  (ii) amino acids 1-404 of the mutant WNV E-protein of claim 1 or a biologically active variant thereof, and
  (iii) the T76Z1, M77Z2, W101Z3, L107Z4 mutant peptide of the peptide representing the ectodomain of the E protein of a TBEV virus or a biologically active variant thereof, and wherein the corresponding wildtype E protein of the TBEV has a threonine residue at position 76 from the N terminus, a methionine residue at position 77 from the N terminus, a tryptophan residue at position 101 from the N terminus and a leucine residue at position 107 from the N terminus, or
  the T76Z1, Q77Z2, W101Z3, L107Z4 mutant peptide of the peptide representing the ectodomain of the E protein of a dengue virus (DENV) or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, or
  the T76Z1, T77Z2, W101Z3, L107Z4 mutant peptide of the peptide representing the ectodomain of the E protein of a JEV virus or a biologically active variant thereof, and wherein the corresponding wildtype E protein of the JEV has a threonine residue at position 76 from the N terminus, a threonine residue at position 77 from the N terminus, tryptophan residue at position 101 from the N terminus and a leucine residue at position 107 from the N terminus, or
  the S76Z1, T77Z2, W101Z3, L107Z4 mutant peptide of the peptide representing the ectodomain of the E protein of a YFV virus or a biologically active variant thereof, and wherein the corresponding wildtype E protein of the YFV has a serine residue at position 76 from the N terminus, a threonine residue at position 77 from the N terminus, tryptophan residue at position 101 from the N terminus and a leucine residue at position 107 from the N terminus, or
  the T76Z1, T77Z2, W101Z3, L107Z4 mutant peptide of the peptide representing the ectodomain of the E protein of an usutu virus or a biologically active variant thereof, and wherein the corresponding wildtype E protein of the usutu virus has a threonine residue at position 76 from the N terminus, a threonine residue at position 77 from the N terminus, tryptophan residue at position 101 from the N terminus and a leucine residue at position 107 from the N terminus,
  wherein Z1 is a naturally occurring amino acid except T for DENV, TBEV, usutu virus and JEV, and except S for YFV or a biologically active variant thereof, and
  wherein Z2 is a naturally occurring amino acid except M for TBEV and except Q for DENV and except T for JEV, usutu virus and YFV or a biologically active variant thereof, and
  wherein Z3 is a naturally occurring amino acid except W, and
  wherein Z4 is a naturally occurring amino acid except L, and
  (iv) a recombinant peptide representing the ectodomain of a loss-of-function mutant peptide of the E-protein of a dengue, tick-borne encephalitis (TBEV), Japanese encephalitis (JEV), usutu virus (USUV), Zika virus (ZIKV) or yellow fever (YFV) virus or a biologically active variant thereof, wherein said loss-of-function mutant protein is a mutant E protein of a virus, which is not recognized by antibodies binding the fusion loop domain of the wildtype E protein of the virus, and wherein "not recognized" is understood as that the Kd value for binding of such antibody to the mutant E protein is at least 10-fold higher than the Kd value for binding of the antibody to the wildtype E protein of the virus, and
  (v) the T76R, Q77E, W101R, L107R quadruple mutant peptide of the ectodomain of the E protein of DENV or a biologically active variant thereof, and
  (vi) a mutant peptide representing the ectodomain of an E protein of a flavivirus selected from TBEV, dengue virus (DENV), JEV, YFV and Usutu Virus, wherein positions 76, 77, 101 and 107 of the E protein are mutated, wherein the positions are determined starting from the N terminus of the wildtype E protein, and wherein the corresponding wildtype E protein have a threonine or serine residue at position 76 from the N terminus, a threonine, methionine or glutamine residue at position 77 from the N terminus, a tryptophan residue at position 101 from the N terminus and a leucine residue at position 107 from the N terminus, or a biologically active variant thereof, and
  (viii) the T76A, M77G, W101R, L107R quadruple mutant peptide of the ectodomain of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, or a peptide with the sequence of amino acids 1 to 404 of SEQ ID No: 2, or a peptide with the sequence of SEQ ID No: 3,
wherein in said biologically active variant:
  1, 2, 3, 4, or 5 of the N-terminal amino acids of the protein are deleted, and/or
  1, 2, 3, 4, or 5 of the C-terminal amino acids of the protein are deleted, and/or
  the protein further contains one or more further moieties, and/or
  the peptide contains 1 to 40 further mutations at positions within the ectodomain
(4) contacting at least one peptide representing the ectodomain of the wildtype E protein of the specific flavivirus with at least one solid support of step (2), whereby wildtype peptide-antibody complexes are allowed to form, with the proviso that the contacting of steps (3) and (4) takes place on non-overlapping areas of a solid support, (5) determining the amounts of mutant peptide-antibody complexes and wildtype peptide-antibody complexes by using an optionally labelled secondary antibody, (6) determining the ratio (a)/(b) between the amounts determined in step (5) for (a) the wildtype peptide of step (4) and (b) the mutant peptide of step (3), wherein a ratio (a)/(b) of above 2 indicates that the mammal is not acutely infected with the specific flavivirus, or wherein a ratio (a)/(b) of 2 or lower indicates that the mammal is acutely infected with the specific flavivirus.

9. A nucleic acid encoding a mutant peptide selected of:
(i) the ectodomain of the mutant WNV E-protein of claim 1 or a biologically active variant thereof, and
(ii) amino acids 1-404 of the mutant WNV E-protein of claim 1 or a biologically active variant thereof, and
(iii) the T76Z1, M77Z2, W101Z3, L107Z4 mutant peptide of the peptide representing the ectodomain of the E protein of a TBEV virus or a biologically active variant thereof, and wherein the corresponding wildtype E protein of the TBEV has a threonine residue at position 76 from the N terminus, a methionine residue at position 77 from the N terminus, a tryptophan residue at position 101 from the N terminus and a leucine residue at position 107 from the N terminus, or the T76Z1, Q77Z2, W101Z3, L107Z4 mutant peptide of the peptide representing the ectodomain of the E protein of a dengue virus (DENV) or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, or the T76Z1, T77Z2, W101Z3, L107Z4 mutant peptide of the peptide representing the ectodomain of the E protein of a JEV virus or a biologically active variant thereof, and wherein the corresponding wildtype E protein of the JEV has a threonine residue at position 76 from the N terminus, a threonine residue at position 77 from the N terminus, tryptophan residue at position 101 from the N terminus and a leucine residue at position 107 from the N terminus, or the S76Z1, T77Z2, W101Z3, L107Z4 mutant peptide of the peptide representing the ectodomain of the E protein of a YFV virus or a biologically active variant thereof, and wherein the corresponding wildtype E protein of the YFV has a serine residue at position 76 from the N terminus, a threonine residue at position 77 from the N terminus, tryptophan residue at position 101 from the N terminus and a leucine residue at position 107 from the N terminus, or the T76Z1, T77Z2, W101Z3, L107Z4 mutant peptide of the peptide representing the ectodomain of the E protein of an usutu virus or a biologically active variant thereof, and wherein the corresponding wildtype E protein of the usutu virus has a threonine residue at position 76 from the N terminus, a threonine residue at position 77 from the N terminus, tryptophan residue at position 101 from the N terminus and a leucine residue at position 107 from the N terminus, wherein Z1 is a naturally occurring amino acid except T for DENV, TBEV, usutu virus and JEV, and except S for YFV or a biologically active variant thereof, and wherein Z2 is a naturally occurring amino acid except M for TBEV and except Q for DENV and except T for JEV, usutu virus and YFV or a biologically active variant thereof, and wherein Z3 is a naturally occurring amino acid except W, and wherein Z4 is a naturally occurring amino acid except L, (iv) a recombinant peptide representing the ectodomain of a loss-of-function mutant peptide of the E-protein of a dengue, tick-borne encephalitis (TBEV), Japanese encephalitis (JEV), usutu virus (USUV), Zika virus (ZIKV) or yellow fever (YFV) virus or a biologically active variant thereof, wherein said loss-of-function mutant protein is a mutant E protein of a flavivirus, which is not recognized by antibodies binding the fusion loop domain of the wildtype E protein of the virus, and wherein "not recognized" is understood as that the Kd value for binding of such antibody to the mutant E protein is at least 10-fold higher than the Kd value for binding of the antibody to the wildtype E protein of the virus, and (v) the T76R, Q77E, W101R, L107R quadruple mutant peptide of the ectodomain of the E protein of DENV or a biologically active variant thereof, and wherein the corresponding wildtype E protein of the DENV has a threonine residue at position 76 from the N terminus, a glutamine residue at position 77 from the N terminus, a tryptophan residue at position 101 from the N terminus and a leucine residue at position 107 from the N terminus, and (vi) a mutant peptide representing the ectodomain of an E protein of a flavivirus selected from TBEV, dengue virus (DENV), JEV, YFV and Usutu Virus, wherein positions 76, 77, 101 and 107 of the E protein are mutated, or a biologically active variant thereof, wherein the positions are determined starting from the N terminus of the wildtype E protein, wherein the corresponding wildtype E protein have a threonine or serine residue at position 76 from the N terminus, a threonine, methionine or glutamine residue at position 77 from the N terminus, a tryptophan residue at position 101 from the N terminus and a leucine residue at position 107 from the N terminus, and (viii) the T76A, M77G, W101R, L107R quadruple mutant peptide of the ectodomain of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, or a peptide with the sequence of amino acids 1 to 404 of SEQ ID No: 2, or a peptide with the sequence of SEQ ID No: 3, and (ix) a T76X1, M77X2, W101R, L107R mutant peptide of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, wherein
X1 is a naturally occurring amino acid except T and R, and
X2 is a naturally occurring amino acid except M and E, or a biologically active variant thereof.

10. The T76X1, M77X2, W101R, L107R mutant protein of the E protein of the West Nile Virus (WNV) according to claim 1 selected from:
   (a) the T76A, M77G, W101R, L107R quadruple mutant protein of the E protein of the West Nile Virus (WNV), and
   (b) a peptide with the sequence of SEQ ID No: 2.

11. The mutant peptide according to claim 3 selected from:
   (a) the T76A, M77G, W101R, L107R quadruple mutant peptide of the ectodomain of the E protein of the West Nile Virus (WNV), or
   (b) a peptide with the sequence of amino acids 1 to 404 of SEQ ID No: 2,
   (c) a peptide with the sequence of SEQ ID No: 3.

12. The mutant peptide according to claim 11, wherein
   (i) the West Nile Virus
      is the West Nile Virus New York 1999 strain, or
      has a genome sequence according to accession number FJ151394,
      and wherein the E-protein without mutations comprises the sequence according to SEQ ID No: 1 or SEQ ID No: 4,
   or
   (ii) the peptide is produced recombinantly, or
   (iii) the peptide is purified after an oxidative refolding protocol, or
   (iv) the peptide exhibits a three-dimensional folding or is refolded after bacterial expression, or
   (v) wherein the peptide is purified or is not part of a virus-like particle or a virus particle.

13. The kit according to claim 4 comprising:
   (a) at least one mutant peptide selected from:
      (i) the T76A, M77G, W101R, L107R quadruple mutant peptide of the ectodomain of the E protein of the West Nile Virus (WNV), and
      (ii) a peptide with the sequence of amino acids 1 to 404 of SEQ ID No: 2, and
      (ii) a peptide with the sequence of SEQ ID No: 3, and
   (b) at least one wildtype peptide selected from the group of:
      (i) the ectodomain of the wildtype E protein of the West Nile Virus (WNV),
      (ii) a peptide with the sequence of amino acids 1 to 404 of SEQ ID No: 1, and
      (iii) a peptide with the sequence of SEQ ID No: 4.

14. The kit according to claim 13, further comprising:
   (i) reference human serum samples from confirmed WNV infections,
   (ii) reference human serum samples from
      JEV vaccinated individuals, or
      confirmed TBEV-infected individuals, or
      DENV-infected individuals, or
      negative control individuals, or
   (iii) an HRP-conjugated goat anti-human IgG antibody or TMB.

15. A solid support, coated with at least one mutant peptide selected from:
   (a) the T76A, M77G, W101R, L107R quadruple mutant peptide of the ectodomain of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, and
   (b) a peptide with the sequence of amino acids 1 to 404 of SEQ ID No: 2, and
   (c) a peptide with the sequence of SEQ ID No: 3,
   and wherein said solid support is optionally further coated with at least one wildtype peptide selected from the group of:
   (i) the ectodomain of the wildtype E protein of the West Nile Virus (WNV), wherein the wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, and
   (ii) a peptide with the sequence of amino acids 1 to 404 of SEQ ID No: 1, and
   (iii) a peptide with the sequence of SEQ ID No: 4.

16. A method for distinguishing a West Nile Virus infection from other flavivirus infections, comprising the following steps:
   (i) contacting at least one solid support coated with at least one mutant peptide selected from:
      (a) the T76A, M77G, W101R, L107R quadruple mutant peptide of the ectodomain of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, and
      (b) a peptide with the sequence of amino acids 1 to 404 of SEQ ID No: 2, and
      (c) a peptide with the sequence of SEQ ID No: 3, and
      wherein said solid support is further coated with at least one wildtype peptide selected from the group of:
      (i) the ectodomain of the wildtype E protein of the West Nile Virus (WNV), wherein the wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus,
      (ii) a peptide with the sequence of amino acids 1 to 404 of SEQ ID No: 1, and
      (iii) a peptide with the sequence of SEQ ID No: 4,
      with a human sample containing or suspected to contain antibodies binding to a flavivirus,
   (ii) determining the amount of bound antibodies,
   (iii) determining the ratio (a)/(b) between the amounts determined for (a) the at least one wildtype peptide and (b) the at least one mutant peptide,
   wherein a ratio of above 2 indicates that the human is not infected with West Nile Virus, and is infected with an other flavivirus, or is vaccinated against an other flavivirus, or
   wherein a ratio of 2 or lower indicates that the human is infected with West Nile Virus.

17. The method according to claim 16, wherein
(a) the amount of bound antibodies in step (ii) is measured by contacting an HRP-conjugated goat anti-human IgG antibody with the solid support after step (i), or
(b) equal loading of at least one mutant peptide and at least one wildtype peptide on each well of the coated solid support is verified, or
(c) 50 ng to 300 ng of peptide is coated to each well of the solid support.

18. A method for distinguishing a West Nile Virus infection from other flavivirus infections, comprising the following steps:
(1) contacting at least one mutant peptide selected from:
(a) the T76A, M77G, W101R, L107R quadruple mutant peptide of the ectodomain of the E protein of the West Nile Virus (WNV), wherein the corresponding wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, and
(b) a peptide with the sequence of amino acids 1 to 404 of SEQ ID No: 2, and
(c) a peptide with the sequence of SEQ ID No: 3, with a human sample containing or suspected to contain antibodies binding to a flavivirus,
(2) contacting at least one wildtype peptide selected from the group of:
(i) the ectodomain of the wildtype E protein of the West Nile Virus (WNV), wherein the wildtype E protein the West Nile Virus (WNV) has a threonine residue at position 76 from the N terminus, a methionine residue at position 77 from the N terminus, a tryptophan residue at position 101 from the N terminus and a leucine residue at position 107 from the N terminus, and
(ii) a peptide with the sequence of amino acids 1 to 404 of SEQ ID No: 1, and
(iii) a peptide with the sequence of SEQ ID No: 4, with a human sample,
(3) determining the amount of bound antibodies in steps (1) and (2),
(4) determining the ratio (a)/(b) between the amounts determined for (a) the at least one wildtype peptide and (b) the at least one mutant peptide,
wherein a ratio of above 2 indicates that the human is not infected with West Nile Virus, and is infected with an other flavivirus, or is vaccinated against an other flavivirus, or wherein a ratio of 2 or lower indicates that the human is infected with West Nile Virus or is vaccinated against West Nile Virus.

19. The method according to claim 16 or 18, wherein said human sample is human serum or human cerebrospinal fluid, or wherein said West Nile Virus infection is distinguished from other clinically relevant flaviviral infections or from dengue virus (DENV), tick-borne encephalitis virus (TBEV), Japanese encephalitis virus (JEV), usutu virus (USUV) or yellow fever virus (YFV) infections.

20. The nucleic acid according to claim 9, comprised in a vector, plasmid or host cell.

* * * * *

```
                        SEQUENCE LISTING

<160> NUMBER OF SEQ ID NOS: 25

<210> SEQ ID NO 1
<211> LENGTH: 415
<212> TYPE: PRT
<213> ORGANISM: West Nile virus

<400> SEQUENCE: 1

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Val Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
```

```
            325                 330                 335
Lys Val Pro Ile Ser Ser Val Ala Ser Leu Asn Asp Leu Thr Pro Val
            340                 345                 350
Gly Arg Leu Val Thr Val Asn Pro Phe Val Ser Val Ala Thr Ala Asn
            355                 360                 365
Ala Lys Val Leu Ile Glu Leu Glu Pro Pro Phe Gly Asp Ser Tyr Ile
            370                 375                 380
Val Val Gly Arg Gly Glu Gln Gln Ile Asn His His Trp His Lys Ser
385                 390                 395                 400
Gly Ser Ser Ile Gly Lys Ala Phe Thr Thr Thr Leu Lys Gly Ala
            405                 410                 415

<210> SEQ ID NO 2
<211> LENGTH: 415
<212> TYPE: PRT
<213> ORGANISM: Artificial Sequence
<220> FEATURE:
<223> OTHER INFORMATION: T76A, M77G, W101R, L107R mutant of amino acids
      1-415 of WNV E protein

<400> SEQUENCE: 2

Phe Asn Cys Leu Gly Met Ser Asn Arg Asp Phe Leu Glu Gly Val Ser
1               5                   10                  15
Gly Ala Thr Trp Val Asp Leu Val Leu Glu Gly Asp Ser Cys Val Thr
            20                  25                  30
Ile Met Ser Lys Asp Lys Pro Thr Ile Asp Val Lys Met Met Asn Met
            35                  40                  45
Glu Ala Val Asn Leu Ala Glu Val Arg Ser Tyr Cys Tyr Leu Ala Thr
50                  55                  60
Val Ser Asp Leu Ser Thr Lys Ala Ala Cys Pro Ala Gly Gly Glu Ala
65                  70                  75                  80
His Asn Asp Lys Arg Ala Asp Pro Ala Phe Val Cys Arg Gln Gly Val
            85                  90                  95
Val Asp Arg Gly Arg Gly Asn Gly Cys Gly Arg Phe Gly Lys Gly Ser
            100                 105                 110
Ile Asp Thr Cys Ala Lys Phe Ala Cys Ser Thr Lys Ala Ile Gly Arg
            115                 120                 125
Thr Ile Leu Lys Glu Asn Ile Lys Tyr Glu Val Ala Ile Phe Val His
            130                 135                 140
Gly Pro Thr Thr Val Glu Ser His Gly Asn Tyr Ser Thr Gln Val Gly
145                 150                 155                 160
Ala Thr Gln Ala Gly Arg Phe Ser Ile Thr Pro Ala Ala Pro Ser Tyr
            165                 170                 175
Thr Leu Lys Leu Gly Glu Tyr Gly Glu Val Thr Val Asp Cys Glu Pro
            180                 185                 190
Arg Ser Gly Ile Asp Thr Asn Ala Tyr Tyr Val Met Thr Val Gly Thr
            195                 200                 205
Lys Thr Phe Leu Val His Arg Glu Trp Phe Met Asp Leu Asn Leu Pro
            210                 215                 220
Trp Ser Ser Ala Gly Ser Thr Val Trp Arg Asn Arg Glu Thr Leu Met
225                 230                 235                 240
Glu Phe Glu Glu Pro His Ala Thr Lys Gln Ser Val Ile Ala Leu Gly
            245                 250                 255
Ser Gln Glu Gly Ala Leu His Gln Ala Leu Ala Gly Ala Ile Pro Val
            260                 265                 270
```

```
Glu Phe Ser Ser Asn Thr Val Lys Leu Thr Ser Gly His Leu Lys Cys
            275                 280                 285

Arg Val Lys Met Glu Lys Leu Gln Leu Lys Gly Thr Thr Tyr Gly Val
290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
355                 360                 365

Ala Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala
                405                 410                 415

<210> SEQ ID NO 3
<211> LENGTH: 404
<212> TYPE: PRT
<213> ORGANISM: Artificial Sequence
<220> FEATURE:
<223> OTHER INFORMATION: ectodomain of T76A, M77G, W101R, L107R mutant
      of the WNV E protein

<400> SEQUENCE: 3

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
                20                  25                  30

Ile Met Ser Lys Asp Lys Pro Thr Ile Asp Val Lys Met Met Asn Met
            35                  40                  45

Glu Ala Val Asn Leu Ala Glu Val Arg Ser Tyr Cys Tyr Leu Ala Thr
50                  55                  60

Val Ser Asp Leu Ser Thr Lys Ala Ala Cys Pro Ala Gly Gly Glu Ala
65                  70                  75                  80

His Asn Asp Lys Arg Ala Asp Pro Ala Phe Val Cys Arg Gln Gly Val
                85                  90                  95

Val Asp Arg Gly Arg Gly Asn Gly Cys Gly Arg Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
210                 215                 220
```

-continued

```
Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
            245                 250                 255

Ser Gln Glu Gly Ala Leu His Gln Ala Leu Ala Gly Ala Ile Pro Val
        260                 265                 270

Glu Phe Ser Ser Asn Thr Val Lys Leu Thr Ser Gly His Leu Lys Cys
    275                 280                 285

Arg Val Lys Met Glu Lys Leu Gln Leu Lys Gly Thr Thr Tyr Gly Val
290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile

<210> SEQ ID NO 4
<211> LENGTH: 404
<212> TYPE: PRT
<213> ORGANISM: West Nile virus

<400> SEQUENCE: 4

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Val Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190
```

```
Arg Ser Gly Ile Asp Thr Asn Ala Tyr Tyr Val Met Thr Val Gly Thr
            195                 200                 205

Lys Thr Phe Leu Val His Arg Glu Trp Phe Met Asp Leu Asn Leu Pro
210                 215                 220

Trp Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
            245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
            275                 280                 285

Arg Val Lys Met Glu Lys Leu Gln Leu Lys Gly Thr Thr Tyr Gly Val
            290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
            325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
            355                 360                 365

Ala Lys Val Leu Ile Glu Leu Glu Pro Pro Phe Gly Asp Ser Tyr Ile
            370                 375                 380

Val Val Gly Arg Gly Glu Gln Gln Ile Asn His His Trp His Lys Ser
385                 390                 395                 400

Gly Ser Ser Ile

<210> SEQ ID NO 5
<211> LENGTH: 58
<212> TYPE: PRT
<213> ORGANISM: Tick-borne encephalitis virus
<220> FEATURE:
<221> NAME/KEY: MISC_FEATURE
<222> LOCATION: (1)..(58)
<223> OTHER INFORMATION: Fusion loop domain of the wt E protein from
      TBEV Virus

<400> SEQUENCE: 5

Ala Lys Leu Ser Asp Thr Lys Val Ala Ala Arg Cys Pro Thr Met Gly
1               5                   10                  15

Pro Ala Thr Leu Ala Lys Glu His Gln Gly Gly Thr Val Cys Lys Arg
            20                  25                  30

Asp Gln Ser Asp Arg Gly Trp Gly Asn His Cys Gly Leu Phe Gly Lys
        35                  40                  45

Gly Ser Ile Val Ala Cys Val Lys Ala Ala
    50                  55

<210> SEQ ID NO 6
<211> LENGTH: 58
<212> TYPE: PRT
<213> ORGANISM: Dengue virus type 1
<220> FEATURE:
<221> NAME/KEY: MISC_FEATURE
<222> LOCATION: (1)..(58)
<223> OTHER INFORMATION: Fusion loop domain of the wt E protein from
      Dengue Virus, serotype 1

<400> SEQUENCE: 6
```

```
Ala Lys Ile Ser Asn Thr Thr Thr Asp Ser Arg Cys Pro Thr Gln Gly
1               5                   10                  15

Glu Ala Thr Leu Val Glu Glu Gln Asp Ala Asn Phe Val Cys Arg Arg
                20                  25                  30

Thr Phe Val Asp Arg Gly Trp Gly Asn Gly Cys Gly Leu Phe Gly Lys
            35                  40                  45

Gly Ser Leu Leu Thr Cys Ala Lys Phe Lys
        50                  55

<210> SEQ ID NO 7
<211> LENGTH: 58
<212> TYPE: PRT
<213> ORGANISM: Dengue virus type 2
<220> FEATURE:
<221> NAME/KEY: MISC_FEATURE
<222> LOCATION: (1)..(58)
<223> OTHER INFORMATION: Fusion loop domain of the wt E protein from
      Dengue Virus, serotype 2

<400> SEQUENCE: 7

Ala Lys Leu Thr Asn Thr Thr Thr Glu Ser Arg Cys Pro Thr Gln Gly
1               5                   10                  15

Glu Pro Ser Leu Val Glu Glu Gln Asp Lys Arg Phe Val Cys Arg His
                20                  25                  30

Ser Met Val Asp Arg Gly Trp Gly Asn Gly Cys Gly Leu Phe Gly Lys
            35                  40                  45

Gly Gly Ile Val Thr Cys Ala Met Phe Thr
        50                  55

<210> SEQ ID NO 8
<211> LENGTH: 58
<212> TYPE: PRT
<213> ORGANISM: Dengue virus type 3
<220> FEATURE:
<221> NAME/KEY: MISC_FEATURE
<222> LOCATION: (1)..(58)
<223> OTHER INFORMATION: Fusion loop domain of the wt E protein from
      Dengue Virus, serotype 3

<400> SEQUENCE: 8

Gly Lys Ile Thr Asn Ile Thr Thr Asp Ser Arg Cys Pro Thr Gln Gly
1               5                   10                  15

Glu Ala Val Leu Pro Glu Glu Gln Asp Gln Asn Tyr Val Cys Lys His
                20                  25                  30

Thr Tyr Val Asp Arg Gly Trp Gly Asn Gly Cys Gly Leu Phe Gly Lys
            35                  40                  45

Gly Ser Leu Val Thr Cys Ala Lys Phe Gln
        50                  55

<210> SEQ ID NO 9
<211> LENGTH: 58
<212> TYPE: PRT
<213> ORGANISM: Dengue virus type 4
<220> FEATURE:
<221> NAME/KEY: MISC_FEATURE
<222> LOCATION: (1)..(58)
<223> OTHER INFORMATION: Fusion loop domain of the wt E protein from
      Dengue Virus, serotype 4

<400> SEQUENCE: 9

Ala Ser Ile Ser Asn Ile Thr Thr Ala Thr Arg Cys Pro Thr Gln Gly
1               5                   10                  15
```

```
Glu Pro Tyr Leu Lys Glu Glu Gln Asp Gln Gln Tyr Ile Cys Arg Arg
            20                  25                  30

Asp Val Val Asp Arg Gly Trp Gly Asn Gly Cys Gly Leu Phe Gly Lys
        35                  40                  45

Gly Gly Val Val Thr Cys Ala Lys Phe Ala
    50                  55

<210> SEQ ID NO 10
<211> LENGTH: 58
<212> TYPE: PRT
<213> ORGANISM: West Nile virus
<220> FEATURE:
<221> NAME/KEY: MISC_FEATURE
<222> LOCATION: (1)..(58)
<223> OTHER INFORMATION: Fusion loop domain of the wt E protein from
      West Nile Virus

<400> SEQUENCE: 10

Ala Thr Val Ser Asp Leu Ser Thr Lys Ala Ala Cys Pro Thr Met Gly
1               5                   10                  15

Glu Ala His Asn Asp Lys Arg Ala Asp Pro Ala Phe Val Cys Arg Gln
            20                  25                  30

Gly Val Val Asp Arg Gly Trp Gly Asn Gly Cys Gly Leu Phe Gly Lys
        35                  40                  45

Gly Ser Ile Asp Thr Cys Ala Lys Phe Ala
    50                  55

<210> SEQ ID NO 11
<211> LENGTH: 58
<212> TYPE: PRT
<213> ORGANISM: Artificial Sequence
<220> FEATURE:
<223> OTHER INFORMATION: Fusion loop domain of the T76A, M77G, W101R,
      L107R mutant of the E protein from West Nile Virus

<400> SEQUENCE: 11

Ala Thr Val Ser Asp Leu Ser Thr Lys Ala Ala Cys Pro Ala Gly Gly
1               5                   10                  15

Glu Ala His Asn Asp Lys Arg Ala Asp Pro Ala Phe Val Cys Arg Gln
            20                  25                  30

Gly Val Val Asp Arg Gly Arg Gly Asn Gly Cys Gly Arg Phe Gly Lys
        35                  40                  45

Gly Ser Ile Asp Thr Cys Ala Lys Phe Ala
    50                  55

<210> SEQ ID NO 12
<211> LENGTH: 495
<212> TYPE: PRT
<213> ORGANISM: Dengue virus type 1

<400> SEQUENCE: 12

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80
```

```
Thr Leu Val Glu Glu Gln Asp Ala Asn Phe Val Cys Arg Arg Thr Phe
                85                  90                  95
Val Asp Arg Gly Trp Gly Asn Gly Cys Gly Leu Phe Gly Lys Gly Ser
            100                 105                 110
Leu Ile Thr Cys Ala Lys Phe Lys Cys Val Thr Lys Leu Glu Gly Lys
        115                 120                 125
Ile Val Gln Tyr Glu Asn Leu Lys Tyr Ser Val Ile Val Thr Val His
    130                 135                 140
Thr Gly Asp Gln His Gln Val Gly Asn Glu Ser Thr Glu His Gly Thr
145                 150                 155                 160
Thr Ala Thr Ile Thr Pro Gln Ala Pro Thr Thr Glu Ile Gln Leu Thr
                165                 170                 175
Asp Tyr Gly Ala Leu Thr Leu Asp Cys Ser Pro Arg Thr Gly Leu Asp
            180                 185                 190
Phe Asn Glu Met Val Leu Leu Thr Met Lys Glu Lys Ser Trp Leu Val
        195                 200                 205
His Lys Gln Trp Phe Leu Asp Leu Pro Leu Pro Trp Thr Ser Gly Ala
    210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
                245                 250                 255
Glu Gly Ala Met His Thr Ala Leu Thr Gly Ala Thr Glu Ile Gln Thr
            260                 265                 270
Ser Gly Thr Thr Thr Ile Phe Ala Gly His Leu Lys Cys Arg Leu Lys
        275                 280                 285
Met Asp Lys Leu Thr Leu Lys Gly Met Ser Tyr Val Met Cys Thr Gly
    290                 295                 300
Ser Phe Lys Leu Glu Lys Glu Leu Ala Glu Thr Gln His Gly Thr Val
305                 310                 315                 320
Leu Val Gln Ile Lys Tyr Glu Gly Thr Asp Ala Pro Cys Lys Ile Pro
                325                 330                 335
Phe Ser Thr Gln Asp Glu Lys Gly Val Thr Gln Asn Gly Arg Leu Ile
            340                 345                 350
Thr Ala Asn Pro Ile Val Thr Asp Lys Glu Lys Pro Val Asn Ile Glu
        355                 360                 365
Ala Glu Pro Pro Phe Gly Glu Ser Tyr Ile Val Ile Gly Ala Gly Glu
    370                 375                 380
Lys Ala Leu Lys Leu Ser Trp Phe Lys Lys Gly Ser Ser Ile Gly Lys
385                 390                 395                 400
Met Phe Glu Ala Thr Ala Arg Gly Ala Arg Arg Met Ala Ile Leu Gly
                405                 410                 415
Asp Thr Ala Trp Asp Phe Gly Ser Ile Gly Gly Val Phe Thr Ser Val
            420                 425                 430
Gly Lys Leu Val His Gln Ile Phe Gly Thr Ala Tyr Gly Val Leu Phe
        435                 440                 445
Ser Gly Val Ser Trp Thr Met Lys Ile Gly Ile Gly Val Leu Leu Thr
    450                 455                 460
Trp Leu Gly Leu Asn Ser Arg Ser Thr Ser Leu Ser Met Thr Cys Ile
465                 470                 475                 480
Ala Val Gly Leu Val Thr Leu Tyr Leu Gly Val Met Val Gln Ala
                485                 490                 495
```

<210> SEQ ID NO 13
<211> LENGTH: 495
<212> TYPE: PRT
<213> ORGANISM: Dengue virus type 2

<400> SEQUENCE: 13

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Lys Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Lys Gln Glu Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg Tyr Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
            405                 410                 415

Asp Thr Ala Trp Asp Phe Gly Ser Leu Gly Gly Val Phe Thr Ser Ile
        420                 425                 430

Gly Lys Ala Leu His Gln Val Phe Gly Ala Ile Tyr Gly Ala Ala Phe
            435                 440                 445

Ser Gly Val Ser Trp Thr Met Lys Ile Leu Ile Gly Val Ile Ile Thr
        450                 455                 460

Trp Ile Gly Met Asn Ser Arg Ser Thr Ser Leu Ser Val Ser Leu Val
465                 470                 475                 480

Leu Val Gly Ile Val Thr Leu Tyr Leu Gly Val Met Val Gln Ala
            485                 490                 495

<210> SEQ ID NO 14
<211> LENGTH: 493
<212> TYPE: PRT
<213> ORGANISM: Dengue virus type 3

<400> SEQUENCE: 14

Met Arg Cys Val Gly Val Gly Asn Arg Asp Phe Val Glu Gly Leu Ser
1               5                   10                  15

Gly Ala Ser Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Asp Thr Gln Gly Val Thr Val
145                 150                 155                 160

Glu Ile Thr Pro Gln Ala Ser Thr Val Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly

```
                   260                 265                 270
Gly Thr Ser Ile Phe Ala Gly His Leu Lys Cys Arg Leu Lys Met Asp
                275                 280                 285

Lys Leu Glu Leu Lys Gly Met Ser Tyr Ala Met Cys Leu Asn Thr Phe
            290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Thr Lys Lys Glu Pro Val Asn Ile Glu Ala Glu
            355                 360                 365

Pro Pro Phe Gly Glu Ser Asn Ile Val Ile Gly Ile Gly Asp Lys Ala
        370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Ile Met Lys Ile Gly Ile Gly Val Leu Leu Thr Trp Ile
450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Val Val Val Gln Ala
                485                 490

<210> SEQ ID NO 15
<211> LENGTH: 495
<212> TYPE: PRT
<213> ORGANISM: Dengue virus type 4

<400> SEQUENCE: 15

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
    130                 135                 140
```

Asn Gly Asp Thr His Ala Val Gly Asn Asp Thr Ser Asn His Gly Glu
145                 150                 155                 160

Thr Ala Thr Ile Thr Pro Arg Ser Pro Ser Val Glu Val Lys Leu Pro
            165                 170                 175

Asp Tyr Gly Glu Leu Thr Leu Asp Cys Glu Pro Arg Ser Gly Ile Asp
        180                 185                 190

Phe Asn Glu Met Ile Leu Met Lys Met Lys Thr Lys Thr Trp Leu Val
    195                 200                 205

His Lys Gln Trp Phe Leu Asp Leu Pro Leu Pro Trp Thr Ala Gly Ala
210                 215                 220

Asp Thr Ser Glu Val His Trp Asn His Lys Glu Arg Met Val Thr Phe
225                 230                 235                 240

Lys Val Pro His Ala Lys Arg Gln Asp Val Thr Val Leu Gly Ser Gln
            245                 250                 255

Glu Gly Ala Met His Ser Ala Leu Ala Gly Ala Thr Glu Val Asp Ser
        260                 265                 270

Gly Asp Gly Asn His Met Phe Ala Gly His Leu Lys Cys Lys Val Arg
    275                 280                 285

Met Glu Lys Leu Arg Ile Lys Gly Met Ser Tyr Thr Met Cys Ser Gly
290                 295                 300

Lys Phe Ser Ile Asp Lys Glu Met Ala Glu Thr Gln His Gly Thr Thr
305                 310                 315                 320

Val Val Lys Val Lys Tyr Glu Gly Thr Gly Ala Pro Cys Lys Val Pro
            325                 330                 335

Ile Glu Ile Arg Asp Val Asn Lys Glu Lys Val Val Gly Arg Ile Ile
        340                 345                 350

Ser Ser Thr Pro Phe Ala Glu Asn Thr Asn Ser Val Thr Asn Ile Glu
    355                 360                 365

Leu Glu Pro Pro Phe Gly Asp Ser Tyr Ile Val Ile Gly Val Gly Asp
370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
            405                 410                 415

Glu Thr Ala Trp Asp Phe Gly Ser Val Gly Gly Leu Leu Thr Ser Leu
        420                 425                 430

Gly Lys Ala Val His Gln Val Phe Gly Ser Val Tyr Thr Thr Met Phe
    435                 440                 445

Gly Gly Val Ser Trp Met Val Arg Ile Leu Ile Gly Leu Leu Val Leu
450                 455                 460

Trp Ile Gly Thr Asn Ser Arg Asn Thr Ser Met Ala Met Ser Cys Ile
465                 470                 475                 480

Ala Val Gly Gly Ile Thr Leu Phe Leu Gly Phe Thr Val His Ala
            485                 490                 495

<210> SEQ ID NO 16
<211> LENGTH: 500
<212> TYPE: PRT
<213> ORGANISM: Japanese encephalitis virus

<400> SEQUENCE: 16

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

```
Ile Met Ala Asn Asp Lys Pro Thr Leu Asp Val Arg Met Ile Asn Ile
            35                  40                  45

Glu Ala Ser Gln Leu Ala Glu Val Arg Ser Tyr Cys Tyr His Ala Ser
        50                  55                  60

Val Thr Asp Ile Ser Thr Val Ala Arg Cys Pro Thr Thr Gly Glu Ala
 65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
                100                 105                 110

Ile Asp Thr Cys Ala Lys Phe Ser Cys Thr Ser Lys Ala Ile Gly Arg
                115                 120                 125

Thr Ile Gln Pro Glu Asn Ile Lys Tyr Glu Val Gly Ile Phe Val His
            130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
                180                 185                 190

Arg Ser Gly Leu Asn Thr Glu Ala Phe Tyr Val Met Thr Val Gly Ser
                195                 200                 205

Arg Ser Phe Leu Val His Arg Glu Trp Phe His Asp Leu Ala Leu Pro
                210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
                260                 265                 270

Glu Tyr Ser Ser Ser Val Lys Leu Thr Ser Gly His Leu Lys Cys Arg
                275                 280                 285

Leu Lys Met Asp Lys Leu Ala Leu Lys Gly Thr Thr Tyr Gly Met Cys
                290                 295                 300

Thr Lys Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
                340                 345                 350

Arg Leu Val Thr Val Asn Pro Phe Val Ala Thr Ser Ser Ala Asn Ser
                355                 360                 365

Lys Val Leu Val Glu Met Glu Pro Pro Phe Gly Asp Ser Tyr Ile Val
                370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
                420                 425                 430

Val Phe Asn Ser Ile Gly Lys Ala Val His Gln Val Phe Gly Gly Ala
                435                 440                 445
```

```
Phe Arg Thr Leu Phe Gly Gly Met Ser Trp Ile Thr Gln Gly Leu Met
450                 455                 460
Gly Ala Leu Leu Leu Trp Met Gly Val Asn Ala Arg Asp Arg Ser Ile
465                 470                 475                 480
Ala Leu Ala Phe Leu Ala Thr Gly Gly Val Leu Val Phe Leu Ala Thr
            485                 490                 495
Asn Val His Ala
            500

<210> SEQ ID NO 17
<211> LENGTH: 500
<212> TYPE: PRT
<213> ORGANISM: Usutu virus

<400> SEQUENCE: 17

Phe Asn Cys Leu Gly Met Ser Asn Arg Asp Phe Leu Glu Gly Val Ser
1               5                   10                  15
Gly Ala Thr Trp Val Asp Val Val Leu Glu Gly Asp Ser Cys Ile Thr
            20                  25                  30
Ile Met Ala Lys Asp Lys Pro Thr Ile Asp Ile Lys Met Met Glu Thr
        35                  40                  45
Glu Ala Thr Asn Leu Ala Glu Val Arg Ser Tyr Cys Tyr Leu Ala Thr
50                  55                  60
Val Ser Asp Val Ser Thr Val Ser Asn Cys Pro Thr Thr Gly Glu Ala
65                  70                  75                  80
His Asn Pro Lys Arg Ala Glu Asp Thr Tyr Val Cys Lys Ser Gly Val
                85                  90                  95
Thr Asp Arg Gly Trp Gly Asn Gly Cys Gly Leu Phe Gly Lys Gly Ser
            100                 105                 110
Ile Asp Thr Cys Ala Asn Phe Thr Cys Ser Leu Lys Ala Met Gly Arg
        115                 120                 125
Met Ile Gln Pro Glu Asn Val Lys Tyr Glu Val Gly Ile Phe Ile His
130                 135                 140
Gly Ser Thr Ser Ser Asp Thr His Gly Asn Tyr Ser Ser Gln Leu Gly
145                 150                 155                 160
Ala Ser Gln Ala Gly Arg Phe Thr Ile Thr Pro Asn Ser Pro Ala Ile
                165                 170                 175
Thr Val Lys Met Gly Asp Tyr Gly Glu Ile Ser Val Glu Cys Glu Pro
            180                 185                 190
Arg Asn Gly Leu Asn Thr Glu Ala Tyr Tyr Ile Met Ser Val Gly Thr
        195                 200                 205
Lys His Phe Leu Val His Arg Glu Trp Phe Asn Asp Leu Ala Leu Pro
210                 215                 220
Trp Thr Ser Pro Ala Ser Ser Asn Trp Arg Asn Arg Glu Ile Leu Leu
225                 230                 235                 240
Glu Phe Glu Glu Pro His Ala Thr Lys Gln Ser Val Val Ala Leu Gly
                245                 250                 255
Ser Gln Glu Gly Ala Leu His Gln Ala Leu Ala Gly Ala Val Pro Val
            260                 265                 270
Ser Phe Ser Gly Ser Val Lys Leu Thr Ser Gly His Leu Lys Cys Arg
        275                 280                 285
Val Lys Met Glu Lys Leu Thr Leu Lys Gly Thr Thr Tyr Gly Met Cys
290                 295                 300
Thr Glu Lys Phe Ser Phe Ala Lys Asn Pro Ala Asp Thr Gly His Gly
305                 310                 315                 320
```

```
Thr Val Val Leu Glu Leu Gln Tyr Thr Gly Ser Asp Gly Pro Cys Lys
                325                 330                 335

Ile Pro Ile Ser Ile Val Ala Ser Leu Ser Asp Leu Thr Pro Ile Gly
            340                 345                 350

Arg Met Val Thr Ala Asn Pro Tyr Val Ala Ser Ser Glu Ala Asn Ala
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Ser Ile Gly Lys Ala Phe Ile Thr Thr Ile Lys Gly Ala Gln Arg
                405                 410                 415

Leu Ala Ala Leu Gly Asp Thr Ala Trp Asp Phe Gly Ser Val Gly Gly
            420                 425                 430

Ile Phe Asn Ser Val Gly Lys Ala Val His Gln Val Phe Gly Gly Ala
        435                 440                 445

Phe Arg Thr Leu Phe Gly Gly Met Ser Trp Ile Thr Gln Gly Leu Met
    450                 455                 460

Gly Ala Leu Leu Leu Trp Met Gly Val Asn Ala Arg Asp Arg Ser Ile
465                 470                 475                 480

Ala Leu Val Met Leu Ala Thr Gly Gly Val Leu Leu Phe Leu Ala Thr
                485                 490                 495

Asn Val His Ala
            500

<210> SEQ ID NO 18
<211> LENGTH: 404
<212> TYPE: PRT
<213> ORGANISM: Artificial Sequence
<220> FEATURE:
<223> OTHER INFORMATION: mutant ectodomain of E protein from usutu virus
<220> FEATURE:
<221> NAME/KEY: MUTAGEN
<222> LOCATION: (76)..(76)
<223> OTHER INFORMATION: a naturally occurring amino acid except T
<220> FEATURE:
<221> NAME/KEY: MUTAGEN
<222> LOCATION: (77)..(77)
<223> OTHER INFORMATION: a naturally occurring amino acid except T
<220> FEATURE:
<221> NAME/KEY: MUTAGEN
<222> LOCATION: (101)..(101)
<223> OTHER INFORMATION: a naturally occurring amino acid except W
<220> FEATURE:
<221> NAME/KEY: MUTAGEN
<222> LOCATION: (107)..(107)
<223> OTHER INFORMATION: a naturally occurring amino acid except L

<400> SEQUENCE: 18

Phe Asn Cys Leu Gly Met Ser Asn Arg Asp Phe Leu Glu Gly Val Ser
1               5                   10                  15

Gly Ala Thr Trp Val Asp Val Val Leu Glu Gly Asp Ser Cys Ile Thr
            20                  25                  30

Ile Met Ala Lys Asp Lys Pro Thr Ile Asp Ile Lys Met Met Glu Thr
        35                  40                  45

Glu Ala Thr Asn Leu Ala Glu Val Arg Ser Tyr Cys Tyr Leu Ala Thr
    50                  55                  60

Val Ser Asp Val Ser Thr Val Ser Asn Cys Pro Xaa Xaa Gly Glu Ala
65                  70                  75                  80

His Asn Pro Lys Arg Ala Glu Asp Thr Tyr Val Cys Lys Ser Gly Val
```

Thr Asp Arg Gly Xaa Gly Asn Gly Cys Gly Xaa Phe Gly Lys Gly Ser
            85              90              95
            100             105             110

Ile Asp Thr Cys Ala Asn Phe Thr Cys Ser Leu Lys Ala Met Gly Arg
            115             120             125

Met Ile Gln Pro Glu Asn Val Lys Tyr Glu Val Gly Ile Phe Ile His
            130             135             140

Gly Ser Thr Ser Ser Asp Thr His Gly Asn Tyr Ser Ser Gln Leu Gly
145             150             155             160

Ala Ser Gln Ala Gly Arg Phe Thr Ile Thr Pro Asn Ser Pro Ala Ile
            165             170             175

Thr Val Lys Met Gly Asp Tyr Gly Glu Ile Ser Val Glu Cys Glu Pro
            180             185             190

Arg Asn Gly Leu Asn Thr Glu Ala Tyr Tyr Ile Met Ser Val Gly Thr
            195             200             205

Lys His Phe Leu Val His Arg Glu Trp Phe Asn Asp Leu Ala Leu Pro
            210             215             220

Trp Thr Ser Pro Ala Ser Ser Asn Trp Arg Asn Arg Glu Ile Leu Leu
225             230             235             240

Glu Phe Glu Glu Pro His Ala Thr Lys Gln Ser Val Val Ala Leu Gly
            245             250             255

Ser Gln Glu Gly Ala Leu His Gln Ala Leu Ala Gly Ala Val Pro Val
            260             265             270

Ser Phe Ser Gly Ser Val Lys Leu Thr Ser Gly His Leu Lys Cys Arg
            275             280             285

Val Lys Met Glu Lys Leu Thr Leu Lys Gly Thr Thr Tyr Gly Met Cys
            290             295             300

Thr Glu Lys Phe Ser Phe Ala Lys Asn Pro Ala Asp Thr Gly His Gly
305             310             315             320

Thr Val Val Leu Glu Leu Gln Tyr Thr Gly Ser Asp Gly Pro Cys Lys
            325             330             335

Ile Pro Ile Ser Ile Val Ala Ser Leu Ser Asp Leu Thr Pro Ile Gly
            340             345             350

Arg Met Val Thr Ala Asn Pro Tyr Val Ala Ser Ser Glu Ala Asn Ala
            355             360             365

Lys Val Leu Val Glu Met Glu Pro Pro Phe Gly Asp Ser Tyr Ile Val
            370             375             380

Val Gly Arg Gly Asp Lys Gln Ile Asn His His Trp His Lys Ala Gly
385             390             395             400

Ser Ser Ile Gly

<210> SEQ ID NO 19
<211> LENGTH: 493
<212> TYPE: PRT
<213> ORGANISM: Yellow fever virus

<400> SEQUENCE: 19

Ala His Cys Ile Gly Ile Thr Asp Arg Asp Phe Ile Glu Gly Val His
1               5               10              15

Gly Gly Thr Trp Val Ser Ala Thr Leu Glu Gln Asp Lys Cys Val Thr
            20              25              30

Val Met Ala Pro Asp Lys Pro Ser Leu Asp Ile Ser Leu Glu Thr Val
            35              40              45

Ala Ile Asp Gly Pro Ala Glu Ala Arg Lys Val Cys Tyr Ser Ala Val

```
            50                  55                  60
Leu Thr Asn Val Lys Ile Asn Asp Lys Cys Pro Ser Thr Gly Glu Ala
 65                  70                  75                  80

His Leu Glu Glu Glu Asn Gly Asp Asn Ala Cys Lys Arg Thr Tyr
                     85                  90                  95

Ser Asp Arg Gly Trp Gly Asn Gly Cys Gly Leu Phe Gly Lys Gly Ser
                100                 105                 110

Ile Val Ala Cys Ala Lys Phe Thr Cys Ala Lys Ser Met Ser Leu Phe
                115                 120                 125

Glu Val Asp Gln Thr Lys Ile Gln Tyr Val Ile Arg Ala Gln Leu His
                130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Ala Glu Phe Thr Gly Tyr Gly
                165                 170                 175

Lys Ala Thr Leu Glu Cys Gln Val Gln Thr Ala Leu Asp Phe Ser Asn
                180                 185                 190

Ser Tyr Ile Ala Glu Met Glu Lys Glu Ser Trp Ile Val Asp Lys Gln
                195                 200                 205

Trp Ala Gln Asp Leu Thr Leu Pro Trp Gln Ser Gly Ser Gly Gly Val
                210                 215                 220

Trp Arg Glu Met His His Leu Val Glu Phe Glu Pro Pro His Ala Ala
225                 230                 235                 240

Thr Ile Lys Val Leu Ala Leu Gly Asn Gln Glu Gly Ser Leu Lys Thr
                245                 250                 255

Ala Leu Thr Gly Ala Met Arg Val Thr Lys Asp Thr Asn Asn Ser Lys
                260                 265                 270

Leu Tyr Lys Leu His Gly Gly His Val Ala Cys Arg Val Lys Leu Ser
                275                 280                 285

Ala Leu Thr Leu Lys Gly Thr Ser Tyr Lys Met Cys Thr Asp Lys Met
                290                 295                 300

Ser Phe Val Lys Asn Pro Thr Asp Thr Gly His Gly Thr Ala Val Met
305                 310                 315                 320

Gln Val Lys Val Pro Lys Gly Ala Pro Cys Arg Ile Pro Val Met Val
                325                 330                 335

Ala Asp Asp Leu Thr Ala Ala Val Asn Lys Gly Ile Leu Val Thr Val
                340                 345                 350

Asn Pro Ile Ala Ser Thr Asn Asp Asp Glu Val Leu Ile Glu Val Asn
                355                 360                 365

Pro Pro Phe Gly Asp Ser Tyr Ile Ile Val Gly Thr Gly Asp Ser Arg
                370                 375                 380

Leu Thr Tyr Gln Trp His Lys Glu Gly Ser Ser Ile Gly Lys Leu Phe
385                 390                 395                 400

Thr Gln Thr Met Lys Gly Ala Glu Arg Leu Ala Val Met Gly Asp Ala
                405                 410                 415

Ala Trp Asp Phe Gly Ser Ala Gly Gly Phe Phe Thr Ser Val Gly Lys
                420                 425                 430

Gly Ile His Thr Val Phe Gly Ser Ala Phe Gln Gly Leu Phe Gly Gly
                435                 440                 445

Leu Ser Trp Ile Thr Lys Val Ile Met Gly Val Val Leu Ile Trp Val
                450                 455                 460

Gly Ile Asn Thr Arg Asn Met Thr Met Ser Met Ser Met Ile Leu Val
465                 470                 475                 480
```

```
Gly Val Ile Met Met Phe Leu Ser Leu Gly Val Gly Ala
                485                 490

<210> SEQ ID NO 20
<211> LENGTH: 501
<212> TYPE: PRT
<213> ORGANISM: West Nile virus

<400> SEQUENCE: 20

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Asp Val Arg Ser Tyr Cys Tyr Leu Ala Ser
    50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Thr Thr Lys Ala Thr Gly Trp
        115                 120                 125

Ile Ile Gln Lys Glu Asn Ile Lys Tyr Glu Val Ala Ile Phe Val His
    130                 135                 140

Gly Pro Thr Thr Val Glu Ser His Gly Asn Tyr Ser Thr Gln Thr Gly
145                 150                 155                 160

Ala Thr Gln Ala Gly Arg Phe Ser Ile Thr Pro Ser Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Ser Ala Tyr Tyr Val Met Ser Val Gly Ala
        195                 200                 205

Lys Ser Phe Leu Val His Arg Glu Trp Phe Met Asp Leu Asn Leu Pro
    210                 215                 220

Trp Ser Ser Ala Gly Ser Thr Thr Trp Arg Asn Arg Glu Thr Leu Met
225                 230                 235                 240

Glu Phe Glu Glu Pro His Ala Thr Lys Gln Ser Val Val Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Ala Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
```

```
                355                 360                 365
Ser Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Arg Gly Ala Gln
                405                 410                 415

Arg Leu Ala Ala Leu Gly Asp Thr Ala Trp Asp Phe Gly Ser Val Gly
                420                 425                 430

Gly Val Phe Thr Ser Val Gly Lys Ala Ile His Gln Val Phe Gly Gly
                435                 440                 445

Ala Phe Arg Ser Leu Phe Gly Gly Met Ser Trp Ile Thr Gln Gly Leu
                450                 455                 460

Leu Gly Ala Leu Leu Leu Trp Met Gly Ile Asn Ala Arg Asp Arg Ser
465                 470                 475                 480

Ile Ala Met Thr Phe Leu Ala Val Gly Gly Val Leu Leu Phe Leu Ser
                485                 490                 495

Val Asn Val His Ala
                500

<210> SEQ ID NO 21
<211> LENGTH: 404
<212> TYPE: PRT
<213> ORGANISM: West Nile virus

<400> SEQUENCE: 21

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
                20                  25                  30

Ile Met Ser Lys Asp Lys Pro Thr Ile Asp Val Lys Met Met Asn Met
                35                  40                  45

Glu Ala Ala Asn Leu Ala Asp Val Arg Ser Tyr Cys Tyr Leu Ala Ser
50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
                100                 105                 110

Ile Asp Thr Cys Ala Lys Phe Ala Cys Thr Thr Lys Ala Thr Gly Trp
                115                 120                 125

Ile Ile Gln Lys Glu Asn Ile Lys Tyr Glu Val Ala Ile Phe Val His
                130                 135                 140

Gly Pro Thr Thr Val Glu Ser His Gly Asn Tyr Ser Thr Gln Thr Gly
145                 150                 155                 160

Ala Thr Gln Ala Gly Arg Phe Ser Ile Thr Pro Ser Ala Pro Ser Tyr
                165                 170                 175

Thr Leu Lys Leu Gly Glu Tyr Gly Glu Val Thr Val Asp Cys Glu Pro
                180                 185                 190

Arg Ser Gly Ile Asp Thr Ser Ala Tyr Tyr Val Met Ser Val Gly Ala
                195                 200                 205

Lys Ser Phe Leu Val His Arg Glu Trp Phe Met Asp Leu Asn Leu Pro
210                 215                 220
```

```
Trp Ser Ser Ala Gly Ser Thr Thr Trp Arg Asn Arg Glu Thr Leu Met
225                 230                 235                 240

Glu Phe Glu Glu Pro His Ala Thr Lys Gln Ser Val Val Ala Leu Gly
            245                 250                 255

Ser Gln Glu Gly Ala Leu His Gln Ala Leu Ala Gly Ala Ile Pro Val
        260                 265                 270

Glu Phe Ser Ser Asn Thr Val Lys Leu Thr Ser Gly His Leu Lys Cys
    275                 280                 285

Arg Val Lys Met Glu Lys Leu Gln Leu Lys Gly Thr Thr Tyr Gly Val
290                 295                 300

Cys Ser Lys Ala Phe Lys Phe Ala Gly Thr Pro Ala Asp Thr Gly His
305                 310                 315                 320

Gly Thr Val Val Leu Glu Leu Gln Tyr Thr Gly Thr Asp Gly Pro Cys
            325                 330                 335

Lys Val Pro Ile Ser Ser Val Ala Ser Leu Asn Asp Leu Thr Pro Val
        340                 345                 350

Gly Arg Leu Val Thr Val Asn Pro Phe Val Ser Val Ala Thr Ala Asn
    355                 360                 365

Ser Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile

<210> SEQ ID NO 22
<211> LENGTH: 400
<212> TYPE: PRT
<213> ORGANISM: West Nile virus

<400> SEQUENCE: 22

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190
```

-continued

Arg Ser Gly Ile Asp Thr Asn Ala Tyr Tyr Val Met Thr Val Gly Thr
            195                 200                 205

Lys Thr Phe Leu Val His Arg Glu Trp Phe Met Asp Leu Asn Leu Pro
210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
            245                 250                 255

Ser Gln Glu Gly Ala Leu His Gln Leu Ala Gly Ala Ile Pro Val
                260                 265                 270

Glu Phe Ser Ser Asn Thr Val Lys Leu Thr Ser Gly His Leu Lys Cys
            275                 280                 285

Arg Val Lys Met Glu Lys Leu Gln Leu Lys Gly Thr Thr Tyr Gly Val
290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
            355                 360                 365

Ala Lys Val Leu Ile Glu Leu Glu Pro Pro Phe Gly Asp Ser Tyr Ile
            370                 375                 380

Val Val Gly Arg Gly Glu Gln Gln Ile Asn His His Trp His Lys Ser
385                 390                 395                 400

<210> SEQ ID NO 23
<211> LENGTH: 394
<212> TYPE: PRT
<213> ORGANISM: Dengue virus

<400> SEQUENCE: 23

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
        50                  55                  60

Leu Thr Asn Thr Thr Thr Glu Ser Arg Cys Pro Thr Gln Gly Glu Pro
65                  70                  75                  80

Thr Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Val Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175

```
Gly Tyr Gly Thr Val Thr Met Glu Cys Ser Pro Arg Thr Gly Leu Asp
            180                 185                 190

Phe Asn Glu Met Val Leu Leu Gln Met Lys Asp Lys Ala Trp Leu Val
            195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys
385                 390

<210> SEQ ID NO 24
<211> LENGTH: 392
<212> TYPE: PRT
<213> ORGANISM: Dengue virus

<400> SEQUENCE: 24

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Ile Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
```

145                 150                 155                 160
Glu Ile Thr Ser Gln Ala Ser Thr Ala Glu Ala Ile Leu Pro Glu Tyr
                    165                 170                 175
Gly Thr Leu Gly Leu Glu Cys Ser Pro Arg Thr Gly Leu Asp Phe Asn
                    180                 185                 190
Glu Met Ile Leu Leu Thr Met Lys Asp Lys Ala Trp Met Val His Arg
                    195                 200                 205
Gln Trp Phe Phe Asp Leu Pro Leu Pro Trp Thr Ser Gly Ala Thr Thr
                    210                 215                 220
Lys Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                    245                 250                 255
Ala Met His Thr Ala Leu Thr Gly Ala Thr Glu Ile Gln Thr Ser Gly
                    260                 265                 270
Gly Thr Ser Ile Phe Ala Gly His Leu Lys Cys Arg Leu Lys Met Asp
                    275                 280                 285
Lys Leu Lys Leu Lys Gly Met Ser Tyr Ala Met Cys Leu Asn Thr Phe
290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                    325                 330                 335
Thr Glu Asp Gly Gln Gly Lys Ala Gly Asn Gly Arg Leu Ile Thr Ala
                    340                 345                 350
Asn Pro Val Val Thr Lys Lys Glu Glu Pro Val Asn Ile Glu Ala Glu
                    355                 360                 365
Pro Pro Phe Gly Glu Ser Asn Ile Val Ile Gly Ile Gly Asp Lys Ala
                    370                 375                 380
Leu Lys Ile Asn Trp Tyr Arg Lys
385                 390

<210> SEQ ID NO 25
<211> LENGTH: 395
<212> TYPE: PRT
<213> ORGANISM: Tick-borne encephalitis virus

<400> SEQUENCE: 25

Ser Arg Cys Thr His Leu Glu Asn Arg Asp Phe Val Thr Gly Thr Gln
1               5                   10                  15
Gly Thr Thr Arg Val Thr Leu Val Leu Glu Leu Gly Gly Cys Val Thr
                    20                  25                  30
Ile Thr Ala Glu Gly Lys Pro Ser Met Asp Val Trp Leu Asp Ala Ile
                35                  40                  45
Tyr Gln Glu Asn Pro Ala Lys Thr Arg Glu Tyr Cys Leu His Ala Lys
            50                  55                  60
Leu Ser Asp Thr Lys Val Ala Ala Arg Cys Pro Thr Met Gly Pro Ala
65                  70                  75                  80
Thr Leu Ala Glu Glu His Gln Gly Gly Thr Val Cys Lys Arg Asp Gln
                    85                  90                  95
Ser Asp Arg Gly Trp Gly Asn His Cys Gly Leu Phe Gly Lys Gly Ser
                    100                 105                 110
Ile Val Ala Cys Val Lys Ala Ala Cys Glu Ala Lys Lys Lys Ala Thr
                115                 120                 125

-continued

```
Gly His Val Tyr Asp Ala Asn Lys Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Ile Ser Ser Glu Lys Thr Ile Leu Thr Met
                165                 170                 175

Gly Glu Tyr Gly Asp Val Ser Leu Leu Cys Arg Val Ala Ser Gly Val
                180                 185                 190

Asp Leu Ala Gln Thr Val Ile Leu Glu Leu Asp Lys Thr Val Glu His
            195                 200                 205

Leu Pro Thr Ala Trp Gln Val His Arg Asp Trp Phe Asn Asp Leu Ala
    210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
    275                 280                 285

Thr Cys Glu Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
            355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys
385                 390                 395
```